United States Patent [19]
Brierley et al.

[11] Patent Number: 5,612,198
[45] Date of Patent: *Mar. 18, 1997

[54] PRODUCTION OF INSULIN-LIKE GROWTH FACTOR-1 IN METHYLOTROPHIC YEAST CELLS

[75] Inventors: Russell A. Brierley, Exton, Pa.;
Geneva R. Davis, San Diego, Calif.;
Gregory C. Holtz, San Diego, Calif.;
Martin A. Gleeson, San Diego, Calif.;
Bradley D. Howard, San Diego, Calif.

[73] Assignee: The Salk Institute, La Jolla, Calif.

[ * ] Notice: The term of this patent shall not extend beyond the expiration date of Pat. No. 5,324,639.

[21] Appl. No.: 308,196

[22] Filed: Sep. 19, 1994

Related U.S. Application Data

[63] Continuation of Ser. No. 983,523, filed as PCT/US91/06452, Sep. 4, 1991, abandoned, which is a continuation-in-part of Ser. No. 578,728, Sep. 4, 1990, abandoned.

[51] Int. Cl.$^6$ .............................. C12N 15/18; C12N 1/19
[52] U.S. Cl. ...................... 435/69.9; 435/69.4; 435/69.8; 435/255.5; 435/255.6
[58] Field of Search .................................. 435/69.1, 69.7, 435/69.8, 69.9, 320.1, 172.3, 254.11, 254.21, 255.5, 254.23, 255.4, 255.6; 536/23.4

[56] References Cited

U.S. PATENT DOCUMENTS

| | | | |
|---|---|---|---|
| 4,546,082 | 10/1985 | Kurjan et al. | 435/172.3 |
| 4,769,361 | 9/1988 | Burleigh et al. | 514/12 |
| 4,812,405 | 3/1989 | Lair et al. | 435/255 |
| 4,837,148 | 6/1989 | Cregg | 435/172.3 |
| 4,855,231 | 8/1989 | Stroman et al. | 435/68 |
| 4,870,008 | 9/1989 | Brake | 435/70 |
| 4,879,231 | 11/1989 | Stroman et al. | 435/172.3 |
| 4,882,279 | 11/1989 | Cregg | 435/172.3 |
| 4,895,800 | 1/1990 | Tschopp et al. | 435/69.3 |
| 4,929,555 | 5/1990 | Cregg et al. | 435/172.3 |
| 4,963,665 | 10/1990 | Rotwein et al. | 530/399 |
| 4,997,916 | 3/1991 | Aviv et al. | 435/69.4 |
| 5,070,075 | 12/1991 | Rotwein et al. | 514/12 |
| 5,102,789 | 4/1992 | Siegel et al. | 435/69.4 |
| 5,231,178 | 7/1993 | Holtz et al. | 530/399 |
| 5,258,302 | 11/1993 | Vedick et al. | 435/254.23 |
| 5,268,273 | 12/1993 | Buckholz | 435/69.1 |
| 5,324,639 | 6/1994 | Brierley et al. | 435/69.4 |
| 5,324,660 | 6/1994 | Gleeson et al. | 435/254.23 |

FOREIGN PATENT DOCUMENTS

| | | |
|---|---|---|
| 0123228 | 10/1984 | European Pat. Off. |
| 0128733 | 12/1984 | European Pat. Off. |
| 0142268 | 5/1985 | European Pat. Off. |
| 0173378 | 3/1986 | European Pat. Off. |
| 0206783 | 12/1986 | European Pat. Off. |
| 0213593 | 3/1987 | European Pat. Off. |
| 0324274 | 7/1989 | European Pat. Off. |
| 0327797 | 8/1989 | European Pat. Off. |
| 0341215 | 11/1989 | European Pat. Off. |
| 0360411 | 3/1990 | European Pat. Off. |
| 0390676 | 10/1990 | European Pat. Off. |
| 0591524 | 4/1994 | European Pat. Off. |
| 8403103 | 8/1984 | WIPO |
| 8600619 | 11/1986 | WIPO |
| 8904320 | 5/1989 | WIPO |
| 9000191 | 1/1990 | WIPO |
| 9002810 | 3/1990 | WIPO |
| 9002198 | 3/1990 | WIPO |
| 9003431 | 4/1990 | WIPO |
| 9009434 | 8/1990 | WIPO |
| 9105057 | 4/1991 | WIPO |
| 9204441 | 3/1992 | WIPO |
| 9213951 | 8/1992 | WIPO |
| 9217595 | 10/1992 | WIPO |
| 9309233 | 5/1993 | WIPO |

OTHER PUBLICATIONS

Moehle, et al., "Protease B of the Lysosomelike Vacuole of the Yeast *Saccharomyces cerevisiae* is Homologous to the Subtilisin Family of Serine Proteases," *Mol. Cell. Biol.*, 7(12):4390–4399 (1987).

Gellisen, et al., "Heterologous Protein Production in Yeast," *Antonie van Leeuwenhoek*, 62:79–93 (1992).

Strasser, et al., "Applications of Genetically Manipulated Yeasts," *Appl. Mol. Genet. Fungi*, 10:161–169 (1991).

Armstrong, et al., "Biological Activity of Insulin–Like Growth Factor–I Purified from Chicken Serum," *Domestic Animal Endocrinology*, 7(3):383–393 (1990).

Baxter, et al., "Natural and Recombinant DNA–Derived Human Insulin–Like Growth Factor–I Compared for Use in Radioligand Assays," *Chemical Abstracts*, 107:86 (1987).

Chernausek, et al., "Efficient Purification of Somatomedin–C/Insulin–Like Growth Factor I Using Immunoaffinity Chromatography," *Biochem. and Biophys. Research Comm.*, 126(1):282–288 (1985).

Cornell, et al., "Isolation of Insulin–Like Growth Factors I and II From Human Plasma," *Preparative Biochemistry*, 14(2):123–128 (1984).

Cregg, J.M., "Expression of Foreign Genes in *Pichia pastoris*", in *Genetics and Molecular Biology of Industrial Microorganisms*, Hershberger, et al. (Eds.) pp. 343–352, Amer. Soc. Microbio., Washington, D.C. (1989).

(List continued on next page.)

*Primary Examiner*—Marianne P. Allen
*Attorney, Agent, or Firm*—Stephanie Seidman; Brown Martin Haller & McClain

[57] ABSTRACT

Insulin-like growth factor-1 (IGF-1), a naturally occurring, relatively short, single chain polypeptide, is prepared by growing methylotrophic yeast transformants containing in their genome at least one copy of DNA encoding IGF-1, in operational linkage with DNA encoding a signal sequence, which is effective for directing secretion of proteins from the host cells and which also includes the proteolytic processing site lys-arg and may include one or more glu-ala sequences. In preferred embodiments the signal sequence is the *S. cerevisiae* alpha mating factor pre-pro sequence. Expression of both the DNA encoding IGF-1 and the pre-pro signal sequence is regulated by a promoter region derived from a methanol responsive gene of a methylotrophic yeast. DNA constructs and recombinant methylotrophic yeast strains used for the expression and secretion of IGF-1 are also provided. For preferred embodiments, protease deficient *Pichia pastoris* strains are provided.

56 Claims, 6 Drawing Sheets

OTHER PUBLICATIONS

Lynch, et al., "A Combination of Platelet–Derived and Insulin–Like Growth Factors Enhances Periodontal Regeneration," *J. Clin. Periodontol*, 16:545–548 (1989).

Lynch, et al., "Role of Platelet–Derived Growth Factor in Wound Healing: Synergistic Effects with Other Growth Factors," *Proc. Natl. Acad. Sci. USA*, 84:7696–7700.

Meng, et al., "Reduction Studies on Bacterial Recombinant Somatomedin C/Insulin–Like Growth Factor–I," *Journal of Chromatography*, 443:183–192 (1988).

Peptides, et al., "An Improved Method for the Purification of Human Insulin–Like Growth Factors I and II," *Endocrinology*, 118(5):2034–2038.

Pfeifle, et al., "Insulin–Like Growth Factor I/Somatomedin–C: A Rapid Isolation Procedure with FPLC," *Preparative Biochemistry*, 15(5):291–307 (1985).

M.A. Preece, "The Somatomedins," *Horm. Blood*, 4:81–108 (1983).

Ray and Wallis, "Use of High–Performance Liquid Chromatography in the Purification of Human Somatomedin–C," *Biochem. Soc. Trans.*, 13:1233–1234 (1985).

Rotwein et al., "Organization and Sequence of the Human Insulin–Like Growth Factor I Gene," *J. Biol. Chem.*, 261(11):4828–4832 (1986).

Rubin, et al., "Isolation and Partial Sequence Analysis of Rat Basic Somatomedin", *Endocrinology*, 110:(3):734–740 (1982).

Svoboda, et al., "Purification of Somatomedin–C from Human Plasma: Chemical and Biological Properties, Partial Sequence Analysis, and Relationship to Other Somatomedins," *Amer. Chem. Soc.*, 19(4):790–797 (1980).

Wang, et al., "Purification and Assay of Insulin–Like Growth Factor–Binding Protein–I: Measurement of Circulating Levels Throughout Pregnancy," *J. of Endocrinology*, 128:161–168 (1991).

Arrand, "Preparation of nucleic acid probes," *Nucleic Acid Hybridisation: A Practical Approach*, pp. 17, 22–24, 45–45 (1985).

Burleigh and Meng, "Development of biosynthetic somatomedin–C/IGF–I as a product for cell culture," *Amer. Biotech. Laboratory*, 4(6):48–53 (1986).

Fellinger, et al., "Expression of the α–Galactosidase from *Cyamopsis tetragonolobe* (Guar) by *Hansenula polymorpha*," *Yeast* 7:463–473 (1991).

Gellissen, et al., "Heterologous gene expression in *Hansenula polymorpha*: Secretion of Glucoamylase (GAM), an amylolytic enzyme from *Schwanniomyces occidntalis*," *15th Int. Conf. on Yeast Genet. and Mol. Biol.* S423 09–13B (1990).

Gellissen, et al., "Progress in developing methylotrophic yeasts as expressio systems," *TIBTECH* 10:413–417 (1992).

Gellissen, et al., "High–level expression of foreign genes in *Hansenula polymorpha*," *Biotech. Adv.* 10:179–189 (1992).

Hodgkins, et al., "Expression of the glucose oxidase gene from *Aspergillus niger* in *Hansenula polymorpha* and its use as a reporter gene to isolate regulatory mutations," *Yeast* 9:625–635 (1993).

Janowicz, et al., "Formation of composite particles containing L–and S–antigens from hepatitis B virus in a methlotrophic yeast *Hansenula polymorpha*," *15th Int. Conf. on Yeast Genet. and Mol. Biol.* S424 09–14B (1990).

Janowicz, et al., "Expression system based on the methylotrophic yeast *Hansenula polymorpha*," *Eur. Conf. Biotechnol.* pp. 82–83 (1988).(Derwent Abstract provided.).

Petrides, et al., "An improved method for the purification of human insulin–like growth factors I and II," *Endocrinology*, 118(5):2034–2038 (1986).

Ammerer et al., "PEP4 gene of *Saccharomyces cerevisiae* encodes proteinase A, a vacuolar enzyme required for processing fo vacuolar precursors," *Molec. Cell Biol.*, 6(7):2490–2499 (1986).

Bayne et al., "Expression,purification and characterization of recombinant human insulin–like growth factor I in yeast," *Gene*, 66:235–244 (1988).

Boeke et al., "A positive selection for mutants lacking orotidine–5'–phosphate decarboxylase activity in yeast: 5–fluoro–orotic acid resistance," *Mol. Gen. Genet.*, 197:345–346 (1984).

Buell et al., "Optimizing the expression in *E. coli* of a synthetic gene encoding somatomedin–C (IGF–I)," *Nuc. Acids Res.*, 13(6):1923–1938 (1985).

Cregg et al., "*Pichia pastoris* as a host system for transformations," *Mol. Cell. Biol.*, 5(12):3376–3385 (1985).

Cregg, J.M., "Genetics of methylotrophic yeasts," in *Microbial Growth on C1 Compounds*, Van Verseveld et al. Eds., Martinus Nijhof Pubs, pp. 158–167 (1987).

Cregg et al., "Development of yeast transformation systems and construction of methanol–utilization–defective mutants of *Pichia pastori* by gene disruption," *Biol. Res. Indust. Yeast* , 2:1–18 (1986).

Cregg et al., "Development of the methylotrophic yeast, *Pichia pastoris*, as a host system for the production of foreign proteins," *Dev. in Indust. Microbio.*, 29:33–41 (1988).

Digan et al., "Continuous production of a novel lysozyme via secretion from the yeast, *Pichia pastoris, Biotechnology*", 7(2):160–164 (1989).

Digan et al., "Secretion of heterologous proteins from the methylotrophic yeast, *Pichia pastoris,*" *Devel. in Indust. Microbio.*, 29:59–65 (1988).

Elliot et al., "Yeast–derived recombinant human insulin–like growth factor I: production, purification, and structural characterization," *J. Prot. Chem.*, 9(1):95–104 (1990).

Ellis et al., "Isolation of alcohol oxidase and two other methanol regulatable genes from the yeast *Pichia pastoris,*" *Mol. Cell. Biol.*, 5(5):1111–1121 (1985).

Ernst, J.F., "Improved secretion of heterologous proteins by *Saccharomyces cerevisiae*: effects of promoter substitution in alpha–factor fusions," *DNA*, 5(6):483–491 (1986).

Gellerfors et al., "Isolation and characterization of a glycosylated form of human insulin–like growth factor I produced in *Saccharomyces cerevisiae,*" *J. Biol. Chem.*, 264(19):11444–11449 (1989).

Gleeson et al., "The methylotrohpic yeasts," *Yeast*, 4:1–15 (1988).

Jansen et al., "Sequence of cDNA encoding human insulin–like growth factor I precursor," *Nature*, 306:609–611 (1983).

Jones et al., "PEP4 gene function is required for expression of several vacuolar hydrolases in *Saccharomyces cerevisiae,*" *Genetics*, 102:665–677 (1982).

Komagata, K., in *Biology of Methylotrophs*, Goldberg et al., Eds. Butterworth–Heinemann, Ch. 2: Systematics of methylotrophic yeasts, pp. 25–37 (1991).

Kurtzman, C.P., "Synonomy of the yeast genera *Hansenula* and *Pichia* demonstrated through comparisons of deoxyribonucleic acid relatedness," *Antonie van Leeuwenhoek*, 50:209–217 (1984).

Nilsson et al., "Efficient secretion and purification of human insulin–like growth factor–1 with a gene fusion vector in *Staphylococci*," *Nuc. Acids Res.*, 13(4):1151 (1985).

Niwa et al., "Chemical synthesis, cloning, and expression of genes for human somatomedin C (insulin–like growth factor I) and $^{59}$Val–somatomedin C," *Ann. NY Acad. Sci.*, 469:31–52 (1986).

Peters et al., "Expression of a biologically active analogue of somatomedin–C/insulin–like growth factor I," *Gene*, 35:83–89 (1985).

Rinderknecht et al., "The amino acid sequence of human insulin–like growth factor I and its structural homology with proinsulin," *J. biol. Chem.*, 253(8):2769–2776 (1978).

Rose et al., "Structure and function of the yeast *URA3* gene: expression in *Escherichia coli*," *Gene*, 29:113–124 (1984).

Rothman et al., "Overproduction–induced mislocalization of a yeast vacuolar protein allows isolation of its structural gene," *Proc. Natl. Acad. Sci. USA*, 83:3248–3252 (1986).

Sudbery et al., "*Hansenula polymorpha* as a novel yeast system for the expression of hetrologous genes," *Biochem. Soc. Trans.*, 16:1081–1083 (1988).

Suzuki et al., "Yeast mutants with enhanced ability to secrete human lysozyme: isolation and identification of a protease–deficient mutant," *Mol. Gen. Genet.*, 219:58–64 (1989).

Trimble et al., "Structure of oligosaccharides on *Saccharomyces SUC2* invertase secreted by the methylotrophic yeast *Pichia pastoris*," *J. Biol. Chem.*, 266(34):22807–22817 (1991).

Woolford et al., "The PEP4 gene encodes an aspartyl protease implicated in the postranslational regulation of *Saccharomyces cerevisiae* vacuolar hydrolases," *Mol. Cell. Biol.*, 6(7):2500–2510 (1986).

Buckholz et al., "Yeast systems for the commercial production of heterologous proteins," *Bio/Technology* 9:1067–1072 (1991).

Shuster, J. R., in *Yeast Genetics Engineering*, Barr, et al. eds., Butterworth publishers, Ch.6: Regulated Transcriptional Systems for the Production of Proteins in Yeast: Regulation by Carbon Source, pp. 83–108 (1989).

FIRST AMINO ACID OF
MATURE IGF-1
↓
```
        M  G  P  E  T  L  C  G  A  E  L  V  D  A  L  Q
AAGCTTACCTGCCATGGGACCGGAGACGCTCTGCGGGGCTGAGCTCGTGGATGCTCTGCA
HindIIIBspMINcoI                        SacI         PstI
TTCGAATGGACGGTACCCTGGCCTCTGCGAGACGCCCCGACTCGAGCACCTACGAGACGT
        10        20        30        40        50        60

F  V  C  G  D  R  G  F  Y  F  N  K  P  T  G  Y  G  S  S  S
GTTCGTGTGTGGAGACAGGGGCTTTTATTTCAACAAGCCCACAGGGTATGGCTCCAGCAG

CAAGCACACACCTCTGTCCCCGAAAATAAAGTTGTTCGGGTGTCCCATACCGAGGTCGTC
        70        80        90       100       110       120

R  R  A  P  Q  T  G  I  V  D  E  C  C  F  R  S  C  D  L  R
TCGACGGGCGCCTCAGACAGGCATCGTGGATGAGTGCTGCTTCCGGAGCTGTGATCTAAG
SalI                                    BspMII
AGCTGCCCGCGGAGTCTGTCCGTAGCACCTACTCACGACGAAGGCCTCGACACTAGATTC
       130       140       150       160       170       180

R  L  E  M  Y  C  A  P  L  K  P  A  K  S  A  *  *
GAGGCTCGAGATGTATTGCGCACCCCTCAAGCCTGCCAAGTCAGCTTGATAAGGATCCGA
     AvaI                                            BamHI
CTCCGAGCTCTACATAACGCGTGGGGAGTTCGGACGGTTCAGTCGAACTATTCCTAGGCT
       190       200       210       220       230       240

ATTC
EcoRI
TAAG
```

FIG. 1

SEQUENCE LISTING ( 1 ) GENERAL INFORMATION:

( i i i ) NUMBER OF SEQUENCES: 17

( 2 ) INFORMATION FOR SEQ ID NO:1:

( i ) SEQUENCE CHARACTERISTICS:
      ( A ) LENGTH: 240 base pairs
      ( B ) TYPE: nucleic acid
      ( C ) STRANDEDNESS: double
      ( D ) TOPOLOGY: unknown ( i i ) MOLECULE TYPE: cDNA ( i x ) FEATURE:
      ( A ) NAME/KEY: CDS ( B ) LOCATION: 14..232

( x i ) SEQUENCE DESCRIPTION: SEQ ID NO:1:

```
AAGCTTACCT GCC ATG GGA CCG GAG ACG CTC TGC GGG GCT GAG CTC GTG          49
            Met Gly Pro Glu Thr Leu Cys Gly Ala Glu Leu Val
             1               5                      10

GAT GCT CTG CAG TTC GTG TGT GGA GAC AGG GGC TTT TAT TTC AAC AAG          97
Asp Ala Leu Gln Phe Val Cys Gly Asp Arg Gly Phe Tyr Phe Asn Lys
         15              20                  25

CCC ACA GGG TAT GGC TCC AGC AGT CGA CGG GCG CCT CAG ACA GGC ATC         145
Pro Thr Gly Tyr Gly Ser Ser Ser Arg Arg Ala Pro Gln Thr Gly Ile
         30              35              40

GTG GAT GAG TGC TGC TTC CGG AGC TGT GAT CTA AGG AGG CTC GAG ATG         193
Val Asp Glu Cys Cys Phe Arg Ser Cys Asp Leu Arg Arg Leu Glu Met
 45              50              55                          60

TAT TGC GCA CCC CTC AAG CCT GCC AAG TCA GCT TGA TAAGGATCCG              239
Tyr Cys Ala Pro Leu Lys Pro Ala Lys Ser Ala *
             65              70

A                                                                       240
```

( 2 ) INFORMATION FOR SEQ ID NO:2:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: unknown ( i i ) MOLECULE TYPE: DNA (genomic DNA)

( x i ) SEQUENCE DESCRIPTION: SEQ ID NO:2:

GTATCTTTGG ATAAAGAGG ACCGGAGACG CTCTGC          36

( 2 ) INFORMATION FOR SEQ ID NO:3:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: unknown ( i i ) MOLECULE TYPE: DNA (genomic DNA)

( x i ) SEQUENCE DESCRIPTION: SEQ ID NO:3:

ATAAAAGAGG ACCGGA          16

( 2 ) INFORMATION FOR SEQ ID NO:4:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: unknown ( i i ) MOLECULE TYPE: DNA (genomic DNA)

( x i ) SEQUENCE DESCRIPTION: SEQ ID NO:4:

AGTCAGCTTG ATAAGAATTC AAATGAGTCG ACCTGCAGGC          40

( 2 ) INFORMATION FOR SEQ ID NO:5:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: unknown ( i i ) MOLECULE TYPE: DNA (genomic DNA)

( x i ) SEQUENCE DESCRIPTION: SEQ ID NO:5:

TAAGAATTCA AATGAGT　　　　　　　　　　　　　　　　　　　　　　　　　　　17

( 2 ) INFORMATION FOR SEQ ID NO:6:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: unknown ( i i ) MOLECULE TYPE: DNA (genomic DNA)

( x i ) SEQUENCE DESCRIPTION: SEQ ID NO:6:

TCTTTGGATA AAGAGAGGCT GGACCGCAGA CGCTC　　　　　　　　　　　　　　　　35

( 2 ) INFORMATION FOR SEQ ID NO:7:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: unknown ( i i ) MOLECULE TYPE: DNA (genomic DNA)

( x i ) SEQUENCE DESCRIPTION: SEQ ID NO:7:

AAAAGAGAGG CTGGACCG　　　　　　　　　　　　　　　　　　　　　　　　　18

( 2 ) INFORMATION FOR SEQ ID NO:8:

( i ) SEQUENCE CHARACTERISTICS:
        ( A ) LENGTH: 33 base pairs
        ( B ) TYPE: nucleic acid
        ( C ) STRANDEDNESS: double
        ( D ) TOPOLOGY: unknown ( i i ) MOLECULE TYPE: DNA (genomic DNA)

( x i ) SEQUENCE DESCRIPTION: SEQ ID NO:8:

AATTCGATGA GATTTCCTTC AATTTTTACT GCA　　　　　　　　　　　　　　　　　33

( 2 ) INFORMATION FOR SEQ ID NO:9:

( i ) SEQUENCE CHARACTERISTICS:
        ( A ) LENGTH: 25 base pairs
        ( B ) TYPE: nucleic acid
        ( C ) STRANDEDNESS: double
        ( D ) TOPOLOGY: unknown ( i i ) MOLECULE TYPE: DNA (genomic DNA)

( x i ) SEQUENCE DESCRIPTION: SEQ ID NO:9:

GTAAAAATTG AAGGAAATCT CATCG　　　　　　　　　　　　　　　　　　　　25

( 2 ) INFORMATION FOR SEQ ID NO:10:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: unknown ( i i ) MOLECULE TYPE: DNA (genomic DNA)

( x i ) SEQUENCE DESCRIPTION: SEQ ID NO:10:

GACGTTCGTT TGTGCGGATC CAATGCGGTA GTTTAT　　　　　　　　　　　　　　　36

(2) INFORMATION FOR SEQ ID NO:11:

(i) SEQUENCE CHARACTERISTICS:
        (A) LENGTH: 14 base pairs
        (B) TYPE: nucleic acid
        (C) STRANDEDNESS: double
        (D) TOPOLOGY: unknown (ii) MOLECULE TYPE: DNA (genomic DNA)

(xi) SEQUENCE DESCRIPTION: SEQ ID NO:11:

```
CAGCAGATCT GCTG                                                        14
```

(2) INFORMATION FOR SEQ ID NO:12:

(i) SEQUENCE CHARACTERISTICS:
        (A) LENGTH: 14 base pairs
        (B) TYPE: nucleic acid
        (C) STRANDEDNESS: double
        (D) TOPOLOGY: unknown (ii) MOLECULE TYPE: DNA (genomic DNA)

(xi) SEQUENCE DESCRIPTION: SEQ ID NO:12:

```
CAGCAGATCT GCTG                                                        14
```

(2) INFORMATION FOR SEQ ID NO:13:

(i) SEQUENCE CHARACTERISTICS:
        (A) LENGTH: 21 base pairs
        (B) TYPE: nucleic acid
        (C) STRANDEDNESS: double
        (D) TOPOLOGY: unknown (ii) MOLECULE TYPE: cDNA (xi) SEQUENCE DESCRIPTION: SEQ ID NO:13:

```
CGCAGCATTC TTCGCATTAG C                                                21
```

(2) INFORMATION FOR SEQ ID NO:14:

(i) SEQUENCE CHARACTERISTICS:
        (A) LENGTH: 517 base pairs
        (B) TYPE: nucleic acid
        (C) STRANDEDNESS: double
        (D) TOPOLOGY: unknown (ii) MOLECULE TYPE: cDNA (ix) FEATURE:
        (A) NAME/KEY: CDS
        (B) LOCATION: 1..474

(xi) SEQUENCE DESCRIPTION: SEQ ID NO:14:

```
ACT GCA GTT TTA TTC GCA GCA TCC TCC GCA TTA GCT GCT CCA GTC AAC        48
Thr Ala Val Leu Phe Ala Ala Ser Ser Ala Leu Ala Ala Pro Val Asn
 1               5                  10                  15

ACT ACA ACA GAA GAT GAA ACG GCA CAA ATT CCG GCT GAA GCT GTC ATC        96
Thr Thr Thr Glu Asp Glu Thr Ala Gln Ile Pro Ala Glu Ala Val Ile
             20                  25                  30

GGT TAC TCA GAT TTA GAA GGG GAT TTC GAT GTT GCT GTT TTG CCA TTT       144
Gly Tyr Ser Asp Leu Glu Gly Asp Phe Asp Val Ala Val Leu Pro Phe
         35                  40                  45

TCC AAC AGC ACA AAT AAC GGG TTA TTG TTT ATA AAT ACT ACT ATT GCC       192
Ser Asn Ser Thr Asn Asn Gly Leu Leu Phe Ile Asn Thr Thr Ile Ala
     50                  55                  60

AGC ATT GCT GCT AAA GAA GAA GGG GTA TCT TTG GAT AAA AGA GAG GCT       240
```

|     |     |     |     |     |     |     |     |     |     |     |     |     |     |     |     |
|-----|-----|-----|-----|-----|-----|-----|-----|-----|-----|-----|-----|-----|-----|-----|-----|
| Ser | Ile | Ala | Ala | Lys | Glu | Glu | Gly | Val | Ser | Leu | Asp | Lys | Arg | Glu | Ala |
| 65  |     |     |     | 70  |     |     |     |     | 75  |     |     |     |     | 80  |     |

| GAA | GCT | TGG | CAT | TGG | TTG | CAA | CTA | AAA | CCT | GGC | CAA | CCA | ATG | TAC | AAG | 288 |
|-----|-----|-----|-----|-----|-----|-----|-----|-----|-----|-----|-----|-----|-----|-----|-----|-----|
| Glu | Ala | Trp | His | Trp | Leu | Gln | Leu | Lys | Pro | Gly | Gln | Pro | Met | Tyr | Lys |     |
|     |     |     |     | 85  |     |     |     |     | 90  |     |     |     |     | 95  |     |     |

| AGA | GAA | GCC | GAA | GCT | GAA | GCT | TGG | CAT | TGG | CTG | CAA | CTA | AAG | CCT | GGC | 336 |
|-----|-----|-----|-----|-----|-----|-----|-----|-----|-----|-----|-----|-----|-----|-----|-----|-----|
| Arg | Glu | Ala | Asp | Ala | Glu | Ala | Trp | His | Trp | Leu | Gln | Leu | Lys | Pro | Gly |     |
|     |     |     | 100 |     |     |     |     | 105 |     |     |     |     | 110 |     |     |     |

| CAA | CCA | ATG | TAC | AAA | AGA | GAA | GCC | GAC | GCT | GAA | GCT | TGG | CAT | TGG | CTG | 384 |
|-----|-----|-----|-----|-----|-----|-----|-----|-----|-----|-----|-----|-----|-----|-----|-----|-----|
| Gln | Pro | Met | Tyr | Lys | Arg | Glu | Ala | Asp | Ala | Glu | Ala | Trp | His | Trp | Leu |     |
|     |     | 115 |     |     |     |     | 120 |     |     |     |     | 125 |     |     |     |     |

| CAA | CTA | AAG | CCT | GGC | CAA | CCA | ATG | TAC | AAA | AGA | GAA | GCC | GAC | GCT | GAA | 432 |
|-----|-----|-----|-----|-----|-----|-----|-----|-----|-----|-----|-----|-----|-----|-----|-----|-----|
| Gln | Leu | Lys | Pro | Gly | Gln | Pro | Met | Tyr | Lys | Arg | Glu | Ala | Asp | Ala | Glu |     |
|     | 130 |     |     |     |     | 135 |     |     |     |     | 140 |     |     |     |     |     |

| GCT | TGG | CAT | TGG | TTG | CAG | TTA | AAA | CCC | GGC | CAA | CCA | ATG | TAC | TAA | GCC | 480 |
|-----|-----|-----|-----|-----|-----|-----|-----|-----|-----|-----|-----|-----|-----|-----|-----|-----|
| Ala | Trp | His | Trp | Leu | Gln | Leu | Lys | Pro | Gly | Gln | Pro | Met | Tyr |     |     |     |
| 145 |     |     |     |     | 150 |     |     |     |     | 155 |     |     |     |     |     |     |

CGACTGATAA CAACAGTGTA GATGTAACAA AGTCGAC 517

(2) INFORMATION FOR SEQ ID NO:15:

(i) SEQUENCE CHARACTERISTICS:
        (A) LENGTH: 138 base pairs
        (B) TYPE: nucleic acid
        (C) STRANDEDNESS: double
        (D) TOPOLOGY: unknown (ii) MOLECULE TYPE: cDNA (ix) FEATURE:
        (A) NAME/KEY: CDS
        (B) LOCATION: 1..135

(xi) SEQUENCE DESCRIPTION: SEQ ID NO:15:

| ATG | TAC | GCA | GAC | GCT | ATC | TTT | ACT | AAC | TCT | TAC | CGT | AAA | GTT | CTG | GGC | 48  |
|-----|-----|-----|-----|-----|-----|-----|-----|-----|-----|-----|-----|-----|-----|-----|-----|-----|
| Met | Tyr | Ala | Asp | Ala | Ile | Phe | Thr | Asn | Ser | Tyr | Arg | Lys | Val | Leu | Gly |     |
| 1   |     |     |     | 5   |     |     |     |     | 10  |     |     |     |     | 15  |     |     |

| CAG | CTG | TCT | CGA | CGC | AAG | CTT | CTG | CAG | GAT | ATC | ATG | TCT | AGA | CAG | CAG | 96  |
|-----|-----|-----|-----|-----|-----|-----|-----|-----|-----|-----|-----|-----|-----|-----|-----|-----|
| Gln | Leu | Ser | Arg | Arg | Lys | Leu | Leu | Gln | Asp | Ile | Met | Ser | Arg | Gln | Gln |     |
|     |     |     | 20  |     |     |     |     | 25  |     |     |     |     | 30  |     |     |     |

| GGC | GAA | TCT | AAC | CAG | GAG | CGT | GGC | GCC | CGT | GCA | CGC | CTG | TAG | 138 |
|-----|-----|-----|-----|-----|-----|-----|-----|-----|-----|-----|-----|-----|-----|-----|
| Gly | Glu | Ser | Asn | Gln | Glu | Arg | Gly | Ala | Arg | Ala | Arg | Leu |     |     |
|     |     | 35  |     |     |     |     | 40  |     |     |     |     | 45  |     |     |

(2) INFORMATION FOR SEQ ID NO:16:

(i) SEQUENCE CHARACTERISTICS:
        (A) LENGTH: 21 base pairs
        (B) TYPE: nucleic acid
        (C) STRANDEDNESS: double
        (D) TOPOLOGY: unknown (ii) MOLECULE TYPE: cDNA (xi) SEQUENCE DESCRIPTION: SEQ ID NO:16:

AGCTCCTGCA GGATATCCTG T 21

(2) INFORMATION FOR SEQ ID NO:17:

(i) SEQUENCE CHARACTERISTICS:
        (A) LENGTH: 20 base pairs
        (B) TYPE: nucleic acid
        (C) STRANDEDNESS: double
        (D) TOPOLOGY: unknown (ii) MOLECULE TYPE: cDNA ( x i ) SEQUENCE DESCRIPTION: SEQ ID NO:17:

AGCTTACGCA GACGCTATCT 20

PRODUCTION OF INSULIN-LIKE GROWTH FACTOR-1 IN METHYLOTROPHIC YEAST CELLS

RELATED APPLICATIONS

This is a continuation of application Ser. No. 07/983,523, filed Mar. 3, 1993, now abandoned, which is a 371 of International Application No. PTC/U591/06452, filed Sep. 4, 1991, which application is a continuation-in-part of U.S. application Ser. No. 07/578,728, now abandoned to Brierley et filed Sep. 4, 1990, "PRODUCTION OF INSULIN-LIKE GROWTH FACTOR-1 IN METHYLOTROPHIC YEAST CELLS"now abandoned. The subject matter of this application is also related to U.S. application Ser. No. 07/678,916, to Gleason et al , filed Apr. 1, 1991, "GENES WHICH INFLUENCE *PICHIA PASATORIS* PROTEOLYTIC ACTIVITY, AND USES THEREFOR". application Ser. Nos. 07/578,728 and 07/678,916 which has been abandoned in favor of continuation application 08/088,633, filed Jul. 6, 1993 now U.S. Pat. No. 5,324,660, are incorporated herein in their entirety by reference thereto.

FIELD OF THE INVENTION

The invention described herein relates to processes for producing authentically folded biologically active insulin-like growth factor-1 (IGF-1) using methylotrophic yeast host cells, such as *Pichia pastoris* (*P. pastoris*). The invention further relates to the methylotrophic yeast that produce IGF-1, to DNA fragments for preparing expression vectors that include DNA encoding IGF-1 and that are used for transforming the methylotrophic yeast cells, to the expression vectors, and to cultures containing the transformed yeast cells.

BACKGROUND OF THE INVENTION

Insulin-like growth factor-1 belongs to a heterogeneous family of peptides which share some of the biological and chemical properties of insulin, but which are antigenically distinct from insulin. Currently available experimental evidence suggests that IGF-1 promotes growth by mediating the effects of growth hormone. Thus, such processes as skeletal growth, call replication and other growth related processes are affected by IGF-1 levels. Physiological concentrations of IGF-1 have been shown to be influenced by such conditions as thyroid disease, diabetes and malnutrition (see Preece (1983) *Horm. Blood,* 4: 108). IGF-1 has also been shown to act synergistically with other growth factors, for example, in accelerating the healing of soft and mesenchymal tissue wounds (see Lynch et al. (1989) *J. Clin., Periodontol,* 16: 545; and Lynch et al. (1987) *Proc. Nat. Acad. Sci. USA,* 84: 7696), and in enhancing the growth of mammalian cells in serum-free tissue culture medium (see Burleigh et al. (1986) *American Biotech. Lab.,* 4: 48).

Considering the many clinical and research applications of IGF-1, a ready supply of IGF-1 would be of great value to the medical and biotechnology fields. Since isolation from natural sources is technically difficult, expensive, and time consuming, recent efforts have centered on the development of efficient recombinant methods for the production of IGF-1.

Among host cells that have been used for the production of heterologous proteins, *E. coli* and *Saccharomyces cerevisiae* (Baker's yeast) are probably the best characterized. Insulin-like growth factor-1 (IGF-1), which is a polypeptide of 70 amino acids with a molecular weight of 7648 daltons, is a single chain protein that has three intrachain disulfide bridges. These disulfide bonds, along with numerous hydrogen bonds and hydrophilic interactions, maintain the compact tertiary structure of this molecule. *E. coli,* however, does not possess the ability to produce disulfide bonds in proteins, so that proteins, such as IGF-1, that include disulfide bonds, when cloned into and expressed in *E. coli,* frequently are not stable and tend to aggregate into inactive complexes. In addition, IGF-1 produced in *E. coli* has to be extracted and treated with oxidizing agents to produce the disulfide bonds. Upon reduction and reoxidation, IGF-1 refolds in a variety of ways, forming as many as 15 monomeric configurations (Meng et al. (1988) *J. Chrom.,* 443: 183) because cell breakage and too rapid formation of disulfide linkages results in random disulfide bond formation. In order to produce biologically active IGF-1, the resulting mixture of 15 different forms of IGF-1 must be separated. Consequently, the yield of purified product is very low (Grossgian (1985) *Gene,* 18: 199).

Furthermore, since *E. coli* is a prokaryote, in order to produce IGF-1 molecules which contain the authentic N-terminal glycine, and not the initiating methionine present on the primary translation product, it is necessary to express IGF-1 in *E. coli* as a fusion protein. Cleavage of mature IGF-1 from the initially produced fusion protein necessitates an additional step in the production process. Consequently, attempts to produce this peptide by recombinant means in *E. coli* host expression systems results in a complex mixture of product forms which must be separated for further use (see, Grossgian (1985) *Gene,* 18: 199).

Eukaryotic host cells, including yeast cells, thus, are the host cells of choice for the expression of many eukaryotic proteins. Yeast host cells offer clear advantages over bacteria in the production of heterologous proteins, including their ability to properly process pre-pro-heterologous proteins and secrete heterologous proteins into the culture medium. Secretion of proteins from cells is often superior to production of proteins in the cytoplasm because secreted products are obtained in a higher degree of initial purity and further purification of the secreted products is made easier by the absence of cellular debris. In addition, the secretory pathway of the cell and the extracellular medium tend to be oxidizing environments which support disulfide bond formation necessary for proper folding of many proteins (Smith, et al, (1985) *Science* 229: 1219); whereas, the cytoplasm is a reducing environment in which disulfide bonds do not form. Thus, for production of sulfhydryl-rich proteins that rely on disulfide bonds to maintain the correct tertiary structures, there is a compelling need to develop eukaryotic hosts capable of secreting such proteins into the culture medium. Therefore, production of sulfhydryl-rich proteins, such as IGF-1, that contain appropriately formed disulfide bonds, can best be achieved by transit through the secretory pathway.

IGF-1 has been cloned into and expressed using *S. cerevisiae* host cells by introducing DNA encoding IGF-1 on autonomously replicating extrachromosomal elements. Gellerfors et al. ((1989) *J. Biol, Chem.,* 264: 11444–11449) describes the production of IGF-1 in *S. cerevisiae* under the control of the *S. cerevisiae* actin promoter. The IGF-1 product is encoded by autonomously replicating plasmid-borne DNA. In a similar study, Bayne et al. ((1988) *Gene* 66: 235–244) describes the production of IGF-1 in *S. cerevisiae* under the control of the *S. cerevisiae* alpha mating factor promoter. The latter, however, reports yields of IGF-1 of only about 2 mg of IGF-1 per liter of fermentation broth.

In view of this low yield and the problems generally encountered with up-scaling the production of heterologous proteins in autonomous plasmid-based yeast systems, such as loss of selection for plasmid maintenance and problems concerning plasmid distribution, copy number and stability in fermentors operated at high cell density, there is a need to develop more efficient means for producing large quantities of biologically active IGF-1.

Therefore, it is an object of this invention to provide host cells and expression vectors that stably express IGF-1 and that secrete high concentrations of biologically active IGF-1.

It is another object of this invention to provide an expression system for the production of biologically active IGF-1 that, not only secretes high concentrations of biologically active IGF-1, but that can be readily scaled up to produce large quantities of such IGF-1.

SUMMARY OF THE INVENTION

Expression systems and methods using the expression systems for the production of biologically active insulin-like growth factor-1 (IGF-1) using methylotrophic yeast host cells are provided. The methods of production are readily scaled up from shake-flask cultures to large scale fermentors with no loss in IGF-1 productivity and without the need for making major changes in the fermentation conditions used for the growth of the transformed strains. Methods for isolation and purification of the IGF-1 product are also provided.

The expression systems and methods provided herein avoid the problems encountered with heterologous protein expression in *S. cerevisiae* in which high level expression can only be achieved by the introduction of multicopy plasmids into the host cells.

The expression system described herein uses methylotrophic yeast host cells, such as for example, *P. pastoris*, for the expression of IGF-1. Key features of the system include the ability to stably integrate and express multiple copies of the DNA encoding IGF-1 and the DNA encoding the signals that direct secretion and processing of the IGF-1 and the ability to properly process mature IGF-1 from the expressed precursor form of IGF-1 and to secrete the resulting mature IGF-1 product.

Another feature of the system resides in selection of the promoter that has been used to control expression of the DNA encoding IGF-1. The promoter, which is derived from a methanol-responsive gene, such as AOX1, of a methylotrophic yeast, is tightly regulated and provides for high-level regulated expression of genes placed under its control (see, e.g., European Patent Application No. 85113737.2, published Jun. 4, 1986, under No. 0 183 071, now issued in the United States as U.S. Pat. No. 4,855,231).

Expression and secretion of high levels of IGF-1 peptide has been accomplished by transforming a methylotrophic yeast host with a DNA construct that contains at least one copy, but may contain as many as six or more copies, of DNA encoding an IGF-1 peptide in which the DNA is operably linked with DNA encoding a signal sequence that is effective for directing the processing and secretion of the IGF-1 peptide product. The DNA construct also includes a promoter region, which directs expression of the DNA encoding the signal sequence and IGF-1 peptide, and a transcription terminator functional in a methylotrophic yeast.

The DNA construct provided here, also includes sequences of nucleotides that have sufficient homology with a target gene in the methylotrophic yeast host cell genome to effect stable integration. Integration takes place by addition or replacement at the site of the target gene. Alternatively, the DNA construct is provided as part of a circular plasmid that integrates by addition at a site of homology between the host and the plasmid.

In accordance with other embodiments, expression vectors containing the DNA construct, which includes at least one copy of an expression cassette, are provided.

According to another aspect, there are provided methylotrophic yeast cells containing in their genome at least one copy of the above-described DNA fragment. In preferred embodiments, the cells are deficient in one or more proteases that are not essential for proper cleavage of the precursor form of IGF-1.

In preferred embodiments, the host cell is *P. pastoris*, the promoter is the AOX1 promoter, and the signal sequence is the *S. cerevisiae* alpha-mating factor (αMF) pre-pro sequence, which includes a processing sequence of the formula lys-arg-(glu-ala)$_x$ in which x is preferably between 0 and 3. Methylotrophic yeast cells in which at least one copy of this DNA construct has been introduced efficiently produce and secrete biologically active IGF-1 peptides into the medium. In preferred embodiments, IGF-1 has been very efficiently produced in and secreted from the methylotrophic yeast *P. pastoris*.

The polypeptide product produced by the methylotrophic host cells is secreted into the culture medium at high concentrations; the level of IGF-1 peptides that are secreted is many times the concentrations that are reported for the secretion of IGF-1 from *S. cerevisiae* (see, e.g., Bayne et al. (1988) *Gene*, 66: 235–244). The IGF-1 peptides are produced by methylotrophic yeast cells that contain one or more integrated copies of DNA encoding IGF-1 peptides operably linked with DNA encoding a signal sequence, such as the *S. cerevisiae* α-mating factor (αMF) pre-pro sequence that includes at least one site, such as lys-arg, that is sufficient for proper proteolytic cleavage of mature IGF-1 from the pre-pro-protein, under the regulation of a promoter region of a methanol-responsive gene of a methylotrophic yeast. In addition, the DNA encoding the signal sequence may encode one or more glu-ala sequences, which also serve to direct proper processing. The number of glu-ala sequences is preferably from 0 to 3, but may include more copies. The number of copies is limited by the ability of the selected host to properly process the pre-pro-protein.

According to a still further embodiment, there is provided a process for producing IGF-1 peptides by growing methylotrophic yeast transformants containing in their genome at least one copy of a DNA sequence operably encoding an IGF-1 peptide, operably associated with DNA encoding the *S. cerevisiae* αMF pre-pro sequence. This pre-pro sequence includes a lys-arg processing site and may also include from 0 to 3 glu-ala spacer segments. Transcription of the DNA encoding the signal and the DNA encoding the IGF-1 peptide is under the regulation of a promoter region of a methanol-responsive gene of a methylotrophic yeast. Under conditions that induce the promoter, transcription of the DNA is induced, thereby resulting in expression and processing of the precursor IGF-1, and, ultimately, secretion of IGF-1 peptides into the culture medium.

Cultures of viable methylotrophic yeast cells capable of producing IGF-1 peptides are also provided. In preferred embodiments, the yeast host cells that express and secrete IGF-1 have been modified by disruption of one or more host cell genes that directly or indirectly influence host cell protease expression. This disruption results in a reduction of some protease activities of the host cell, for example, proteinase A and carboxypeptidase Y activities.

A preferred process for recovering and purifying IGF-1 peptides from *P. pastoris* fermentation broth is described in U.S. patent application Ser. No. 07/641,430. The preferred form of IGF-1 is a polypeptide product which exhibits substantially the same biological activities as natural insulin-like growth factor-1, as measured in recognized bioassays (see, e.g., Takano et al. (1976) *Acta Endocr.* 82: 449–459; Schoenle et al. (1982) *Nature* 296: 252–253; Copeland et al. (1983) *Am. J. Primatology:* 161–169 and Buul-Offers et al. (1986) *Ped. Res.* 20: 825–827) having substantially the same amino acid sequence as native IGF-1, Sequence ID No. 1, in the sequence listings. It is understood that polypeptides having some variation in amino acid sequences such as lacking one or more amino acids, or containing additional amino acids, or having some substituted amino acids are within scope of the invention, provided that these peptides exhibit the functional activity of IGF-1 according to known bioassays. Such IGF-1 may include, not only authentically folded IGF-1, but also the misfolded and multimeric forms of IGF-1 that exhibit the ability to detectably bind to IGF-1 receptors and that demonstrate at least one bioactivity associated with IGF-1. In addition, biologically inactive forms may be converted to active forms by reduction and oxidation.

BRIEF DESCRIPTION OF THE FIGURES

FIG. 1 provides the nucleotide sequence of a synthetic insulin-like growth factor gene.

DETAILED DESCRIPTION OF THE INVENTION

Figure 2:
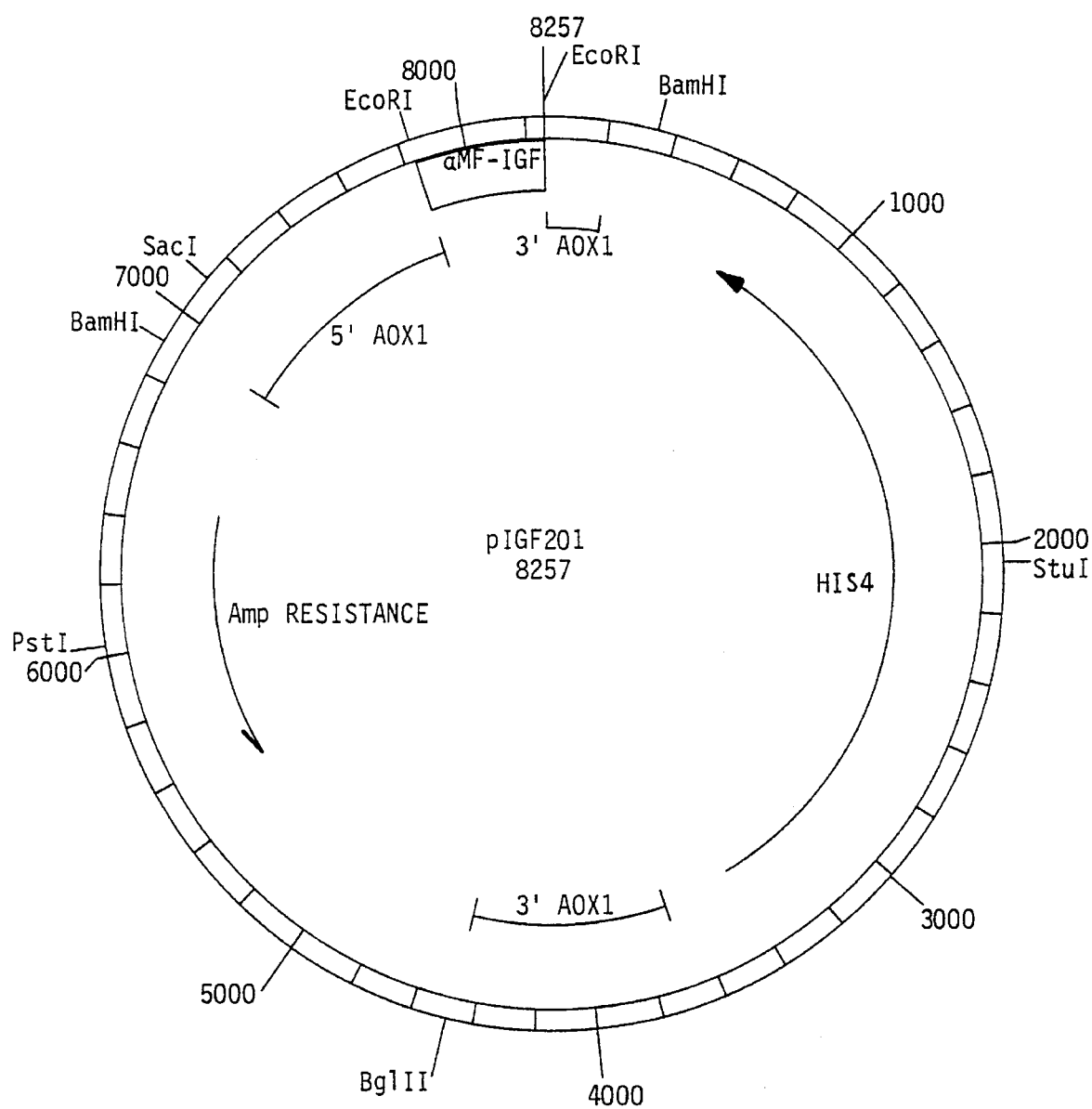
FIG. 2 is a restriction map of plasmid pIGF201.

Definitions:

Unless defined otherwise, all technical and scientific terms used herein have the same meaning as is commonly understood by one of skill in the art to which this invention belongs. All publications mentioned herein are incorporated by reference thereto. All U.S. patents mentioned herein are incorporated in their entirety by reference thereto.

As used herein, IGF-1 or an IGF-1 peptide is intended to include all the allelic variations of IGF-1. Moreover derivatives obtained by simple modification of the amino acid sequence of the naturally occurring product, such as by way of site-directed mutagenesis or other standard procedures, are included within the scope of the present invention. Forms of IGF-1 that exhibit similar biological activities to naturally occurring IGF-1 are also encompassed by the present invention. IGF-1 is intended to encompass all forms of IGF-1 present in the culture medium. Such IGF-1 may be a mixture of several different three-dimensional forms. In addition to authentic IGF-1, which is the intact, the monomeric, correctly folded material, other forms may be present in the extracellular medium of the host cells that express IGF-1, such as misfolded proteins, multimeric forms such as dimers, and trimers. It is intended that the IGF-1 peptide, as used herein, includes any peptide that has the ability to bind to IGF-1 receptors and that exhibits at least one activity, such as the ability to promote cell proliferation or cell growth in a standard activity assay, that is associated with the biological activity of IGF-1 (see, e.g., Takano et al. (1976) *Acta Endocr.* 82: 449–459; Schoenle et al. (1982) *Nature* 296: 252–253; Copeland et al. (1983) *Am. J. Primatology* 5: 161–169 and Buul-Offers et al. (1986) *Ped.Res.* 20: 825–827).

As used herein, an IGF-1 peptide that has biological activity is a peptide that specifically binds to IGF-1 receptors, as detected by a standard assay, and that exhibits a biological activity associated with IGF-1 as measured in a recognized assay. Such assays are known to those of skill in this art.

As used herein, authentic IGF-1 refers to IGF-1 that includes disulfide bonds as they exist in naturally-occurring IGF-1. Authentic IGF-1 may be efficiently recovered and purified from *P. pastoris* fermentation broth.

As used herein, mature IGF-1 refers to processed IGF-1 from which the signal and processing sequences have been cleaved. Mature IGF-1 includes authentic IGF-1 and any other forms of processed IGF-1 that are secreted into the medium. IGF-1 is intended to encompass peptides that have the ability to bind to IGF-1 receptors and to promote cell growth or proliferation as measured by any means known to those of skill in the art.

As used herein, pre-pro-IGF-1 refers to a polypeptide that includes a leader or signal sequence that effects secretion of mature IGF-1 into the extracellular space of said host and one or more processing signals that direct processing of the pre-pro-IGF-1 to produce the mature IGF-1. As used herein, secreted IGF-1 refers to processed IGF-1 that does not include the signal or leader sequence. Processed IGF-1 or processed protein refer to IGF-1 or protein from which the leader signal has been cleaved.

As used herein, a signal or leader sequence, which expressions are used interchangeably, refers to a sequence of amino acids that effects transport of a linked polypeptide through the cell membrane. A signal sequence refers to a sequence of hydrophobic amino acids at the amino terminus of the protein to which it is linked. DNA encoding a signal sequence is located downstream (3' in the direction of transcription) from the ATG start codon and upstream (5') from the DNA that encodes the structural gene. In addition, the signal sequence includes one or more processing sites, sequences of amino acids that are recognized by one or more host cell proteases, interposed between the signal sequence and the protein. Cleavage by a host cell protease effects removal of the signal sequence. The signal sequence, processing sites and protein are referred to as a pre-pro-protein.

The signal sequences and processing sites contemplated for use herein are those that effect transport of IGF-1 through the cellular membrane of a methylotrophic yeast host cell, such as *P. pastoris*. In preferred embodiments the signal sequence and processing sites, lys-arg and (glu-ala)$_x$, in which x is an integer, preferably between 0 and 3, are derived from the *S. cerevisiae* αMF gene. Any signal sequence and processing site known to those of skill in the art that are effective for secreting mature IGF-1 into the extracellular space of a methylotrophic host may be used. In preferred embodiments, the signal sequences are selected so that fermentation cultures of methylotrophic host cells that have a cell density of about 300 g/L secrete at least about 9 mg/L of authentic IGF-1 into the broth. To select suitable signal sequences, DNA constructs encoding a signal sequence and processing site(s) linked to DNA encoding IGF-1 may be prepared and introduced into the genome of a methylotrophic host by methods known to those of skill in the art or described herein and tested for their ability to direct secretion of mature IGF-1 into the medium. Any signal sequence that leads to secretion of relatively high concentrations, preferably more than 10 mg/ml of mature IGF-1, is contemplated for use herein.

As used herein, heterologous DNA includes DNA that does not occur naturally as part of the genome in which it is present or which is found in a location or locations in the genome that differs from that in which it occurs in nature. Heterologous DNA is generally not endogenous to the cell into which it is introduced, but has been obtained from another cell. Generally, although not necessarily, such DNA encodes RNA and proteins that are not normally produced by the cell in which the DNA or RNA is expressed. Heterologous DNA may also be referred to as foreign DNA. Any DNA that one of skill in the art would recognize or consider as heterologous or foreign to the cell in which is expressed is herein encompassed by heterologous DNA. Examples of heterologous DNA include, but are not limited to, DNA that encodes IGF-1, transcriptional and translational regulatory sequences, and selectable or traceable marker proteins, such as a protein that confers drug resistance.

As used herein, expression cassette refers to a DNA construct that includes sequences functional for both the expression and the secretion of IGF-1. Accordingly, an expression cassette includes DNA encoding a promoter region, DNA encoding a transcription terminator region, and sequences sufficient for translation, secretion and proper processing of the expressed peptide. In addition, in preferred embodiments, the expression cassette is on a fragment that includes sequences at 5' and 3' ends that are homologous to a target locus in the host cell genome, whereby, upon introduction into the host cell, the expression cassette is stably integrated into the host cell genome.

As used herein, the term DNA construct embraces expression cassettes and also includes DNA fragments that include more than one expression cassette.

As used herein, the term operative linkage or operably associated refers to the relationship among elements of a DNA construct in which the elements are arranged whereby regulatory sequences of nucleotides that are part of the construct directly or indirectly control expression of the DNA in the construct, including DNA encoding a protein or a peptide.

As used herein, the term "a DNA fragment operably encoding IGF-1 peptides" includes DNA fragments encoding IGF-1 or any other "IGF-1 peptide" as defined hereinabove. DNA encoding IGF-1 is known in the art and may be obtained by chemical synthesis or by transcription of messenger RNA (mRNA) corresponding to IGF-1 into complementary DNA (cDNA) and converting the latter into a double stranded cDNA. Chemical synthesis of a gene for human IGF-1 is, for example, disclosed by Niwa et al. (1986) *Annals of the NY Academy of Science*, 469: 31–52, and Buell et al. (1985) *Nucleic Acids Research*, 13: 1923–1938. The requisite DNA sequence can also be removed, for example, by restriction enzyme digestion of known vectors harboring the IGF-1 gene. Examples of such vectors and the means for their preparation are well known to those of skill in the art. See, e.g., Niwa et al. (1986) *Annals of the NY Academy of Science*, 469: 31–52, and Buell et al. (1985) *Nucleic Acids Research*, 13: 1923–1938. The nucleotide sequence of a presently preferred IGF-1 gene is illustrated in FIG. 1 and is further elucidated in the examples.

As used herein, the term expression vector is intended to include vectors capable of expressing DNA that are in operational association with other sequences capable of effecting their expression, such as promoter sequences, in a selected host cell. In general, expression vectors usually used in recombinant DNA technology are often in the form of "plasmids" which are circular, double-stranded DNA loops, extrachromosomal elements.

As used herein, the terms "vector" and "plasmid" are used interchangeably and are not intended to be limited, but to include any expression vectors or means that permit heterologous DNA to be expressed in a particular host cell.

As used herein, the term "culture" means a propagation of cells in a medium conducive to their growth, and all subcultures thereof. The term "subculture" refers to a culture of cells grown from cells of another culture (source culture), or any subculture of the source culture, regardless of the number of times subculturing has been performed between the subculture of interest and the source culture.

The amino acids which occur in the various sequences of amino acid set forth in the specification have their usual, three- and one-letter abbreviations, routinely used in the art:

| Amino Acid | Abbreviation | |
|---|---|---|
| L-Alanine | Ala | A |
| L-Arginine | Arg | R |
| L-Asparagine | Asn | N |
| L-Aspartic acid | Asp | D |
| L-Cysteine | Cys | C |
| L-Glutamine | Gln | Q |
| L-Glutamic Acid | Glu | E |
| L-Glycine | Gly | G |
| L-Histidine | His | H |
| L-Isoleucine | Ile | I |
| L-Leucine | Leu | L |
| L-Lysine | Lys | K |
| L-Methionine | Met | M |
| L-Phenylalanine | Phe | F |
| L-Proline | Pro | P |
| L-Serine | Ser | S |
| L-Threonine | Thr | T |
| L-Tryptophan | Trp | W |
| L-Tyrosine | Tyr | Y |
| L-Valine | Val | V |

Host cells.

Yeast species contemplated for Use herein are methylotrophic yeast that are able to grow on methanol as a carbon source. Species intended for use herein have the biochemical pathways necessary for methanol utilization and fall into four genera, Candida, Hansenula, Pichia, and Torulopsis. A substantial amount is known about the molecular biology of members of the species *Hansenula polymorpha* and *Pichia Pastoris*.

*P. pastoris* is the presently preferred yeast species. *P. pastoris* is a known industrial yeast strain that is capable of efficiently utilizing methanol as the sole carbon and energy source.

DNA constructs.

The DNA constructs and expression cassettes used for transforming methylotrophic yeast cells contain a methanol-responsive promoter from a methylotrophic yeast gene, DNA encoding IGF-1 (IGF-1 gene), DNA encoding a signal sequence in-reading frame with the gene, and and a transcription terminator functional in a methylotrophic yeast. The signal sequence may be any such sequence that functions to direct the secretion from and proper processing of IGF-1 in the yeast host cell. The *S. cerevisiae* αMF pre-pro sequence is the preferred signal sequence. The αMF pre-pro sequence includes a DNA sequence encoding a processing sequence lys-arg, and (glu-ala)$_x$ spacer sequences in which x is 0, 1, 2 or 3.

The *S. cerevisiae* alpha-mating factor is a 13-residue peptide, secreted by cells of the "alpha" mating type, that acts on cells of the opposite "a" mating type to promote efficient conjugation between the two cell types and thereby formation of "a-alpha" diploid cells (Thorner et al. (1981) *The Molecular Biology the Yeast Saccharomyces*, Cold Spring Harbor Laboratory, Cold Spring Harbor, N.Y., 143). The α-factor is synthesized as a 165 amino acid long precursor that contains an 83 residue leader and four α-factor peptide regions. Each region is preceded by short spacer peptides of sequences:lys-arg-glu-ala-asp-ala-glu-ala; lys-arg-(glu-ala)$_3$ or lys-arg-(glu-ala)$_2$. The leader and spacer includes the amino acid sequences for proteolytic processing and secretion (see, e.g., Brake et al., *Proc. Natl. Acad. Sci. USA*, 81: 4642 (1984)).

There are a number of methanol-responsive genes in methylotrophic yeast. The expression of each is controlled by methanol-responsive regulatory regions, also referred to as promoters. Any of such methanol-responsive promoters are suitable for use in the DNA constructs. Examples of specific regulatory regions include, but are not limited to, the promoter for the primary alcohol oxidase gene from Pichia pastoris AOX1, the promoter for the secondary alcohol oxidase gene from *P. pastoris* AOX2, the promoter for the dihydroxyacetone synthase gene (DAS) from *P. pastoris*, the promoter for the P40 gene from *P. pastoris* the promoter for the catalase gene from *P. pastoris*. Selection of suitable promoter regions and other regulatory regions is, in light of this disclosure, within the level of skill in the art.

The presently preferred promoter region employed to drive IGF-1 gene expression is derived from a methanol-regulated alcohol oxidase gene of *P. pastoris*. *P. pastoris* expresses two functional alcohol oxidase genes: alcohol oxidase I (AOX1) and alcohol oxidase II (AOX2) genes. The coding portions of the two AOX genes are closely homologous at both the DNA and the predicted amino acid sequence levels and share common restriction sites. The proteins expressed from the two genes have similar enzymatic properties but the promoter of the AOX1 gene is more efficient and provides for higher levels of gene expression; therefore, its use is preferred for IGF-1 expression. The AOX1 gene, including its promoter, has been isolated and thoroughly characterized (see, Ellis et al. (1985) *Mol. Cell. Biol.* 5: 1111 and U.S. Pat. No. 4,855,231).

The DNA construct that is introduced into methylotrophic yeast cells contains, in addition to a methanol-responsive promoter of a methylotrophic yeast gene, DNA encoding IGF-1, DNA encoding an in-reading frame signal and processing sequence, and a transcription terminator functional in a methylotrophic yeast. The transcription terminator functional in a methylotrophic yeast intended for use herein has either (a) a subsegment that encodes a polyadenylation signal and polyadenylation site in the transcipt, and/or (b) a subsegment that provides a transcription termination signal for transcription from the promoter used in the expression cassette. The entire transcription terminator may be obtained from a protein-encoding gene that may be the same or different from the gene that is the source of the promoter.

The DNA construct may also contain a selectable marker gene. For this purpose, any selectable marker gene functional in methylotrophic yeast may be employed, including, but not limited to, any gene which confers a selectable phenotype upon methylotrophic yeast permitting such yeast cells to be identified and selectively grown from among a vast majority of untransformed cells. Appropriate selectable marker systems, for example, would be an auxotrophic mutant *P. pastoris* host strain and a wild type biosynthetic gene which complements the host's defect. For example, the *S. cerevisiae* or *P. pastoris* HIS4 gene maybe used to complement His4⁻*P. pastoris* strains, or the *S. cerevisiae* ARG4 gene or the *P. pastoris* ARG4 gene maybe employed to complement Arg4⁻ mutants.

In addition, the DNA constructs may additionally include selectable marker genes that are functional in bacteria. Thus, any gene can be used which confers a phenotype on bacteria that allows transformed bacterial cells to be identified and selectively grown from among a vast majority of untransformed cells. This additional selectable marker permits such DNA to be introduced into and amplified in bacterial host cells, such as *E. coli*. Suitable selectable marker genes include the ampicillin resistance gene (Ampr), tetracycline resistance gene (Tc$^r$) and the like.

The DNA construct may include sequences allowing for replication and selection in bacteria, especially *E. coli*. In particular, the DNA construct may be inserted into a plasmid or it may be circularized to form a plasmid that includes sequences for replication and extrachromosomal maintenance in bacteria. In this way, large quantities of the DNA fragment can be produced by replication in bacteria. When such amplification is desired, the DNA construct should include a bacterial origin of replication to ensure the maintenance of the DNA construct from generation to generation of the bacteria. Exemplary bacterial origins of replication include the fl-ori, colisin, col E1, and others that are known to or that can be identified by those of skill in the art.

The DNA construct may include multiple copies of the DNA encoding IGF-1 operatively linked to the signal and processing signals, and other transcriptional regulatory signals, i.e., the DNA construct may include multiple copies of the expression cassette.

Transformation of methylotrophic yeast host cells with the DNA constructs.

Methods for transforming methylotrophic yeast, such as, for example, *P. pastoris*, as well as methods for culturing methylotrophic yeast cells containing in their genome a gene encoding a heterologous protein, are generally known in the art. The expression cassettes may be introduced into the methylotrophic yeast cells by any method known to those of skill in the art. Preferred methods include the spheroplast technique, described by Cregg et al. (1985) *Mol. Cell. Biol.* 5: 3376 and U.S. Pat. No. 4,879,231, and the whole-cell lithium chloride yeast transformation system (Ito et al. (1984) *Agric. Biol. Chem.* 48: 341), with modification necessary for adaptation to methylotrophic yeast such as *P. pastoris* (See European Patent Application No. 312,934; also available as U.S. Pat. No. 4,929,535).

If the yeast host is transformed with a linear DNA fragment containing the IGF-1 gene and DNA encoding αMF pre-pro sequences necessary for processing and secretion under the regulation of a promoter region of a *P. pastoris* gene, the expression cassette is integrated into the host genome by any of the gene replacement techniques known in the art, such as by one-step gene replacement (see e.g., Rothstein (1983) *Methods Enzymol.* 101: 202; Cregg et al. (1987) *Bio/Technology* 5: 479; and U.S. Pat. No. 4,882,279) or by two-step gene replacement methods (see e.g., Scherer and Davis (1979) *Proc. Natl. Acad. Sci. USA*, 76: 4951). The linear DNA fragment is directed to the target gene by flanking DNA sequences having sufficient homology with the target gene to effect integration of the DNA fragment therein. One-step gene disruptions are usually successful if the DNA to be introduced has as little as 0.2 kb homology with the fragment locus of the target gene; it is preferable however to maximize the degree of homology for efficiency.

In preferred embodiments, multiple copies of these expression cassettes are included on one DNA fragment, preferably in a head-to-tail orientation.

If the DNA fragment is included in a circular plasmid, the plasmid may be integrated by addition rather than gene disruption into the genome. One or more copies of the plasmid can be integrated at the same or different loci of the genome. Integration into the genome is facilitated by linearization of the plasmid by means of a suitable restriction endonuclease.

DNA fragments in the expression cassette(s) are said to be "operably associated" with one another when the DNA sequence encoding the IGF-1 peptide is positioned and oriented functionally with respect to the promoter, the DNA sequence encoding the S. cerevisiae αMF pre-pro sequence and the transcription terminator. Thus, the polypeptide-encoding segment is transcribed under regulation of the promoter region into a transcript capable of providing, upon translation, the desired polypeptide. Because of the presence of the signal sequence, such as the αMF pre-pro sequence, the expressed IGF-1 product is secreted into the culture medium. Appropriate reading frame positioning and orientation of the various segments of the expression cassette are within the knowledge of persons of skill in the art and are specifically described in the Examples.

Positive transformants may be isolated, identified and characterized by any method known to those of skill in the art, including Southern blot analysis (Maniatis et al. (1982) *Molecular Cloning: A Laboratory Manual,* Cold Spring Harbor Laboratory Press, Cold Spring Harbor, N.Y., USA) to determine, for example, the site of DNA integration; Northern blots (Maniatis et al. (1982) *Molecular Cloning: A Laboratory Manual,* Cold Spring Harbor Laboratory Press, Cold Spring Harbor, N.Y., USA; R. S. Zitomer and B. D. Hall (1976) *J. Biol. Chem,* 251: 6320), for example, to confirm methanol-responsive IGF-1 gene expression; and product analysis to detect the presence of secreted IGF-1 peptides in the growth media.

The presently preferred host cells for transformation with multiple expression cassettes are *P. pastoris* cells having at least one mutation that can be complemented with a marker gene present on a transforming DNA fragment. Preferably His4⁻ (GS115) or Arg4⁻ (GS190) auxotrophic mutant *P. pastoris* strains are employed. The most preferred strains are additionally deficient in expression of one or more proteases that are not required for proper processing of the selected leader sequence. The deficiency may be manifested as an absence of or a decrease in the activity of one or more proteases by virtue of point mutations, insertions, or deletions in genes that encode proteases or genes that directly or indirectly modulate expression of genes that encode proteases.

In preferred embodiments, DNA fragments containing one or more expression cassette(s) are inserted into a vector containing a marker gene complementing the host's defect, and optionally containing additional sequences such as bacterial marker genes, yeast sequences which direct vector integration, and the like. Plasmids based on pBR322, such as pAO815, are preferred as vectors. Insertion of one or more copies of the IGF-1 expression/secretion cassette into parent plasmid pAO815 produces plasmids such as pIGF201, pIGF202, pIGF204, pIGF206, and pIGF816.

Protease-deficient strains of *P. pastoris,* known as pep4⁻ or pep4⁻ prb-1⁻ strains, described below and in U.S. patent application Ser. No. 07/678,916, are among the preferred host cells. Protease-deficient *P. pastoris* strains are generated by disruption of *P. pastoris* genes, such as the PEP4 gene or PRB-1 gene, that encode a protein that directly or indirectly affects the protease activity of the cell. This disruption is preferably accomplished by the insertion of a plasmid or DNA fragment, unrelated to the constructs for expression of IGF-1, into the PEP4 gene or PBR-1 gene. This disruption results in a reduction of some of the protease activities in the cells, such as, for example, proteinase A, proteinase B and carboxypeptidase Y activities. This host cell strain preferably also contains a mutation that can be complemented by a marker gene carried on the expression cassette, as discussed below in the Examples.

The preferred host cells may be transformed with the expression vectors that are introduced into targeted specific sites in the host cell genome in order to generate Mut⁻ or Mut⁺ expression strains of *P. pastoris.* "Mut" refers to the methanol-utilization phenotype. In certain embodiments, Mut⁻ strains are prepared by first digesting the selected expression vector with an appropriate enzyme to yield a linear DNA fragment with ends homologous to the 5' and 3' ends of the AOX1 gene. The linearized DNA construct expression cassette(s) is then integrated into the host genome at the AOX1 site by a one-step gene replacement technique. As a result of gene replacement of the AOX1, Mut⁻ strains are obtained. Mut⁻ strains exhibit decreased ability to utilize methanol. This is manifested as a slow growth rate of the strain on methanol, which is maintained by expression of the AOX2 gene product. Mut⁻ transformants in which the expression cassette has integrated into the AOX1 locus by site-directed recombination can be identified by first screening for the presence of a complementing marker gene present in the expression cassette. This is preferably accomplished by growing the cells in medium lacking the complementing gene product and identifying those cells which are able to grow by virtue of the expression of the complementing gene. Next, the selected cells are screened for their "Mut" phenotype by growing them in the presence of methanol and monitoring their growth rate. Mut⁻ phenotypes have much slower growth on methanol than the parent strain.

To develop Mut⁺ IGF-1-expressing strains, the fragment that contains one or more expression cassette(s) preferably is integrated into the host genome by transformation of the host with a circular plasmid or a linearized plasmid containing the DNA construct. The DNA is integrated into a locus or loci having homology with one or more sequences present in the fragment.

Positive transformants may be characterized by Southern analysis to identify, for example, the site of DNA integration; by Northern analysis to detect, for example methanol-responsive IGF-1 gene expression; and by product analysis to detect the presence of secreted IGF-1 peptides in the growth medium.

Culturing transformed yeast host cells that harbor the DNA constructs.

The transformed hose cells are cultured under conditions in which the DNA encoding IGF-1, signal and processing signals, is expressed, and the pre-pro-peptide is processed and secreted. Transformed strains, of the desired phenotype and genotype, may be grown in large quantities by any means known to those of skill in the art. In preferred embodiments, the strains are cultured in fermentors. For the large-scale production of recombinant DNA-based products in methylotrophic yeast, a three-stage, high cell-density, fed batch fermentation system is normally the preferred fermentation protocol.

In the first, or growth stage, expression hosts are cultured in defined minimal medium with an excess of a non-inducing carbon source, such as but not limited to, glycerol. When grown on such carbon sources, heterologous gene expression is completely repressed, which allows the generation of cell mass in the absence of heterologous protein expression. It is presently preferred, during this growth stage, to maintain the pH of the medium at about 5. The second stage, referred to as a period of growth under limiting conditions, refers to a short period of non-inducing carbon source limitation growth. In this stage, cell mass continues to increase and the methanol-responsive promoter is derepressed. Although a pH of about 5 is preferred for optimal growth of *P. pastoris*, undetectable or low levels of IGF-1 are obtained from the broth of proteolytically intact IGF-1-expressing strains that are cultured entirely at pH 5. High concentrations of IGF-1 are produced, however, if the pH of the medium during the limitation growth period is adjusted to about 4 or less, preferably in the range of about 2–3.5. This pH is maintained during the production phase.

Expression of IGF-1 from protease deficient strains is less sensitive to pH than expression from proteolytically intact strains. Protease deficient strains may be cultured entirely at pH 5. Alternatively, and preferably, protease deficient strains are cultured at pH 5 during the first two stages, after which the pH is lowered to about 2.5 to about 3.0 during the third stage.

In the third stage, the production stage, either methanol alone, referred to herein as "methanol excess fed-batch mode" or a limiting amount of a non-inducing carbon source plus methanol, referred to herein as "mixed-feed fed-batch mode" are added in the fermentor. Addition of methanol induces expression of genes, including IGF-1, that are in operative linkage with methanol-responsive promoters.

According to a preferred embodiment, the heterologous protein expression system used for IGF-1 production utilizes the promoter derived from the methanol-regulated AOX1 gene of *P. pastoris*. This promoter is tightly regulated and provides for efficient gene expression. The AOX1 gene can be the source of the transcription terminator as well. The presently preferred expression cassette comprises, in operational association with one another, the *P. pastoris* AOX1 promoter, DNA encoding the *S. cerevisiae* αMF pre-pro sequence including DNA encoding the processing sequence lys-arg-(glu-ala)$_x$, in which x may vary from 0 to 3, DNA encoding IGF-1 polypeptides, and a transcription terminator derived from the *P. pastoris* AOX1 gene. Preferably, two or more of such expression cassettes are contained on one DNA fragment, in head-to-tail orientation, to yield multiple expression cassettes on a single contiguous DNA fragment.

Selected methylotrophic yeast transformants that have the desired genotype and phenotype are cultured in fermentors under conditions in which IGF-1 is expressed and secreted into the culture medium. It is presently preferred to use the three-step production process described above. The level of IGF-1 secreted into the media can be determined by western blot analysis of the medium in parallel with an IGF-1 standard, using anti-IGF-1 antisera; by radioimmunoassay (RIA); by radio-receptor assay; or by HPLC after suitable pretreatment of the medium.

As noted above, IGF-1 as used herein is intended to embrace all the allelic variations of IGF-1. Moreover, as noted above, derivatives obtained by simple modification of the amino acid sequence of the naturally occurring product, e.g., by way of site-directed mutagenesis or other standard procedures, are included within the scope of the present invention. Forms of IGF-1 produced by proteolysis by host cell proteases that exhibit similar biological activities to naturally occurring IGF-1 are also encompassed by IGF-1.

The following examples are included for illustrative purposes only and are not intended to limit the scope of the invention.

EXAMPLES

*P. pastoris* is described herein-as a model system for the use of methylotrophic yeast hosts. Methylotrophic yeast host cells from four genera: Candida, Hansenula, Pichia and Torulopsis may also be used. Host cells from any species that demonstrably grows on methanol as the sole carbon nutrient may be used (see, e.g., Gleeson et al. (1988) *Yeast* 4: 1). Such species may be used as described herein for *P. pastoris*.

Example 1

CONSTRUCTION OF THE PICHIA PASTORIS EXPRESSION VICTORS USED IN THE PREPARATION OF THE IGF-1 EXPRESSION VECTORS

A. Construction of plasmid pAO203.

Plasmid pAO203 contains a 5' EcoRI-3'HindIII DNA fragment encoding the αMF pre-pro region, the amino acids of protease processing sites, lys-arg and (glu-ala)$_2$ and the AOX1 transcription terminator.

The AOX1 transcription terminator was isolated from pPG2.0. Plasmid pPG2.0 had been prepared by inserting the BamHI-HindIII fragment of pG4.0 (NRRL 15868), which contains the AOX1 terminator, into pBR322. 20 µg of pPG2.0 was digested with StuI, followed by the addition of 0.2 µg SalI linkers (GGTCGACC). The plasmid was subsequently digested with HindIII and the 350 bp HindIII-SalI fragment was isolated from a 10% acrylamide gel and subcloned into pUC18 (Boshringer Mannheim) that had been digested with HindIII and SalI. The ligation mix was transformed into JM103 cells and Amp$^R$ colonies were selected. The correct construction was verified by HindIII and SalI digestion, which yielded a 350 bp fragment, and was called pAO201.

5 µg of pAO201 was digested with HindIII, filled in using *E. coli* DNA Polymerase I Klenow fragment, and 0.1 µg of BglII linkers (GAGATCTC) were added. After digestion of the excess BglII linkers, the plasmid was reclosed and transformed into MC1061 cells. Amp$^R$ cells were selected, DNA was prepared, and the correct plasmid was verified by BglII, SalI double digests, which yielded the expected 350 bp fragment, and by a HindIII digest, which showed loss of a HindIII site. This plasmid was designated pAO202.

An alpha factor-GRF fusion was isolated as a 360 bp BamHI-PstI partial digest from pYSV201. Plasmid pYSV201 had been prepared by inserting the EcoRI-BamBHI fragment of GRF-E-3, may be constructed by cloning DNA encoding the alpha factor pre-pro sequence and linking it to DNA encoding GRF.

In the present specification the αMF pre-segment means the first 83 amino acids of the alpha factor leader peptide, which means the polypeptide containing the first 89 amino acids of the protein encoded by the *S. cerevisiae* alpha mating factor gene as reported by Kurjan et al. (1982) *Cell* 30: 933–943 (SEQ ID No. 14, amino acids 1–83).

Alpha-factor genomic DNA was cloned by screening a genomic DNA library of Sau3A partially digested *Saccharomyces cerevisiae* DNA inserted in the BamHI site of YEp13, which was obtained from the ATCC under accession number 37115. The DNA for the library was prepared from *Saccharomyces cerevisiae* strain AB320 (HO, ade2-1, lys2-1, trp5-2, leu2-1, can1-100, ura3-1, ura1-1, met4-1), partially digested and inserted into YEp13. *E. coli* was transformed with the library using competent MC1061 cells and a heat shock step. The cells were rendered competent by growing to mid-log ($OD_{600}$=0.3), incubating in $CaCl_2$, at half the original volume, for 30 minutes on ice, centrifuging, and resuspending the cells in $\frac{1}{50}$ of the original volume of 10% glycerol in 50 mM $CaCl_2$. The cells were then quick frozen and stored at −70° C. For transformation, the 100 µl of cells were thawed on ice and added to 10 ng of the DNA and incubated on ice for 15 minutes. The cells were then placed at 37° C. for 5 minutes, followed by a 23° C. incubation. The cells were spread onto 1.5% agar plates containing L-broth and 50 µg/ml of ampicillin for selection of ampicillin resistant transformants. About $10^4$ ampicillin-resistant transformants were obtained from the YEp13 library.

The resistant colonies were plated onto five plates at a density of 4000 colonies per plate. Duplicate colony hybridization filters were prepared and probed with a $^{32}P$ labeled probe having the sequence CGCAGCATTCTTCGCATT-AGC (SEQ ID NO. 13) derived from the known sequence of the alpha-factor (nucleotides 36–56 of the coding region) published by Kurjan et al. (1982) *Cell* 30: 933–943.

Prehybridization was performed at 42° C. in 6xSSPE (1xSSPE is 0.18M NaCl, 10 mM $NaPO_4$, pH 7.0, 1 mM EDTA), 10x Denhardt's (1x Denhardt's is 0.02% bovine serum albumin, 0.02% Ficoll, 0.02% polyvinylpyrollidone), 0.5% SDS for 3 hours. Hybridization was performed as above, but with 10% dextran sulfate and $10^6$ cpm of probe per ml of hybridization buffer at 42° C. for 18 hours. The filters were washed with 2 xSSC and 0.5% SDS at room temperature. Seven positive colonies were identified.

Regions of a plate showing strong hybridization signals with the probe in duplicate were isolated and streaked on a 1.5% LB agar plate (i.e., 1.5% agar containing LB medium (0.5% Bacto-tryptone, 0.5% yeast extract, 0.25% NaCl, pH adjusted to 7.5 with NaOH)) containing 50 µg/ml ampicillin. From this plate, single colonies were isolated and placed into wells of an 8×12 well microtiter dish containing 100 µl liquid LB+50 µg/ml ampicillin. After 18 h growth at 37° C., they were adjusted to 15% glycerol and stored at −70° C. A stamping device capable of transferring all colonies of an 8×12 well microtiter dish (96 wells) to a 15 cm filter grown on a 1.5% LB+50 µg/ml ampicillin plate was used to transfer single colony isolates from each positive hybridization region to a nitrocellulose filter in duplicate. These colonies were grown for 18 hours at 37° C., and the filters were hybridized with the 21 base oligomer (SEQ ID No. 13) as described above. Four positive colonies were isolated in this manner and grown up in 2 ml liquid cultures of LB+50 µg/ml ampicillin [LB-AMP(50)] at 37° C. with agitation for 5–18 hours.

DNA was prepared from 1.5 ml of this culture by spinning the cells out and decanting the medium. The cells were suspended in 100 µl of 50 mM glucose, 10 mM EDTA, 25 mM Tris-HCl, pH 8.0. They were allowed to sit on ice 5 minutes, after which 200 µl of 0.2N NaOH, 1% SDS was added, and the mixture was incubated 5 minutes at 0° C. To this mixture was added 150 µl of 3M sodium acetate, pH 5.2. After 10 minutes at 0° C., the tube was centrifuged for 10 minutes in a microfuge. The pellet was removed with a toothpick, and 400 µl of a 1:1 mixture of phenol chloroform (saturated with 10 mM Tris pH 7.5, 1 mM EDTA) was added. The aqueous layer (less than 400 µl) was removed after centrifugation, and 800 µl of 95% ethanol was added thereto. After incubation at −70° C. for 20 minutes, the sample was spun for 5 minutes in a microfuge. The pellet was washed with 1 ml of 95% ethanol, air dried and dissolved in 20–50 µl of 10 mM Tris-HCl, mM EDTA, 10 µg/ml Ribonuclease A.

EcoRI restriction digests were performed by adding 1 µl of the mini-prepped DNA (200–500 ng) to the buffer prescribed by the manufacturer in a volume of 10 µl. The appropriate restriction enzyme was added at a concentration of 5–10 units and the digest was incubated at 37° C. for 1–2 hours. The digest was analyzed by agarose gel electrophoresis (0.8–1.2%), and fragment sizes were quantitated by reference to known standards.

After electrophoresis, a photograph of the restriction digest and mobility markers (a HindIII digest of bacteriophage lambda DNA in this case) was taken in the presence of a ruler to measure the mobility of the fragments relative to the origin. The gel was then treated with 0.5N NaOH, 1.5M NaCl in a volume of 50 ml at room temperature with shaking for 30 minutes. It was subsequently neutralized by treatment with 1M Tris-HCl, pH 8.0, 1M NaCl in a volume of 50 ml at room temperature with shaking for 30 minutes. The gel was then placed on a stack of Whatman 3MM paper soaked in 20 xSSC (3M NaCl, 0.3M Na citrate, pH 7.0). On top of the gel was placed a nitrocellulose filter which had been wetted in 2 xSSC (0.3M NaCl, 0.03M Na citrate pH 7.0). The stack was topped with dry paper towels. The diffusion of the salt solution through the gel, past the nitrocellulose filter into the dry towels causes the transfer of DNA from the gel to the filter. The filter was then rinsed in 2 xSSC and baked at 80° C. for 2 hours. Hybridization was performed as follows: The filter was wetted in 5 xSSPE [1 xSSPE: 0.18M NaCl, 10 mM $NaPO_4$ (pH 7.0), 1 mM EDTA], 0.5% SDS, 1 mg/ml denatured, sheared, salmon sperm DNA. To this solution was added $5 \times 10^5$ cpm/ml hybridization fluid of $^{32}P$-labeled oligonucleotide (the 21 base probe in this case). After hybridization at the specified temperature ($T_m$-5° C. for oligonucleotide probes) for 12–18 hours, the filter was washed at room temperature in 2 xSSC, 0.5% SDS in a volume of 200 ml with agitation for 10 minutes. This wash was repeated and the filter was washed in the same buffer but at the hybridization temperature with agitation for 10 minutes. The filter was air dried and exposed to Kodak XAR-5 film with the presence of a DuPont intensifying screen at −70° C. for 12 hours.

Since, most of the structural gene for the alpha mating factor is present on a 500 bp PstI-SalI fragment (SEQ ID No. 14; see, Kurjan et al. (1982) *Cell* 30: 933–943), the genomic clone isolated from the YEp13 library was digested with PstI and SalI and subjected to electrophoresis on 8% polyacrylamide. The band was excised from the gel after visualization of the ethidium bromide-stained band via UV excitation. The size of the band was determined via reference to molecular weight standards (a HaeIII digest of φX174 phage DNA in this case). This gel slice was placed in a dialysis bag containing electrophoresis buffer, 1xTBE (0.089M Tris borate, 0,089M boric acid, 2 mM EDTA) in this case. The bag was placed in an electrophoresis chamber and run at 100 volts (constant voltage for 1–2 hr). At the end of the run, the current was reversed for 1 minute. The buffer, now containing the DNA, was removed from the dialysis bag, phenol-extracted and concentrated by extraction with secondary butyl alcohol, adjusted to 0.3M sodium acetate (NaOAc) and ethanol-precipitated. The recovered DNA was quantitated via gel electrophoresis and referenced to standards of known concentration.

The PstI-SalI fragment was cloned into M13mp8 and M13mp9 vectors. These vectors were cleaved with SalI and PstI, using manufacturer's specifications for restriction enzyme digestion, and diluted to 10 ng per microliter. They were heated to 65° C. to inactivate any remaining endonuclease activity. In cases where restriction endonucleases are refractory to heat inactivation, the sample was phenol-extracted, ether-washed and ethanol-precipitated, then diluted to 10 ng/μl in TE. Ten ng of vectors and 50–100 ng of insert were ligated in the presence of 50 mM Tris-HCl, pH 7.5, 10 mM $MgCl_2$, 10 mM dithiothrieitol, 1 mM spermidine, 1 mM ATP, and 200–400 Units (New England Biolabs) of T4 ligase. After a certain interval, 0.5–2 hours at 23° C. or 5–16 hours at 16° C., the ligation reaction was used to transform E. coli JM103, which had been rendered competent.

E. coli JM103 cells are rendered competent in the following fashion. They are seeded from a minimal plate and grown to $OD_{550}$=0.3, centrifuged at 4° C. and suspended in ½ volume of cold 50 mM $CaCl_2$, left on ice for 20 minutes and centrifuged. They are resuspended in 1/10 the original culture volume and stored at 4° C. until used.

During transformation, 100–200 μl of culture of these cells were added to the ligation reaction mixture and placed on ice for 20 minutes. They were heated to 42° C. for 2 minutes. Meanwhile, to a molten solution of 1% LB agar was added 30 μl of a 20 mg/ml solution of X-gal' (5 bromo-4 chloro-3-indolyl-beta-D-galactoside) in dimethyl formamide and 20 μl of (24 mg/ml) isopropyl β-D-thiogalactoside. At the end of the two minute 42° C. incubation, the cells and DNA were added to the top agar and spread on a room temperature 1.5% LB plate. They were subsequently incubated at 37° C. for 12–16 hours. Clones containing inserts appeared as white plaques, while reclosed or uncut vectors produce a blue color.

Plaques containing inserts of the PstI-SalI fragment were isolated in M13mp8 and M13mp9 vectors in the manner described above. Template for sequencing was isolated in the following manner. A plaque was cored and placed in 1–2 ml of liquid LB and shaken for 5–6 hours at 37° C.. A 1 ml aliquot of the supernatant was centrifuged and 900 μl was recovered. This was recentrifuged and 800 μl was recovered. 200 μl of 2.5M NaCl, 20% PEG6000 was added and the mixture was let stand for 15 minutes at 23° C.. After centrifugation, the supernatant was completely removed and the pellet was resuspended in 100 μl of 10 mM Tris-HCl, pH 7.5, 0.1 mM EDTA (TE). 50 μl of TE-saturated phenol was added and the sample was extracted. Following centrifugation, the aqueous phase was extracted with diethyl ether and the aqueous phase was adjusted to 0.3M sodium acetate pH 5.2. 250 μl of ethanol was added and the solution was frozen in a dry ice-ethanol bath. Following centrifugation for 5 minutes, the pellet was resuspended in 50 μl TE.

Five μl aliquots of the clone were sequenced by the Sanger dideoxynucleotide method, verifying that this clone encoded the alpha-factor gene because the sequence was identical to the known published sequence (see, Kurjan et al. (1982) Cell 30: 933–943; SEQ ID No. 14).

One of the selected clones was digested with EcoRI and HindIII and the 1200 bp EcoRI-HindIII fragment was isolated and ligated into pBR322 that had been digested with EcoRI and HindIII. The resulting plasmid was designated p-alpha-factor.

DNA encoding human pancreatic GRF (hGRF) designed for expression in E. coli (including DNA encoding 44 amino acids and an artificial initiator methionine) was obtained as a chemically synthesized EcoRI-BamHI fragment and was purchased from Creative Biomolecules. The sequence of this fragment is set forth in SEQ ID NO. 15. DNA encoding an EcoRI site was linked to the 5' end of the fragment and DNA encoding a BamHI site was linked to the 3' end and includes the G from the stop codon.

The ATG encoding $Met^{27}$ (amino acid 28 in SEQ ID No. 14) was changed to CTG encoding $Leu^{27}$ to produce GRFD' ($Leu^{27}$-hgrf(1-44)-OH). This was accomplished by ligating the above fragment into pBR322 and digesting with HindIII and XbaI. Changing the Met codon to a Leu codon using an oligonucleotide having the sequence (SEQ ID No. 16):

5' AGCTCCTGCAGGATATCCTGT 3' also eliminated a HindIII site at the DNA encoding amino acids 21 and 22. To effect these changes the oligonucleotide was ligated with the XbaI/HindIII-cut vector and the resulting mixture was transformed into MC1061. Transformants were screened for the presence of two PvuII sites. In order to eliminate plasmids with multiple inserts, the selected plasmids were digested with XbaI and religated at a concentration of 20 ng/μl. MC1061 cells were transformed with the resulting mixture and ampicillin-resistant colonies were selected and analyzed by digestion with EcoRI and BamHI. Plasmids containing 140 bp fragments, instead of 190 bp fragments, were designated GRF-D'.

GRF-D' was digested with HgaI and BamHI and a 118 bp fragment was isolated and ligated with the following oligonucleotide that replaces the amino acids eliminated by HgaI digestion, removes the N-terminal Met, and leaves a 5' overhang that can ligate with the HindIII end of the pre-pro-alpha factor encoding DNA (SEQ ID No. 17):

5' AGCTTACGCAGACGCTATCT 3'

The ligated insert was digested with BamHI and HindIII in order to eliminate multimers and was then ligated to HindIII-BamHI-digested plasmid p-alpha factor. The resulting mixture was transformed into MC1061 cells and ampicillin-resistant transformants selected. Plasmid from a selected transformant that contained the correct insert was designated GRF-E-3.

Thus, GRF-E-3 is pBR322 containing the 5'-upstream region of the gene encoding alpha-factor from the EcoRI site to the initiation codon and the DNA encoding the complete pre-pro-alpha-factor leader (83 amino acids, including the Lys-Arg and (Glu-Ala)$_2$ sites). The GRF encoding DNA is linked such that the DNA encoding the first amino acid of GRF (Gly) immediately follows the processing sites for alpha-factor. Thus, the insert encodes the fusion protein having the formula:

alpha factor leader peptidelys—arg—glu—ala—glu—ala—hGRF—OH.
(processing site)

plasmid was digested with BamHI and partially digested with PstI. The following oligonucleotides were added to this partial digest:

5' AATTCGATGAGATTTCCTTCAATTTTTACTGCA 3' (Seq. ID No. 8)
3'       GCTACTCTAAAGGAAGTTAAAAATG       5' (Seq. ID No. 9).

Only the antisense strand of the oligonucleotide was kinase labelled so that the oiigonucleotides did not polymerize at the 5'- end. A 350 bp fragment was isolated by electro elution following acrylamide gel electrophoresis (10%). This EcoRI- BamHI fragment of 385 bp was cloned into pA0202 which had been cut with EcoRI and BamHI. MC1061 cells were transformed and Amp$^r$ cells were selected. The resulting plasmid, pA0203, was identified by cutting with EcoRI and BglII to yield a fragment of greater than 700 bp.

B. Construction of plasmid pa0807.

1. Preparation of fl-ori DNA.

Bacteriophage f1 DNA (50 μg) was digested with 50 units of RsaI and DraI to release the ≈458 bp DNA fragment containing the f1 origin of replication (ori). The digestion mixture was extracted with an equal volume of phenol:chloroform (V/V) followed by extracting the aqueous layer with an equal volume of chloroform and finally the DNA in the aqueous phase was precipitated by adjusting the NaCl concentration to 0.2M and adding 2.5 volumes of absolute ethanol. The mixture was allowed to stand on ice (4° C.) for 10 minutes and the DNA precipitate was collected by centrifugation for 30 minutes at 10,000 x g in a microfuge at 4° C.

The DNA pellet was washed 2 times with 70% aqueous ethanol. The washed pellet was vacuum dried and dissolved in 25 μl of TE buffer (1.0 mM EDTA in 0.01M (pH 7.4) Tris buffer). This DNA was electrophoresed on 1.5% agarose gel and the gel portion containing the ≈458 bp fl-ori fragment was excised out and the DNA in the gel was electroeluted onto DE81 (Whatman) paper and eluted from the paper in 1M NaCl. The DNA solution was precipitated as detailed above and the DNA precipitate was dissolved in 25 μl of TE buffer (fl-ori fragment).

2. Cloning of fl-ori into DraI sites of pBR322.

Plasmid pBR322 (2 μg) was partially digested with 2 units of DraI. The reaction was terminated by phenol:chloroform extraction followed by precipitation of DNA as detailed in step 1 above. The DNA pellet was dissolved in 20 μl of TE buffer. About 100 ng of this DNA was ligated with 100 ng of fl-ori fragment (step 1) in 20 μl of ligation buffer by incubating at 14° C. for overnight with 1 unit of T4 DNA ligase. The ligation was terminated by heating to 70° C. for 10 minutes and then used to transform E. coli strain JM103 (Janisch-Perron et al. (1983) Gene 22: 103). Amp$^R$ transformants were pooled and superinfected with helper phage R408. Single stranded phage were isolated from the media and used to reinfect JM103. Amp$^R$ transformants contained pBRfl-ori which contains fl-ori cloned into the Dra I sites (nucleotide positions 3232 and 3251) of pBR322.

3. Construction of the plasmid pAO807.

Plasmid pBRfl-ori (10 μg) was digested for 4 hours at 37° C. with 10 units each of Pst I and Nde I. The digested DNA was phenol:chloroform extracted, precipitated and dissolved in 25 μl of TE buffer, as detailed in step 1 above. This material was electrophoresed on a 1.2% agarose gel and the Nde I—Pst I fragment (approximately 0.8 kb) containing the fl-ori was isolated and dissolved in 20 μl of TE buffer as detailed in step 1 above. About 100 ng of this DNA was mixed with 100 ng of pAO804, which had been prepared as described in published International Patent Application No. WO 89/04320, May 18, 1989 and below and which had been digested with PstI and NdeI and phosphatase-treated. This mixture was ligated in 20 μl of ligation buffer by incubating overnight at 14° C. with 1 unit of T4 DNA ligase. The ligation reaction was terminated by heating at 70° C. for 10 minutes. This DNA was used to transform E. coli strain JM103 to obtain pAO807.

C. Construction of plasmid pAOSO4:

Plasmid pAO804 has been described in published International Patent Application No. WO 89/04320, May 18, 1989. Construction of this plasmid involved the following steps:

Plasmid pBR322 was modified as follows to eliminate the EcoRI site and insert a BglII site into the PVuII site. Plasmid pBR322 was digested with EcoRI, the protruding ends were filled in with Klenow Fragment of E. coli DNA polymerass I, and the resulting DNA was recircularized using T4 ligase. The recircularized DNA was used to transform E. coli MC1061 to ampicillin-resistance and transformants were screened for having a plasmid of about 4.37 kbp in size without an EcoRI site. One such transformant was selected and cultured to yield a plasmid, designated pBR322ARI, which is pBR322 with the EcoRI site replaced with the sequence:

5'-GAATTAATTC-3' (Sequence ID No. 12)

Plasmid pBR322nRI was digested with PvuII, and the linker having the sequence:

5'-CAGATCTG-3'
3'-GTCTAGAC-5' was ligated to the resulting blunt ends employing T4 ligase. The resulting DNAs were recircularized, also with T4 ligase, and then digested with BglII and again recircularized using T4 ligase to eliminate multiple BglII sites due to ligation of more than one linker to the PvuII-cleaved pBR322ΔRI. The DNAs, treated to eliminate multiple BglII sites, were used to transform E. coli MC1061 to ampicillin-resistance. Transformants were screened for a plasmid of about 4.38 kbp with a BglII site. One such transformant was selected and cultured to yield a plasmid, designated pBR322ΔRIBGL, for further work. Plasmid pBR322ΔRIBGL is the same as pBR322ΔRI except that pBR322ΔRIBGL has the sequence 5'-CAGCAGATCTGCTG-3' (Sequence ID No. 11)

in place of the PvuII site in pBR322ΔRI.

Plasmid pBR322ΔRIBGL was digested with a SalI and BglII and the large fragment (approximately 2.97 kbp) was isolated. Plasmid pBSAGI5I, which is described, for example, in European Patent Application Publication No. 0 226 752, was digested completely with BglII and XhoI and an approximately 850 bp fragment from a region of the P. pastoris AOX1 locus downstream from the AOX1 gene transcription terminator (relative to the direction of transcription from the AOX1 promoter) was isolated. The BglII-XhoI fragment from pBSAGI5I and the approximately 2.97 kbp, SalI-BglII fragment from pBR322ΔRIBGL were combined and subjected to ligation with T4 ligase. The ligation mixture was used to transform E. coli MC1061 to ampicillin-resistance and transformants were screened for a plasmid of the expected size (approximately 3.8 kbp) with a BglII site. This plasmid was-designated pAO801. The overhanging end of the SalI site from the pBR322ΔRIBGL fragment was ligated to the overhanging end of the XhoI site on the 850 bp pBSAGI5I fragment and, in the process, both the SalI site and the XhoI site in pAO801 were eliminated.

Plasmid pBSAGI5I was then digested with ClaI and the approximately 2.0 kbp fragment was isolated. The 2.0 kbp fragment has an approximately 1.0-kbp segment which comprises the *P. pastoris* AOX1 promoter and transcription initiation site, an approximately 700 bp segment encoding the hepatitis B virus surface antigen (HBsAg) and an approximately 300 bp segment which comprises the *P. pastoris* AOX1 gene polyadenylation signal and site-encoding segments and transcription terminator. The HBsAg coding segment of the 2.0 kbp fragment is terminated, at the end adjacent the 1.0 kbp segment with the AOX1 promoter, with an EcoRI site and, at the end adjacent the 300 bp segment with the AOX1 transcription terminator, with a StuI site, and has its subsegment which codes for HBsAg oriented and positioned, with respect to the 1.0 kbp promoter-containing and 300 bp transcription terminator-containing segments, operatively for expression of the HBsAg upon transcription from the AOX1 promoter. The EcoRI site joining the promoter segment to the HBsAg coding segment occurs just upstream (with respect to the direction of transcription from the AOX1 promoter) from the translation initiation signal-encoding triplet of the AOX1 promoter.

Plasmid pAO801 was cut with ClaI and mixed with T4 ligase and the approximately 2.0 kbp ClaI-site-terminated fragment from pBSAGI5I. The ligation mixture was used to transform *E. coli* MC1061 to ampicillin resistance, and transformants were screened for a plasmid of the expected size (approximately 5.8 kbp) which, upon digestion with ClaI and BglII, yielded fragments of about 2.32 kbp (with the origin of replication and ampicillin-resistance gene from pBR322) and about 1.9 kbp, 1.48 kbp, and 100 bp. On digestion with BglII and EcoRI, the plasmid yielded an approximately 2.48 kbp fragment with the 300 bp terminator segment from the AOX1 gene and the HBsAg coding segment, a fragment of about 900 bp containing the segment from upstream of the AOX1 protein encoding segment of the AOX1 gene in the AOX1 locus, and a fragment of about 2.42 kbp containing the origin of replication and ampicillin resistance gene from pBR322 and an approximately 100 bp ClaI-BglII segment of the AOX1 locus (further upstream from the AOX1-encoding segment than the first mentioned 900 bp EcORI-BglII segment). Such a plasmid had the ClaI fragment from pBSAGI5I inserted in the desired orientation. Had it been inserted in the opposite undesired orientation, there would have been EcoRI-BglII fragments of about 3.3 kbp, 2.38 kbp and 900 bp. One of the transformants harboring the desired plasmid, designated pAO802, was selected for further work and was cultured to yield that plasmid.

Plasmid pAO802 was then treated to remove the HBsAg coding segment terminated with an EcoRI site and a StuI site. The plasmid was digested with StuI and a linker of sequence:

5'-GGAATTCC-3'
3'-CCTTAAGG-5' was ligated to the blunt ends using T4 ligase. The mixture was then treated with EcoRI and again subjected to ligating using T4 ligase. The ligation mixture was used to transform *E. coli* MC1061 to ampicillin resistance and transformants were screened for a plasmid of the expected size (5.1 kbp) with EcoRI-BglII fragments of about 1.78 kbp, 900 bp, and 2.42 kbp and BglII-ClaI fragment of about 100 bp, 2.32 kbp, 1.48 kbp, and 1.2 kbp. A transformant with the desired plasmid was selected for further work and was cultured to yield pAO803.

Plasmid pAO804 was prepared from pAO803 by inserting, into the BamHI site from pBR322 in pAO803, an approximately 2.75 kbp BglII fragment from the *P. pastoris* HIS4 gene. See, e.g., Cregg et al. (1985) *Mol. Cell. Biol.* 5, 3376 and European Patent Application Publication Nos. 180,899 and 188,677. Plasmid pAO803 was digested with BamHI and combined with the HIS4 gene-containing BglII site-terminated fragment and the mixture subjected to ligation using T4 ligase. The ligation mixture was used to transform *E. coli* MC1061 to ampicillin-resistance and transformants were screened for a plasmid of the expected size (7.85 kbp), which is cut by SalI. One such transformant was selected for further work, and the plasmid it harbors was designated pAO804.

Plasmid pAO804 has one SalI-ClaI fragment of about 1.5 kbp and another of abut 5.0 kbp and a ClaI-claI fragment of 1.3 kbp, indicating that the direction of transcription of the HIS4 gene in the plasmid is the same as the direction of transcription of the ampicillin resistance gene and opposite to the direction of transcription from the AOX1 promoter.

The orientation of the HIS4 gene in pAO804 is not critical to the function of the plasmid or any derivatives that include heterologous DNA fragments inserted at the EcoRI site between the AOX1 promoter and terminator fragments. Thus, a plasmid with the HIS4 gene in the orientation opposite to that of the HIS4 gene in pAO804 could be used in place of pAO804.

D. Construction of plasmid pA0815

Plasmid pAO815 was constructed by mutagenizing plasmid pAO807 to change the ClaI site downstream from the AOX1 transcription terminator in pAO807 into a BamHI site. The oligonucleotide used for mutagenizing pAO807 had the following sequence:

5'-GAC GTT CGT TTG TGC GGA TCC AAT GCG GTA GTT TAT-3' (Sequence ID No. 10).

Figure 6:
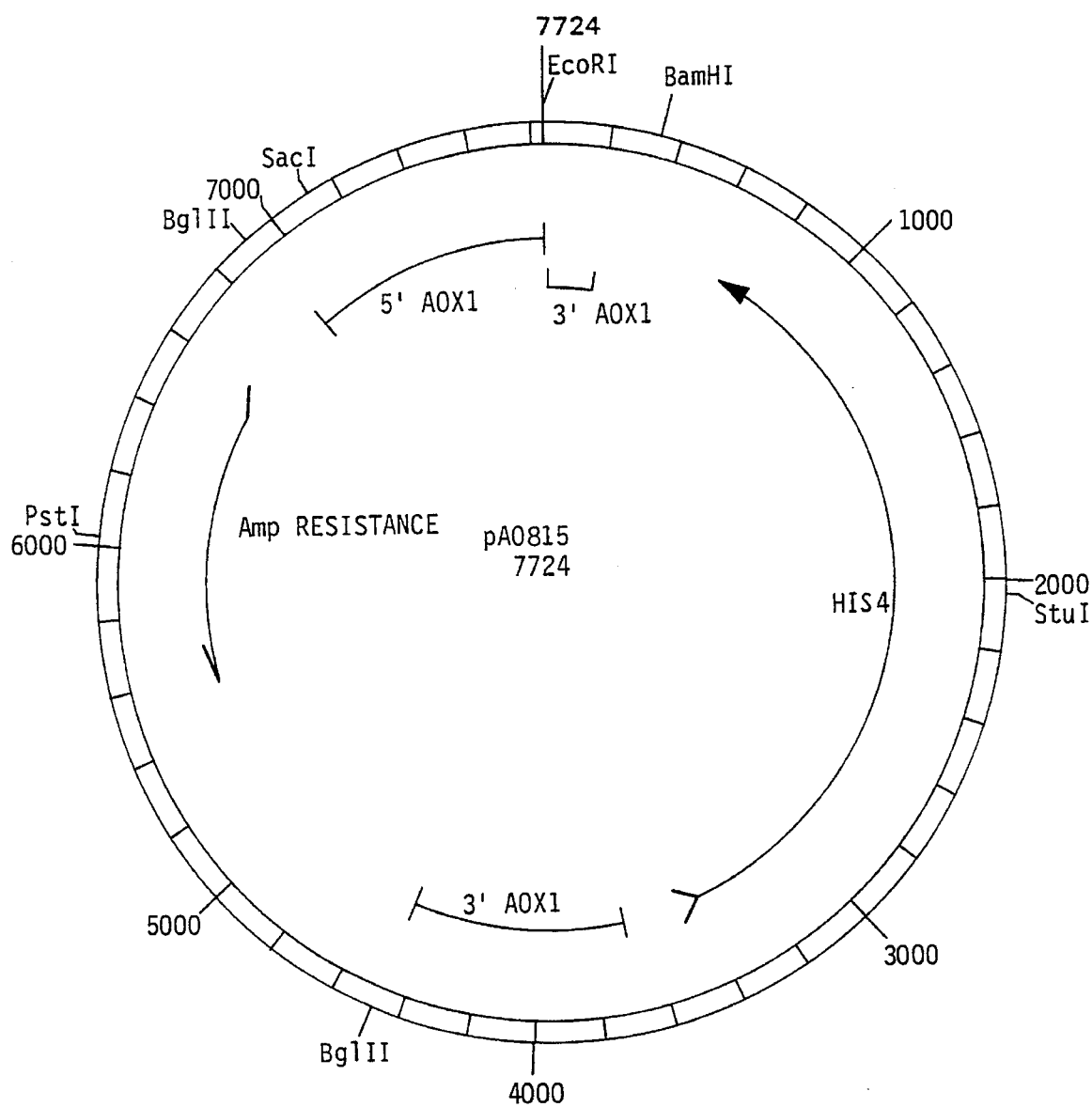
FIG. 6 is a restriction map of plasmid pAO815.

The mutagenized plasmid was designated pAO807-Bam. Plasmid pAO804 (described above and in International Patent Application WO 89/04320) was digested with BglII and 25 ng of the 2400 bp fragment were ligated to 250 ng of the 5400 bp BglIII fragment from BglII-digested pAO807Bam. The ligation mix was transformed into MC1061 cells and the correct construct was verified by digestion with PstI/BamHI to identify 6100 and 2100 bp sized bands. The correct construct was called pAO815. The restriction map of the expression vector pAO815 is shown in FIG. 6.

Example 2

CONSTRUCTION OF VECTORS FOR EXPRESSION OF IGF-1 IN *P. PASTORIS*

The expression vector constructions were carried out using standard procedures, as described, for example by Maniatis et al. ((1982) *Molecular Cloning: A Laboratory Manual*, Cold Spring Harbor Laboratory Press, Cold Spring Harbor, N.Y., USA) and Davis et al. ((1986) *Basic Methods in Molecular Biology*, Elsevier Science Publishing, Inc., N.Y.).

A. Construction of expression vectors that contain DNA encoding αMF prepro-lys-arg-IGF-1.

Expression vectors were prepared that contain one or multiple copies of the IGF-1 gene expression cassette, 5' AOX1-αMF prepro-lys-arg-IGF-1 - 3'AOX1, in which the αMF prepro-encoding element contains the αMF prepro-lys-arg but lacks glu-ala spacer-encoding nucleotides.

1. Construction of pIGF201 which contains a single copy of the expression cassette.

The synthetic gene encoding human IGF-1 shown in FIG. 1 as a HindIII-BamHI fragment, was incorporated into vector pUC18 and was used to transform *E. coli* strain MC1061. Ampicillin-resistant transformants were selected and screened by examination of restriction enzyme-digested DNA for the presence of a HindIII-BamHI insert of approximately 240 bp, the size expected for the IGF-1 gene. One transformant with an insert of this size was used to prepare plasmid DNA designated pIGF101.

The 240 bpHindIII-BamHI fragment (250 ng) isolated from pIGF101, containing the IGF-1 gene, was inserted into the HindIII-BamHI site of plasmid pAO203 (10 ng), which contains DNA encoding an EcoRI site at the 5' end, the αMF pre-pro region, followed by nucleotides which encode the amino acids for three processing sites, lys-arg and (glu-ala)$_2$, and including a HindIII site at the 3' end. The resulting plasmid was used to transform *E. coli* MC1061 cells. Ampicillin-resistant colonies were selected and screened with an oligonucleotide complementary to sequence 162 to 132 of the IGF-1 gene, Sequence ID No. 1. One colony which was positive in this screen was selected and its plasmid designated pIGF102.

The EcoRI-BamHI fragment from pIGF102 (250 ng), containing the αMF pre-pro region and proteolytic processing sites, and IGF-1 gene, was cloned into M13mp19 (10 ng) and used to transform *E. coli* JM103 cells. The resulting transformants were screened by analysis of restriction enzyme-digested DNA, and one clone (pIGF103) with an insert of the correct size (480 bp EcoRI-BamHI fragment) was used to prepare single-stranded DNA for site-directed mutagenesis. Site-directed mutagenesis of the single-stranded DNA was performed to delete the (glu-ala)$_2$ spacer sites, the HindIII cloning site, the polylinker attached to the synthetic gene, and the codon for the initial methionine of IGF-1. Mutagenesis was accomplished using standard procedures and oligonucleotides having the following sequences:

mutagenizing oligonucleotide (Sequence ID No. 2):
5'-GTATCTTTGGATAAAAGAGGACCGGAGACGCTCTGC-3'
screening oligonucleotide (Sequence ID No. 3):
5'-ATAAAAGAGGACCGGA-3'.

Removal of the above noted sequences yielded a fusion gene containing DNA encoding the αMF pre-pro region and lys-arg processing site fused directly to the coding region of the IGF-1 gene.

The selected clone, designated pIGF104, was sequenced to verify the changes and then subjected to a second site-directed mutagenesis to insert an EcoRI site immediately following the translation termination codon of the IGF-1 gene. Oligonucleotides having sequences as follows were used in this mutagenesis:

mutagenizing oligonucleotide (Sequence ID No. 4):
5'-ATGCAGCTTGATAAGAATTCAAATGAGTCGACCTGCAGGC-3'
screening oligonucleotide (Sequence ID No. 5):
5'-TAAGAATTCAAATGAGT-3'.

The mutagenized clone was designated pIGF105.

After the second mutagenesis was confirmed by DNA sequencing, the αMF-IGF-1 gene fusion was isolated on a 450 bp EcoRI fragment, then 250 ng of this EcoRI fragment was inserted into 10 ng of the *P. pastoris* expression vector pAO815, which had been previously digested with EcoRI and treated with calf alkaline phosphatase. The resulting single-copy expression vector, pIGF201, contains one copy of the αMF-IGF-1 fusion gene under the transcriptional control of the Pichia pastoris AOX1 promoter and regulatory regions, as well as the AOX1 transcription termination and polyadenylation signals. In addition, the vector includes the Pichia pastoris HIS4 gene used for selection in His⁻ hosts and additional 3' AOX1 sequences which can be used to direct integration of the vector into the host genome. Plasmid pIGF201 is shown in FIG. 2.

The entire αMF-IGF-1 fusion gene and approximately 50 nucleotides each of the promoter and termination regions of pIGF201 were sequenced to verify that the nucleotide sequences were not altered during the cloning process.

2. Construction of expression vectors pIGF202, pIGF204, and pIGF206, which contain multiple copies of the expression cassette.

Figure 3:
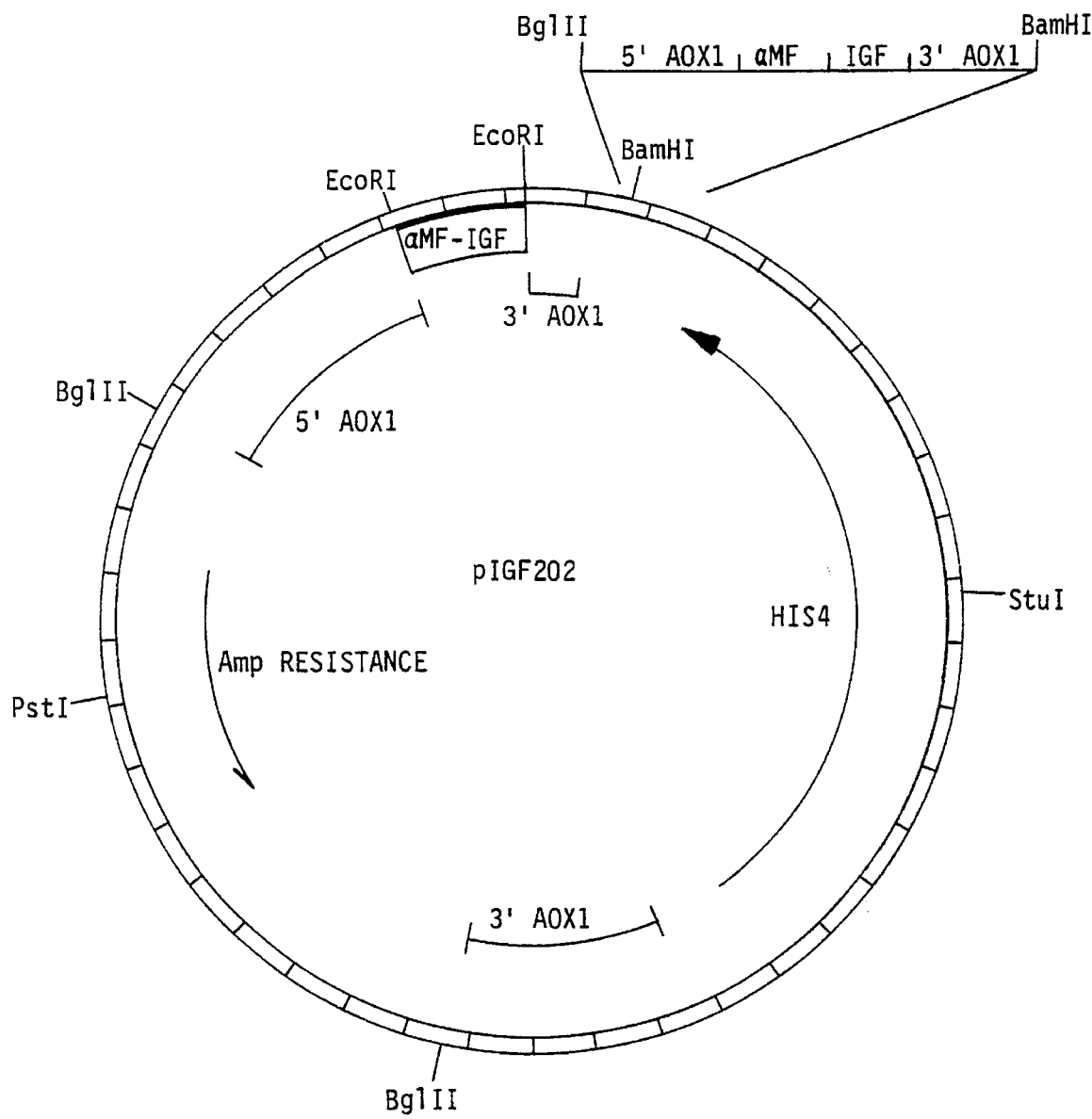
FIG. 3 is a restriction map of plasmid pIGF202.

The expression cassette containing the AOX1 promoter and regulatory region, the αMF-IGF-1 fusion gene, and the AOX1 transcription termination and polyadenylation signals was isolated from pIGF201 as a 1700 bp BglII-BamHI fragment. The BglII-BamHI expression cassette (250 ng) was inserted back into the unique BamHI site of pIGF201 (10 ng of BamHI digested, calf alkaline phosphatase-treated pIGF201). MC1061 cells were transformed with the ligation. Amp$^R$ colonies were selected and plasmid was characterized by restriction digest. Analysis of restriction enzyme digests of the resulting plasmid, pIGF202 shown in FIG. 3, verified that the two expression cassettes were joined as tandem-repeat units rather than inverted-repeat units: SalI digest yielded ~2100, 1750, and 6100 bp bands; ClaI/BamHI digest yielded ~3800 and 6450 bp bands.

Figure 4:
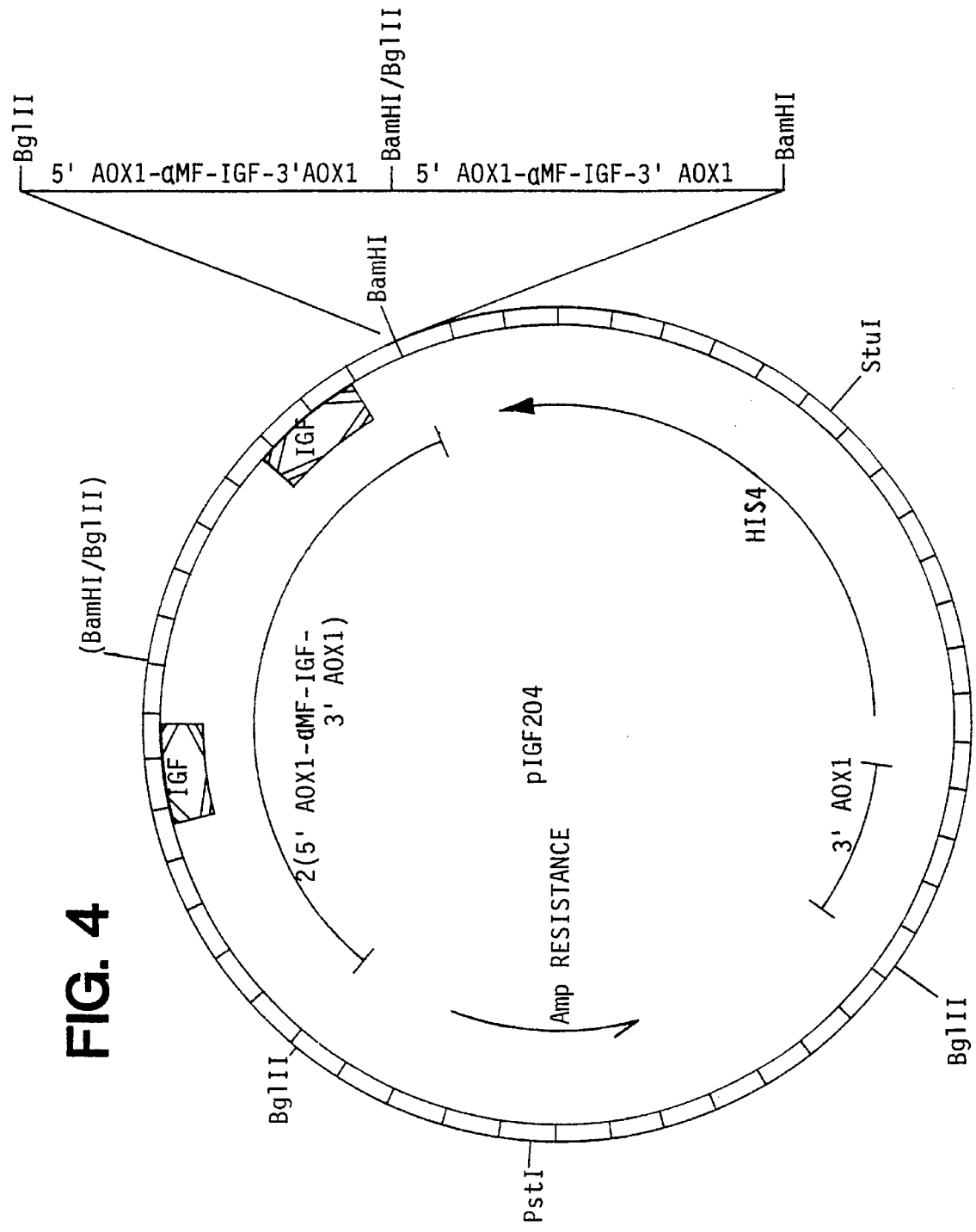
FIG. 4 is a restriction map of plasmid pIGF204.

The BglII-BamHI fragment from plasmid pIGF202, containing two copies of the expression cassette, was isolated (250 ng) and inserted back into the unique BamHI site in calf alkaline phosphatase-treated pIGF202 (10 ng) to yield vector pIGF204 shown in FIG. 4, containing four copies of the expression cassette. MC1061 cells were transformed with the ligation. Amp$^R$ colonies were selected and plasmid was characterized by restriction digest. Correct plasmid demonstrated ~6600 and 6900 bp bands upon digestion with ClaI and BamHI.

Figure 5:
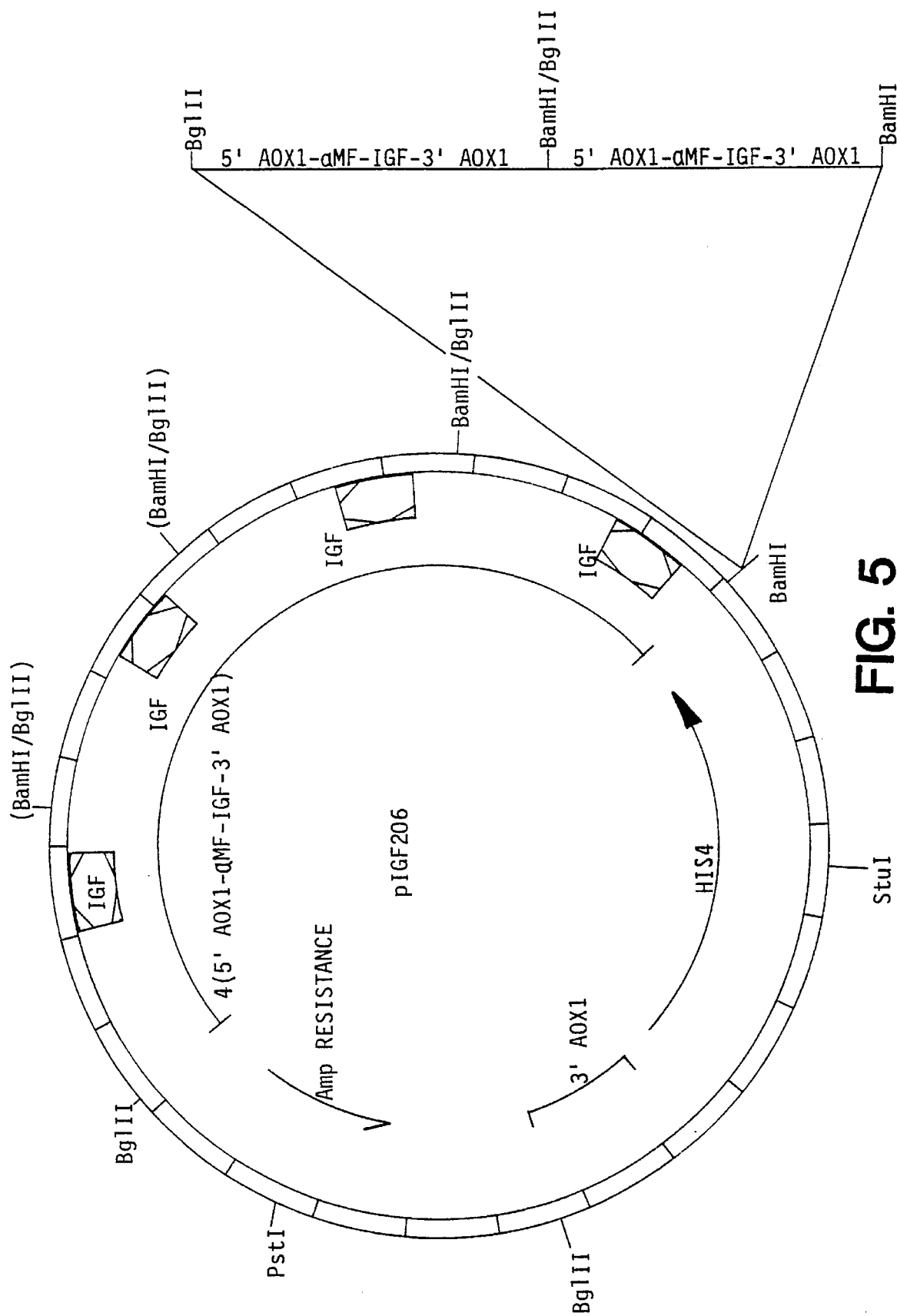
FIG. 5 is a restriction map of plasmid pIGF206.

To construct expression vector pIGF206, which contains six copies of the expression cassette, the BglII-BamHI fragment from pIGF202 (250 ng) was cloned into the BamHI site of pIGF204 (10 ng; pIGF204 had been previously treated with calf alkaline phosphatase). MC1061 cells were transformed with the ligation. Amp$^R$ colonies were selected and plasmid was characterized by restriction digest. Restriction digests of the vector DNA were examined to verify the number of expression cassettes and that the expression cassettes were joined as tandem-repeat units. Correct plasmid yielded bands of ~6600 and 10300 bp upon digestion with ClaI and BamHI. Plasmid pIGF206 is shown in FIG. 5.

B. Construction of expression vectors containing αMF prepro-lys-arg-glu-ala-IGF-1.

IGF-1 expression vectors containing DNA encoding the αMF prepro sequence, including the lys-arg and one glu-ala processing sequence, fused to the IGF-1 coding sequence were prepared from pIGF105, which contains the αMF prepro-lys-arg-IGF-1 fusion gene in M13mp19 (see Example 2.A.1). Site-directed mutagenesis of single-stranded DNA from pIGF105 was performed to insert codons for a glu-ala spacer site between the αMF prepro-lys-arg and IGF-1 DNA sequences. Mutagenesis was accomplished using standard procedures and oligonucleotides having the following sequences:

Mutagenizing oligonucleotide (Sequence ID No. 6)
5'-TCTTTTGGATAAAGAGAGGCTGGACCGCAGACGCTC-3'
Screening oligonucleotide (Sequence ID No. 7)
5'-AAAAGAGAGGCTGGACCGC-3'.

The selected clone was sequenced to verify that the DNA encoding the glu-ala residues was added correctly. The αMF prepro-lys-arg-glu-ala-IGF-1 gene fusion was isolated from the selected clone on a 465-bp EcoRI fragment and ligated to EcoRI-digested, alkaline phosphatase-treated vector pAO815. The resulting single copy expression vector, pIGF816, contains one copy of the αMF prepro-lys-arg-glu-ala-IGF-1 gene fusion under transcriptional control of the *P. pastoris* AOX1 promoter and regulatory regions, as well as the AOX1 transcription termination and polyadenylation signals. The vector also includes the *P. pastoris* HIS4 gene for selection in His⁻ hosts and additional AOX1 sequences. The entire αMF prepro-lys-arg-glu-ala-IGF-1 gene fusion and approximately 30 nucleotides each of the promoter and termination regions of pIGF816 were sequenced to verify that the sequences were not altered during the cloning process.

Expression vectors containing two or more copies of the αMF prepro-lys-arg-glu-ala-IGF-1 gene cassette can be prepared as described for construction of vectors containing multiple copies of the αMF prepro-lys-arg-IGF-1 gene expression cassette (see Example 2.A.2.).

Example 3

INTRODUCTION OF THE EXPRESSION CASSETTES FROM THE IGF-1 EXPRESSION VECTORS INTO STRAINS OF PICHIA PASTORIS

A. Mut⁺ strains

Expression vectors pIGF201, pIGF202, pIGF204, and pIGF206 and pIGF816 were used to develop IGF-1-expressing Mut⁺ strains of Pichia pastoris. The Mut phenotype refers to the methanol utilization ability of the strain. Mut⁺ strains consume methanol at a rate similar to that of wild-type strains. A His⁻ mutant of Pichia pastoris, GS115 (ATCC No. 20864), was used as the host for all transformations, which were accomplished by either the spheroplast method (performed as described in U.S. Pat. No. 4,879,231) or by the whole-cell lithium chloride yeast transformation system (Ito, et al. (1984) *Agric. Biol. Chem.* 48: 341) with modification necessary for adaptation to methylotrophic yeast, such as *P. pastoris* (see European Patent Application No. 312,934; also available as U.S. Pat. No. 4,929,535).

Mut⁺ strains were generated by integration of the entire expression vector into either the AOX1 or HIS4 locus of the host genome by an additive homologous recombination event. Plasmid pIGF201 was transformed into GS115 as an undigested circular vector and allowed to integrate randomly into the AOX1 locus at either the 5' or 3' regions homologous to sequences contained in the plasmid, or into the HIS4 locus. For site-directed addition to the HIS4 locus, the multi-copy expression vectors pIGF202, pIGF204, and pIGF206 and the single copy vector pIGF816 were digested with StuI, which linearizes the plasmids by cutting the vector within the HIS4 region. Additive integration at either the AOX1 or HIS4 locus does not disturb the AOX1 gene.

The Mut⁺ transformants resulting from additive integration of the expression plasmids, either randomly (pIGF201) or by site-direction (pIGF202, pIGF204, pIGF206 and pIGF816), were initially screened for histidine prototrophy. Prototrophic strains generated by separate transformation of GS115 with each of the four plasmids were selected for further analysis.

Ten of the His⁺ transformants resulting from transformation of GS115 with pIGF201 were analyzed by Southern blot hybridization to verify the site of integration of the expression plasmid and number of copies of the plasmid integrated. Chromosomal DNA from the 10 transformants was separately digested with EcoRI and BulII, separated by agarose gel electrophoresis, and transferred to nitrocellulose. The EcoRI digests were probed with pBR322-based plasmids containing either the AOX15' and 3' regions or the Pichia pastoris HIS4 gene. The BglII digest was probed with an oligonucleotide homologous to the IGF-1 gene.

Sixteen of the His⁺ transformants generated by transformation of GS115 with pIGF202, 16 generated by transformation with pIGF204, and 26 generated by transformation with pIGF206 were also analyzed by Southern blot hybridization to verify the site of integration and integrity of the multi-copy expression vector. Chromosomal DNA was digested with BglII and probed with plasmids containing the AOX1 5' and 3' regions or HIS4 gene, and also separately digested with StuI and probed with the oligonucleotide homologous to the IGF-1 coding sequence.

Analysis of DNA from ten pIGF201 transformants by Southern blot hybridization indicated that four transformants contained a single copy of the expression vector integrated at the AOX1 locus and two transformants contained multiple copies of the plasmid integrated at the HIS4 locus. The four other strains contained the plasmid integrated at unknown loci. It was not possible to determine the exact number of copies of the plasmid integrated at HIS4. Southern analysis of DNA revealed that 10 of the pIGF202 transformants, 9 of the pIGF204 transformants, and 13 of the 26 pIGF206 transformants contained a single copy of the respective expression vector integrated at HIS4. The other transformants contained plasmids integrated at unknown loci.

The following representative strains generated by transformation of GS115 with vectors pIGF201, pIGF202, pIGF204 or pIGF206 were selected for further analysis:

| Strain Name | Plasmid Integrated | Site of Integration | Number of Plasmids Integrated | Expression Cassette Copy Number |
|---|---|---|---|---|
| G+ IGF201S1 | pIGF201 | AOX1 | 1 | 1 |
| G+ IGF206S2 | pIGF206 | HIS4 | 2 | 6 |
| G+ IMB202S2 | pIGF202 | HIS4 | 1 | 2 |

| Strain Name | Plasmid Integrated | Site of Integration | Number of Plasmids Integrated | Expression Cassette Copy Number |
|---|---|---|---|---|
| G+ IMB204S14 | pIGF204 | HIS4 | 1 | 4 |
| G+ IMB206S1 | pIGF206 | HIS4 | 1 | 6 |

In addition, four strains generated by transformation with pIGF816, strains G+IGF816S1, G+IGF816S2, G+IGF816S9 and G+IGF816S11, were also analyzed further during growth in one-liter fermentations.

B. Mut⁻ strains

In Mut⁻ strains, the expression vector integrates into the AOX1 locus and disrupts it. Thus, Mut⁻ strains consume methanol at a much slower rate than Mut⁺ strains.

To generate Mut⁻ strains, plasmid pIGF206 was digested with BglII. This liberates a fragment comprised of the six IGF-1 expression cassettes, the HIS4 gene for selection, and the AOX1 3' region. Both ends of this fragment contain long sequences which are homologous to the 5' and 3' ends of the AOX1 locus. Upon transformation of GS115 hosts with the BglII-ended fragment, integration into the AOX1 locus by homologous recombination results in substitution of the BglII-ended fragment for the AOX1 structural gene. Positive transformants were selected by their His⁺ phenotype and by their Mut⁻ phenotype, slow growth on methanol. Selection is accomplished by plating His⁺ transformants on minimal glucose (2%) master plates to obtain colonies originating from single cells. After overnight incubation at 30° C., the masters were replica-plated to minimal glucose plates and plates containing no carbon source to which methanol was added in vapor phase. This is accomplished by adding approximately 200 μl of methanol to the Underside of the top of a covered petri dish. The plates were incubated at 30° C. for 4–6 days with additional methanol added in the vapor phase every two days. Colonies showing visible growth were scored as Mut⁺ and those with no visible, or slow, growth were scored as Mut⁻. Approximately 15% were slow growers, which is indicative of disruption of the AOX1 gene.

Following the initial screening for methanol utilization and histidine prototrophy, chromosomal DNA from three Mut⁻ transformants was analyzed by three different Southern blots to verify the site of plasmid integration and number of copies integrated.

Chromosomal DNA from Mut⁻ transformants was digested with EcoRI and probed with pBR322-based plasmids containing either the AOX1 5' and 3' regions or the Pichia pastoris HIS4 gene. An additional blot of BglII-digested DNA was probed with the plasmid containing the IGF-1 gene. Southern analysis of the three Mut⁻ transformants generated using plasmid pIGF206 revealed that all three contained a single copy of the BglII fragment, containing six expression cassettes, integrated by replacement at the AOX1 locus.

The strains were characterized as follows:

| Strain Name | Site of Integration | Number of Plasmids Integrated | Expression cassette copy number |
|---|---|---|---|
| G-IMB206S1 | AOX1 | 1 | 6 |
| G-IMB206S2 | AOX1 | 1 | 6 |
| G-IMB206S3 | AOX1 | 1 | 6 |

C. Preparation of protease-deficient strains for expression and secretion of IGF-1

The use of protease-deficient strains of *P. pastoris* hosts for recombinant expression of heterologous proteins susceptible to degradation by *P. pastoris* proteases is described in U.S. patent application No. 07/678,916. Protease-deficient *P. pastoris* strains have been generated by disrupting *P. pastoris* genes, such as PEP4 and PRB-1 that encode proteins that directly or indirectly affect protease activity of the cell. Disruption of these genes results in a reduction of at least a portion of the protease activities in the cell, including proteinase A, carboxypeptidase Y and proteinase B activities. Recombinant Pep4⁻ (also called pep4) and Pep4⁻Prb-1⁻ (also called pep4 prb-1) IGF-1-secreting strains of *P. pastoris* have been prepared.

Four protease-deficient IGF-1 expressing strains of *P. pastoris*, strains M+IMB206S1, M+IGF816S1, M+IGF816S4 and C+IGF816S1 were generated using two different approaches. Strain M+IMB206S1 was developed by transformation of a *P. pastoris* strain containing six copies of an αMF prepro-lys-arg-IGF-1 gene expression cassette (strain G+IMB206S1, see Example 3.A.) with a PEP4 gene disruption vector, pDR421. Vector pDR421 (described below and in detail in U.S. patent application Ser. No. 07/678,916) contains an internal portion of the *P. pastoris* PEP4 gene which integrates into the host genome at the PEP4 locus to generate two incomplete and nonfunctional copies of the PEP4 gene.

Strains M+IGF816 S1, M+IGF816S4 and C+IGF816S1 were generated by transforming protease deficient *P. pastoris* host strains with the αMF prepro-lys-arg-glu-ala-IGF-1 gene construct. Strains M+IGF816S1 and M+IGF-816S4 were generated by transformation of a pep4 host and C+IGFS16S1 by transformation of a pep4, prb-1 host.

1. Construction of the *P. pastoris* PEP4 gene disruption vector pDR421.

Plasmid pDR421 was constructed for use in the preparation of PEP4-deficient (Pep4⁻) strains of *P. pastoris* in which the host PEP4 gene is disrupted by addition of an incomplete PEP4 gene to the endogenous PEP4 locus. Plasmid pDR421 contains an internal portion of the PEP4 gene, which, when introduced into the host genome at the PEP4 locus, results in two incomplete and nonfunctional copies of the PEP4 gene.

To construct pDR421, the URA3 gene of *P. pastoris* was cloned into vector PEP205. Plasmid PEP205 contains pUC19 sequences and the portion of the PEP4 gene encoded by the approximately 450 bp BamHI fragment derived from pEP202. Plasmid pEP202 was prepared by inserting a 10.6 kb EcoRI fragment of the *P. pastoris* genome, that had been identified as containing the PEP4 gene by Southern blot hybridization of EcoRI-digested *P. pastoris* genomic DNA with the homologous *S. cerevisiae* PEP4 gene as a probe, into pUC19. The 10.6 kb fragment was isolated and approximately 200 ng of it was ligated with an equal amount of pUC19 which had been cut with EcoRI and dephosphorylated. The ligation mixture was used to transform *E. coli* strain MC1061. Ampicillin-resistant colonies were selected and screened by analysis of restriction enzyme digests of colony DNA for the presence of the diagnostic 10.6 kb EcoRI fragment. A large-scale plasmid preparation was made from a colony containing the correct plasmid, which was named pEP202. Plasmid pEP202 contains the complete *P. pastoris* PEP4.

The URA3 gene was isolated from SpeI/SphI digested pPU205 as a 2 kb fragment and ligated to XbaI/SphI-digested pEP205 and used to transform *E. coli* strain MC1061 to ampicillin resistance. Amp$^R$ colonies were screened by analysis of BamHI/SphI digested colony DNA for the presence of 2.7 kb, 0.4 kb and 1.9 kb fragments. A selected transformant that contained the correct plasmid construct was identified and the plasmid was designated pDR421.

2. Preparation of M+IMB206S1

M+IMB206S1, a pep4 IGF-1 expressing strain, was generated by transforming a pep4$^+$ *P. Pastoris* strain that contained six copies of an αMF prepro-lys-arg-IGF-1 construct with the PEP4 disruption vector pDR421, which contains an internal portion of the *P. pastoris* PEP4 gene and which integrates into the host genome at the PEP4 locus, thereby disrupting the gene locus by generating two incomplete and nonfunctional copies of the gene.

In order to facilitate identification of transformants that incorporated pDR421, an auxotrophic marker selection system was established in strain G+IMB206S1 prior to transformation. This was accomplished by isolation of a colony of G+IMB206S1 that, through spontaneous mutation, became auxotrophic for uracil (Ura-). Because pDR421 contains a *P. pastoris* URA3 marker gene, in addition to the PEP4 fragment, it was possible to initially select those cells of the Ura$^-$ derivative of G+IMB206S1 that had incorporated pDR421 on the basis of uracil prototrophy. The isolation of a Ura$^-$ IGF-1-expressing *P. pastoris* strain and its use in generating a pep4 IGF-1-expressing *P. pastoris* strain are described in this section.

a. Isolation of the Ura$^-$ IGF-1 expressing strain IGF-U.

Resistance to a 5-fluoro-orotic acid (5-FOA) was used as a means of identifying Ura$^-$ derivatives of strain G+IMB206S1. 5-FOA is an analog of a uracil biosynthetic pathway intermediate that, when metabolized by Ura$^+$ strains, yields a toxic compound. Therefore, Ura$^+$ strains cannot survive on 5-FOA-containing medium. In contrast, the uracil biosynthetic pathway of Ura$^-$ strains is blocked at certain steps, and such strains do not metabolize 5-FOA and are unaffected by its toxic effects. Consequently, plating cells on 5-FOA-containing medium can be used as a method to detect Ura$^{31}$ strains generated by spontaneous mutation.

A Ura$^-$ derivative of the IGF-1-producing strain G+IMB206S1 was isolated by direct plating of approximately 5×10$^7$ cells into a 5-FOA-containing medium supplemented with uracil (0.67% yeast nitrogen base, 2% agarose, 2% glucose, 750 mg/L of 5-FOA and 45 mg/L of uracil). After one week of incubation at 30° C., a colony growing on the plate was isolated. This colony, which required uracil to grow, was unable to complement a ura3 strain of *Pichia pastoris* and was designated IGF-U.

b. Transformation of IGF-U with pDR421

Plasmid pDR421 contains the Pichia URA3 gene and a small portion of the Pichia PEP4. gene. BglII-digested plasmid pDR421 was used to transform IGF-U using standard spheroplast transformation procedures. Digestion of pDR421 with BglII linearized the vector by cleaving it within the PEP4 gene fragment. Thus, the resulting linear DNA had 5' and 3' ends containing sequences from the PEP4 gene and a URA3 gene. Because the ends of this BglII fragment are homologous to adjacent sequences of the PEP4 gene, integration of the fragment in the genome of IGF-U was directed at the PEP4 locus via homologous recombination that resulted in disruption of the PEP4 locus. The URA3 gene of the integrated DNA fragment conferred a Ura$^+$ phenotype on the transformants that provided a marker for strains which were transformed.

Ura$^+$ transformants were subsequently analyzed for carboxypeptidase Y (CPY) activity using a colony overlay colorimetric screening procedure (Jones, E. (1977) *Genetics* 85: 23–33). Colonies which appeared to have low carboxypeptidase Y (CPY) activity based on the results of this assay were isolated, subcultured, and then rescreened using the overlay assay. One of these strains was designated M+IMB206S1.

3. Preparation of M+IGF816S1 and M+IGF816S4

Protease-deficient strains containing one or more copies of the αMF-prepro-lys-arg-glu-ala-IGF-1 gene expression cassette were generated by transformation of a Pep4$^-$ His4$^-$ strain of *P. pastoris,* designated MGP21, with pIGF816.

a. Generation of MGP21

The protease-deficient host strain MGP21 was generated by gene replacement methods, as described in U.S. patent application Ser. No. 678,916, in which the PEP4 gene is replaced with a defective pep4 gene. Briefly, a His4$^-$ Ura$^-$ *P. pastoris* strain (GS4-2), selected from cells of a His4$^-$ strain (GS115) that had been plated onto 5-FOA, was transformed with a linear fragment of a PEP4disruption vector designated pDR602 (see U.S. patent application Ser. No. 07/678,916). The linear fragment of pDR602 consisted of the *P. pastoris* URA3 gene flanked on each side with DNA coding for a portion of the *P. pastoris* PEP4 gene. Hemology between the ends of the fragment and the endogenous PEP4 gene of GS4–2 stimulated integration of the fragment at the PEP4 locus resulting in a gene replacement event in which the defective URA3-containing pep4 gene replaced the endogenous PEP4 gene. The resulting strain, MGP21, is His4$^-$ Ura$^-$ Pep4$^-$.

b. Transformation of MGP21

Strain MGP21 was transformed with StuI-digested pIGFS16 via the lithium chloride method. Because StuI cleaves pIGF816 in the HIS4 gene, the linear fragment was directed to integrate into the his4 locus of strain MGP21. Resulting transformants were screened for histidine prototrophy. Two of the strains were designated M+IGF816S1 and M+IGF816S4.

4. Preparation of strain C+IGF816S1

A pep4 prb-1 IGF-1-expressing strain of *P. pastoris* containing one copy of the αMF prepro-lys-arg-glu-ala-IGF-1 expression cassette was generated by transformation of a pep4 prb-1 ura3 his4 *P. pastoris* host strain, designated MG18, with pIGF816.

a. Generation of MG18

Strain MG18 was generated by disruption of the PRB-1 gene of the pep4 ura3 his4 *P. pastoris* strain GS4-2521-4-5 (see U.S. patent application Ser. No. 07/678,916 for a detailed description of the generation of GS4-2521-4-5 from the ura3 his4 strain GS4-2 via the intermediate strain GS4-2521-4). This was accomplished by transformation of GS4-2521-4-5 with the PRB-1 disruption vector pDR911. Vector pDR911 (described in U.S. patent application Ser. No. 678,916) contains an internal portion of the *P. pastoris* PRB-1 gene, which, when used to transform PRB-1 strains of *P. pastoris,* integrates into the host genome at the PRB-1 locus to generate two incomplete and non-functional copies of the PRB-1 gene. Vector pDR911 also contains a complete functional *P. pastoris* URA3 gene for use as a selectable marker in ura3 host strains of *P. pastoris,* such as GS4-2521-4-5.

Plasmid pDR911 was linearized by cleavage with BglII which cuts the plasmid within the fragment of the PRB-1 gene. The linear DNA was used to transform GS4-2521-4-5 according to the spheroplast method. Because the ends of this linear DNA are homologous to adjacent sequences of the PRB-1 gene, integration of the DNA into the genome of GS4-2521-4-5 was directed at the PRB-1 locus via a homologous recombination event resulting in the disruption of the PRB-1 locus. The URA3 gene of the integrated DNA fragment conferred a Ura$^+$ phenotype on the transformants that provided a marker for strains that had been transformed. Genomic DNA from transformants that were able to survive on media lacking uracil was analyzed by Southern blot hybridization. The DNA was digested with EcoRV, seperated by electrophoresis on a 0.75% agarose gel and transferred to nitrocellulose. The filter was probed with random-primed pDR911. The band pattern expected for a strain in which the PRB-1 gene had been disrupted was a loss of the 5 kb fragment representing the endogenous undisrupted PRB-1 gene and the appearance of an approximately 10 kb fragment representing the endogenous 5 kb PRB-1 fragment plus the 5 kb linear vector DNA pDR911. DNA from 3 out of 40 transformants exhibited this band pattern. One of these strains was MG18.

b. Transformation of MG18 with pIGF816

To develop pep4 prb-1 strains of *P. pastoris*, strain MG18 was transformed with. StuI-digested pIGFS16 by the lithium chloride method. Because StuI cleaves pIGF816 in the HIS4 gene, the linear fragment was directed to integrate into the his4 locus of strain MG18. Resulting transformants were screened for histidine prototrophy. One strain was designated C+IGF816S1.

Example 4

GROWTH OF STRAINS IN ONE- AND TEN-LITER FERMENTATIONS.

Medium employed in fermentations described herein had the following composition:

| Chemical | Grams/liter |
|---|---|
| A. 10x BASAL SALTS | |
| Phosphoric acid, 85% | 42.0 ml |
| Calcium Sulfate.2H20 | 1.8 |
| Potassium Sulfate | 28.6 |
| Magnesium Sulfate.7H20 | 23.4 |
| Potassium Hydroxide | 6.5 |
| B. $PTM_1$ TRACE SALTS | |
| Cupric Sulfate.5$H_2O$ | 6.0 |
| Sodium Iodide | 0.08 |
| Manganese Sulfate.$H_2O$ | 3.0 |
| Sodium Molybdate.2$H_2O$ | 0.2 |
| Boric Acid | 0.02 |
| Cobalt Chloride | 0.5 |
| Zinc Chloride | 20.0 |
| Ferrous Sulfate.7$H_2O$ | 65.0 |
| Biotin | 0.20 |
| Sulfuric Acid | 5.0 ml |

A. One-Liter Fermentations

In order to maximize expression and secretion of IGF-1, the effects of glycerol concentration and pH on IGF-1 production in one-liter fermentations have been investigated.

1. Mut$^+$ protocol:methanol fed-batch fermentation.

The Mut$^+$ fermentation protocol included three separate phases: (1) cells are initially cultured on glycerol in a batch mode; (2) following exhaustion of the glycerol, a limited glycerol feed is initiated such that glycerol does not accumulate, the AOX1 promoter is derepressed and cell mass increases: and (3) a methanol feed is initiated for production of heterologous protein in a methanol fed-batch mode.

Prior to use the fermentor was autoclaved with about one liter of medium containing 500 ml of 10x basal salts medium (final basal salts concentration of 5X, see above) and 30–50 g glycerol. After sterilization, 4 ml $PTM_1$ trace salts (see above) were added to the fermentor and the pH was adjusted to 5 with concentrated $NH_4OH$. In runs in which the pH was maintained at 5, pH was adjusted by addition of 50% $NH_4OH$ containing 0.1% Struktol J673 antifoam. Dissolved oxygen was maintained above 20% of saturation by regulating agitation and aeration, or supplementing the air feed with oxygen. In low pH fermentations in which the pH was maintained between 2.8 and 3.5, the pH controller was adjusted to the desired pH either at the initiation of the limited glycerol feed or at the initiation of the methanol feed and then allowed to decrease by virtue of cellular metabolism to the desired pH.

Inocula were prepared from buffered YNB glycerol plates and grown overnight at 30° C. in phosphate-buffered YNB (11.5 g/L $KH_2PO_4$, 2.66 g/L $K_2HPO_4$, 0.67% yeast nitrogen base, pH 6)) containing 2% glycerol. The fermentor was inoculated with these cultured cells, which had grown to an $OD_{600}$ of 1–6, and the batch growth regimen was continued for 18 to 24 hours. At the point of glycerol exhaustion, indicated by increased dissolved oxygen, a glycerol feed (50% glycerol plus 12 ml/l of $PTM_1$) was initiated at a rate in the range of about 5–20 ml/h. This period of growth on limited glycerol was continued until a total volume of approximately 40–300 ml of feed was added to the fermentor. After addition of the glycerol feed, a methanol feed (100% methanol plus 12 ml/L $PTM_1$) was started. The initial rate of methanol addition was approximately 1–2 ml/h. The methanol feed rate was increased for 3 to 8 hours to 5–6 ml/h. In some fermentations the feed rate was directly increased to a rate of 6 ml/h after three hours of methanol feeding. The vessel was harvested 40–95 hours following initiation of methanol induction.

2. Mut$^-$ protocol methanol fed-batch fermentation (Run 657).

The first two phases of the methanol fed-batch fermentations of the Mut$^-$ strains were conducted as described for the Mut$^+$ strain fermentations in Example 4(A)(1). However, the methanol induction phases of the Mut$^+$ and Mut$^-$ fermentation protocols differed in terms of the manner in which the methanol feeds were added to the cultures. In standard fermentations of the Mut$^-$ strain, the methanol feed rate was adjusted to maintain an excess of methanol in the medium which did not exceed 0.3% (as determined by gas chromatography). The methanol feed was initiated at 1 ml/hr and after two hours was increased in 10% increments every 30 minutes to a rate of 3 ml/hr which was maintained for the duration of the fermentation. The vessel was then harvested after 101 hours of growth of the strain on methanol.

B. Ten-Liter Fermentations

1. Fed-batch a. Standard methanol feed rate (Runs 843, 959, 960, 962, 968 and 999).

A 15-liter fermentor containing 3.5 liters 10X basal salts and 220 g glycerol brought to a total volume of 5.5 liters by the addition of water was sterilized. After the fermentor had cooled, 24 ml $PTM_1$ trace salts were added and the pH was adjusted to 5.0 with the addition of 28% ammonium hydroxide. The pH of the fermentation was maintained by addition of the same solution and foaming was controlled with the addition of a 5% solution of Struktol J673 Temperature was maintained at 30° C., and dissolved oxygen was maintained above 20% of saturation by regulating agitation, aeration, and reactor pressure or by supplementing the air feed with oxygen.

Inocula were prepared from cells grown overnight in buffered YNB (11.5 g/L $KH_2PO_4$, 2.66 g/l $K_2HPO_4$, 6.7 g/L yeast nitrogen base, pH 6) containing 2% glycerol. The fermentor was inoculated with 500–700 ml of the cultured cells which had grown to a concentration of 2–8 $OD_{600}$, and the batch growth regimen was continued for 18–24 hours until glycerol was exhausted. At the point of glycerol exhaustion, indicated by an increase in dissolved oxygen, a glycerol feed (50% w/v glycerol plus 12 ml/L $PTM_1$) was initiated at 100 ml/hr. After four hours, the glycerol feed was terminated and a methanol feed (100% methanol plus 12 ml/L $PTM_1$) was initiated at a rate of 20 ml/hr. After 3–4 hours of methanol feeding, the methanol feed rate was increased to 60 ml/hr and maintained at this rate for the remainder of the fermentation. The vessel was harvested approximately 72 hours after the initiation of the methanol feed.

In pH 5 fermentations, the pH of the culture was maintained at 5 throughout the fermentation. In low pH fermentations (i.e., pH 2.8–3.0), the set point of the pH controller was adjusted to the target pH and the pH of the culture was allowed to decrease to the new set point as a result of cellular metabolism. In some fermentations, the set point of the pH controller was adjusted at the initiation of the glycerol feed, whereas in other fermentations, the pH set point was not lowered until initiation of the methanol feed.

b. Modified methanol food rates (Runs 789, 810 and 906),

Additional 10-liter fermentations were conducted essentially as described in Example 4.B.1.a. except with modified methanol feed rates. In Run 789, the methanol feed rate was steadily increased as the cell density increased during the fermentation. After the initial three hours of methanol feeding at 20 ml/hr, the feed rate was increased to 30 ml/hr. The feed rate was then increased twice daily in proportion to the increase in cell mass.

In Run 810, the methanol feed rate was increased to 60 ml/hr after an initial four hours at 20 ml/hr. After 21 hours of methanol feeding, the feed rate was then increased to 100 ml/hr and maintained at the rate for the remainder of the fermentation (51 hours).

In Run 906, a methanol feed rate of 40 ml/hr was maintained for the first 60 hours of feeding, and then increased to 60 ml/hr for the remainder of the fermentation (90 hours total).

2. Continuous culture (Run 929),

In Run 929, the fermentation process was switched from a fed-batch to a continuous mode after 20 hours of methanol feeding. This was accomplished by initiating a 3X basal salts feed along with the methanol feed and maintaining a constant volume in the fermentor by continuous removal of whole broth (including cells). The methanol feed was maintained at a constant rate of 70 ml/hr and the basal salts feed rate was set at 70% of the total feed (i.e., methanol plus basal salts) rate. Thus, a total feed of 230 ml/hr, containing 30% methanol, was fed into the fermentor with a constant total volume of 8 liters. Continuous culture was carried out for 139 hours (total of 159 hours on methanol).

C. Results

Samples (15-ml aliquots) of the fermentor culture were removed from the fermentor at various times throughout the course of the fermentation. Aliquots of each sample were centrifuged at 6500 x g for 5 min to separate broth and cells. The levels of the $NH_4OH$, antifoam, glycerol and methanol reservoirs were recorded at these time points. Methanol and ethanol concentrations in the supernatant were determined by gas chromatography using a PorapakQ column (Alltech, Deerfield, Ill.).

In addition, the wet weight of the culture was determined as an indicator of cell growth in the fermentor. For this purpose a one-ml aliquot of the fermentor culture was centrifuged for four minutes in a microfuge, the supernatant was decanted, and the wet pellet was weighed.

The IGF-1 levels of the cell-free broth were determined by RIA, quantitative immunoblot or reverse-phase HPLC (see Example 5 for a description of each of these methods). The results of fermentations of the IGF-1-expressing strains of P. pastoris are provided in the Tables I–V.

TABLE I

Results of Quantitative Immunoblot Analyses
of Cell-Free Broth
from One-Liter Fermentations

| RUN | STRAIN NAME | EXPRESSION CASSETTE COPY NUMBER | pH | GLYCEROL ADDED (g) | CELL DENSITY WET WEIGHT (g/L) GLYCEROL | MeOH | HOURS ON MeOH | IGF-1 (mg/L) |
|---|---|---|---|---|---|---|---|---|
| 573 | G+IGF201S1 | 1 | 5 | 100 | 224 | 308 | 49 | 11 |
| 576 | G+IGF206S2 | 6 | 5 | 100 | 198 | 280 | 49 | 117 |
| 578 | G+IGF206S2 | 6 | 3.5[a] | 150 | 328 | 360 | 101 | 284 |
| 596 | G+IGF206S2 | 6 | 3[b] | 150 | 306 | 385 | 48 | 555 |
| 598 | G+IGF206S2 | 6 | 3.5[b] | 150 | 298 | 363 | 64 | 455 |
| 605 | G+IGF201S1 | 1 | 3[b] | 150 | 306 | 415 | 64 | 21 |
| 613 | G+IGF206S2 | 6 | 3[b] | 150 | 304 | 344 | 70 | 489 |

[a]The pH was decreased from 5 ro 3.5 after 26 hours of growth on methanol.
[b]The pH was decreased from 5 to the indicated pH at the initiation of the glycerol fed-batch phase.

TABLE II

Results of IncStar Antisera-Based RIAs of
Cell-Free Broth from One-Liter Fermentations

| RUN | STRAIN NAME | EXPRESSION CASSETTE COPY NUMBER | pH | GLYCEROL ADDED (g) | CELL DENSITY WET WEIGHT (g/L) | | HOURS ON MeOH | IGF-1 (mg/L) |
|---|---|---|---|---|---|---|---|---|
| | | | | | GLYCEROL | MeOH | | |
| 596 | G+IGF206S2 | 6 | 3 | 150 | 306 | 385 | 48 | 1850 |
| 605 | G+IGF201S1 | 1 | 3 | 150 | 306 | 415 | 64 | 167 |
| 657 | G-IMB206S3 | 6 | 3 | 150 | 278 | 370 | 101 | 745 |
| 661 | G+IMB206S1 | 6 | 3 | 150 | 267 | 320 | 73 | 1280 |
| 680 | G+IMB202S2 | 2 | 3 | 150 | 270 | 430 | 73 | 740 |
| 691 | G+IMB204S14 | 4 | 3 | 150 | 265 | 350 | 92 | 1400 |
| 694 | G+IMB206S1 | 6 | 5 | 150 | 254 | 325 | 94 | 306 |

TABLE III

Results of Nichols RIAs of Cell-Free
Broth from One-Liter Fermentations

| RUN | STRAIN NAME | EXPRESSION CASSETTE COPY NUMBER | pH | GLYCEROL ADDED (g) | CELL DENSITY WET WEIGHT (g/L) | | HOURS ON MeOH | IGF-1 (mg/L) |
|---|---|---|---|---|---|---|---|---|
| | | | | | GLYCEROL | MeOH | | |
| 661 | G+IGF206S1 | 6 | 3 | 150 | 267 | 320 | 73 | 140 |
| 680 | G+IMB202S2 | 2 | 3 | 150 | 270 | 430 | 73 | 64 |
| 691 | G+IMB204S14 | 4 | 3 | 150 | 265 | 350 | 92 | 174 |
| 694 | G+IMB206S1 | 6 | 5 | 150 | 254 | 325 | 94 | 15 |
| 755 | G+IMB204S14 | 4 | 2.8 | 50 | 160 | 460 | 72 | 300 |
| 756 | G+IMB204S14 | 4 | 2.8 | 175 | 314 | 445 | 72 | 315 |
| 757 | G+IMB204S14 | 4 | 2.8 | 80 | 201 | 491 | 72 | 300 |
| 772 | G+IMB206S1 | 6 | 2.8 | 85 | 181 | 401 | 71 | 335 |
| 773 | G+IMB204S14 | 4 | 2.8 | 90 | 200 | 377 | 70 | 250 |
| 775 | G+IMB204S14 | 4 | 2.8 | 40 | 104 | 409 | 70 | 280 |
| 776 | G+IMB206S1 | 6 | 2.8 | 45 | 116 | 490 | 71 | 355 |

TABLE IV

Results of HPLC Analyses of Cell-Free
Broth from One-Liter Fermentation[a]

| RUN | STRAIN NAME | EXPRESSION CASSETTE COPY NUMBER | pH | GLYCEROL ADDED (g) | CELL DENSITY WET WEIGHT (g/L) | | HOURS ON MeOH | IGF-1[b] (mg/L) |
|---|---|---|---|---|---|---|---|---|
| | | | | | GLYCEROL | MeOH | | |
| 605 | G+IGF201S1 | 1 | 3 | 150 | 306 | 415 | 64 | 14 |
| 680 | G+IMB202S2 | 2 | 3 | 150 | 270 | 430 | 73 | 39 |
| 691 | G+IMB204S14 | 4 | 3 | 150 | 265 | 350 | 92 | 101 |
| 694 | G+IMB206S1 | 6 | 5 | 150 | 254 | 325 | 94 | 3 |
| 757 | G+IMB204S14 | 4 | 2.8 | 80 | 201 | 491 | 72 | 74 |
| 772 | G+IMB206S1 | 6 | 2.8 | 85 | 181 | 401 | 71 | 121 |
| 934 | M+IMB206S1 | 6 | 2.8 | 50 | 132 | 450 | 72 | 139 |
| 935 | M+IMB206S1 | 6 | 5.0 | 50 | 123 | 363 | 72 | 167 |
| 943 | G+IMB204S14 | 4 | 5.0 | 50 | 125 | 330 | 72 | 0 |
| 1039 | G+IGF816S1 | 1[c] | 3.0 | 50 | 158 | 320 | 49 | 16 |
| 1047 | M+IGF816S1 | 1[c] | 3.0 | 50 | 123 | 282 | 69 | 16 |
| 1048 | G+IGF816S2 | 1[c] | 3.0 | 50 | 134 | 447 | 69 | 17 |
| 1049 | G+IGF816S9 | multi[c] | 3.0 | 50 | 131 | 380 | 69 | 44 |
| 1050 | G+IGF816S11 | multi[c] | 3.0 | 50 | 131 | 386 | 94 | 9 |
| 1053 | M+IGF816S4 | multi[c] | 3.0 | 50 | 143 | 393 | 70 | 33 |
| 1055 | C+IGF816S1 | 1[c] | 3.0 | 50 | 143 | 312 | 70 | 20 |
| 1066 | C+IGF816S1 | 1[c] | 5 | 50 | 123 | 234 | 70 | 20 |
| 1067 | M+IGF816S4 | multi[c] | 5 | 50 | 132 | 331 | 70 | 50 |
| 1069 | G+IGF816S11 | multi[c] | 5 | 50 | 132 | 323 | 70 | 0 |

TABLE IV-continued

Results of HPLC Analyses of Cell-Free Broth from One-Liter Fermentation[a]

| STRAIN RUN NAME | EXPRESSION CASSETTE COPY NUMBER | pH | GLYCEROL ADDED (g) | CELL DENSITY WET WEIGHT (g/L) | | HOURS ON MeOH | IGF-1[b] (mg/L) |
|---|---|---|---|---|---|---|---|
| | | | | GLYCEROL | MeOH | | |

[a]Cell-free broth was passed through a cation exchange chromatography column prior to analysis by HPLC (see Example 4C).
[b]Concentration of authentic IGF-1 (i.e., intact, correctly folded monomeric IGF-1).
[c]The number of expression cassettes contained in these strains is estimated based on IGF-1 expression levels.

TABLE V

Ten-Liter Fermentations

| STRAIN RUN NAME | EXPRESSION CASSETTE COPY NUMBER | pH | GLYCEROL ADDED (g) | CELL DENSITY WET WEIGHT (g/L) | | HOURS ON MeOH | IGF-1 (mg/L) |
|---|---|---|---|---|---|---|---|
| | | | | GLYCEROL | MeOH | | |
| 789 G+IGF204S14 | 4 | 2.8[a] | 420 | 107 | 584 | 60 | 290[c]/90[d] |
| 810 G+IMB204S14 | 4 | 2.8[a] | 420 | 181 | 595 | 51 | 305[c]/75[d] |
| 843 G+IMB204S14 | 4 | 2.8[a] | 420 | 177 | 482 | 72 | 308[c]/103[d] |
| 906 G+IMB204S14 | 4 | 2.8[a] | 420 | 178 | 471 | 90 | 300[c]/93[d] |
| 929 G+IMB204S14 | 4 | 2.8[a] | 420 | 180 | 400–480 | 159[b] | 55–70[d] |
| 959 M+IMB206S1 | 6 | 5.0 | 420 | 217 | 383 | 75 | 54[d] |
| 960 M+IMB206S1 | 6 | 2.8[a] | 420 | 184 | 387 | 72 | 138[d] |
| 962 G+IMB204S14 | 4 | 2.8[a] | 420 | 188 | 536 | 72 | 77[d] |
| 999 M+IMB206S1 | 6 | 3.0[a] | 420 | 191 | 398 | 72 | 131[d] |

[a]The pH was decreased from 5 to 2.8 at the initiation of the glycerol fed-batch phase.
[b]Continuous culture.
[c]Determined by Nicole RIA of cell-free broth (see Example 5A).
[d]Authentic IGF-1 levels determined by HPLC analysis of pretreated cell-free broth (see Example 5A).
[e]The pH was decreased from 5 to the indicated pH at the initiation of the methanol fed-batch phase.

As shown in Tables I–V, the four different assays used to measure IGF-1 levels yielded inconsistent results. As discussed in Example 5, the different assays most likely detect different combinations of the several species of IGF-1 present in varying concentrations in *P. pastoris* broth, including: intact correctly folded monomeric IGF-1, referred to as authentic IGF-1; multimeric IGF-1; nicked IGF-1; and incorrectly folded IGF-1; thereby providing differing values for IGF-1 concentrations of the broth. It is possible, however, to compare the IGF-1 levels of different fermentations when they are measured by the same assay. Such analyses yield the following conclusions.

The results of quantitative immunoblot analyses of fermentations of the six-copy strain G+IGF206S2 (Runs 576, 578, 596, 598 and 613) and the one-copy strain G+IGF201S1 (Runs 573 and 605) are shown in Table I. All samples quantified by immunoblot were first reduced with dithiothreitol (DTT), which disrupts disulfide bonds holding together multimerle or nicked IGF-1. Therefore, because only the protein that co-migrated with IGF-1 standard was quantified in this assay (see Example 5A), this method detected, but did not distinguish authentic monomer IGF-1, misfolded monomer IGF-1 and multimer IGF-1. The results shown in Table I demonstrate that expression cassette copy number has an effect on the level of immunoreactive IGF-1 contained in the broth, IGF-1 levels increase as the number of copies of the expression cassette contained in the strain increases (compare run 605 of the one-copy strain (21 mg/l) and Run 613 of the six-copy strain (489 mg/l)). A comparison of the IGF-1 levels of broth from fermentations conducted entirely at pH 5 (Runs 573 and 576) and the levels from fermentations conducted at lower pH (pH decreased from 5 to 3–3.5 at either initiation of glycerol feed (Runs 598, 605 and 613) or during methanol fed batch phase (Run 578)) reveals that the greatest amount of immunoreactive IGF-1 was obtained when the fermentation was conducted at lower pH. Furthermore, the time at which the pH was lowered from 5 to ≦3.5 also had an effect on IGF-1 levels. Lower IGF-1 levels were obtained when the pH of the fermentation was decreased later in the fermentation, i.e., during the methanol fed batch phase (compare Runs 598 and 578). The results of several fermentations of the six-copy strain conducted according to the same protocol (addition of 150 g of glycerol, 60–70 hours of methanol feeding, and decrease in pH from 5 to 3 at the initiation of glycerol feeding) demonstrated the of the IGF-1 production process, since all fermentations typically yielded between approximately 350–480 mg/l).

The results of Incstar antisera-based RIAs (Table II; see Example 5A for a description of this assay) of broth from fermentations of the six-copy strain G+IMB206S1 (Run 661), the four-copy strain G+IMB204S14 (Run 691), the two-copy strain G+IMB202S2 (Run 680) and the one-copy strain G+IGF201S1 (Run 605) further illustrate the dramatic effect of expression cassette copy number on IGF-1 expression by *P. pastoris*. The four-and six-copy strains produced similar levels of RIA-reactive IGF-1 (1400 and 1280 mg/l, respectively). and 2- and nearly 10-fold more IGF-1 than the two- and one-copy strains (740 and 167 mg/l, respectively). Furthermore, the Mut$^+$ six-copy strain G+IMB206S1 appeared to be superior to the Mut$^-$ six-copy strain (G-IMB206S3) in terms of IGF-1 production capability (compare Runs 661 and 657). Incstar antisera-based RIAs of broth from Runs 661 and 694 (strain G+IMB206S1) were in agreement with the finding that pH 5 fermentations yield significantly lower levels of IGF-1 than low pH fermentations.

Although Nichols RIAs consistently yielded lower values for IGF-1 expression levels than the Incstar antisera-based RIA, the relative IGF-1 levels from different fermentations, as measured by Nichols RIA, were in agreement with those as measured by Incstar antisera-based RIAs. For instance, a comparison of the IGF-1 levels of fermentations of the two-, four-, and six-copy strains G+IMB202S2 (Run 680), G+IMB204S14 (Ru$_n$ 691) and G+IMB206S1 (Run 661), respectively, as determined by Nichols RIA, further demonstrated the effect of expression cassette copy number on IGF-1 expression levels. Furthermore, the level of IGF-1 product determined by Nichols RIA was significantly higher in fermentations conducted at lower pH: compare Run 694 (pH 5; 15 mg/l) and Run 661 (pH 3; 140 mg/l) and Run 776 (pH 2.8; 355 mg/l). Finally, it appears that changing the amount of glycerol added during the glycerol batch and fed batch phases had little effect on the final IGF-1 concentration from fermentations of the four-and six-copy strains (compare Runs 772 (85 g glycerol added) and 776 (45 g glycerol added) which both produced approximately 345 mg/l; also compare Runs 755, 756, 757, 773 and 775 (glycerol added carried from 40–175 g) which yielded 250–300 mg/l.

HPLC analysis (see Example 5C) of fermentation broth permitted distinction and accurate measurement of each species of IGF-1 present in the broth. Table IV lists the levels of authentic IGF-1, as determined by reverse-phase HPLC of broth from one-liter fermentations of IGF-1-expressing strains of *P. pastoris*. The results of these HPLC analyses are consistent with those of RIA and immunoblot analyses of broth in terms of the relative IGF-1 levels in broth from different strains grown under different conditions. As shown in Table IV, expression cassette copy number clearly influences IGF-1 expression levels (compare IGF-1 levels of broth from a one-copy strain, G+IGF201S1 (14 mg/l, Run 605), a two-copy strain, G+IMB202S2 (39 mg/l, Run 680), a four-copy strain, G+IMB204S14 (101 mg/l, Run 691) and a six-copy strain, G+IMB206S1 (121 mg/l, Run 772)). In addition, the results in Table IV demonstrate the effect of pH on production of IGF-1 in *P. pastoris*; fermentations of strains G+IMB206S1 and G+IMB204S14 conducted at pH 5 (Runs 694 and 943, respectively) yielded essentially no authentic IGF-1 (or any form of IGF-1); whereas 121 and 74 mg of IGF-1/l were produced in low pH fermentations of these strains (Runs 772 and 757, respectively, pH was decreased from 5 to 2.8 at the initiation of the glycerol fed batch phase). The results of HPLC analysis of broth from several different low pH fermentations of strain G+IMB204S14 in which the amount of glycerol added to the fermentor varied between 40 and 175 g confirmed the finding that differing glycerol levels in this range had no effect on IGF-1 production; all fermentations yielded 70–110 mg/l.

The broth from one-liter fermentations of the protease-deficient (pep4) strain M+IMB206S1 was also analyzed by HPLC. As shown in Table IV, pH 5 and low pH fermentations (Runs 935 and 934, respectively) of this strain yielded similar high levels (167 and 139 mg/l, respectively) of authentic IGF-1. Furthermore, the level of authentic IGF-1 produced in these fermentations of strain M+IMB206S1 was approximately 60% higher than that produced in pH 2.8 fermentations of the four copy strain PEP4 G+IMB204S14 (Run 757; 74 mg/l) and approximately 15% higher than that produced in pH 2.8 fermentations of the six-copy PEP4 strain G+IMB206S1 (Run 772; 121 mg/l).

The results of HPLC analysis of broth from one-liter fermentations of strains containing one or more αMF pre-pro-lys-arg-glu-ala-IGF-1 expression cassettes are also shown in Table IV. These strains showed two different levels of IGF-1 expression. Strains G+IGF816S1 and G+IGF816S2 yielded similar levels of authentic IGF-1 (approximately 16 mg/l) in two identical fermentations (Runs 1039 and 1048). In contrast, strains G+IGF816S9 and G+IGF816S11 produced three-fold more authentic IGF-1 (approximately 45 mg/l) in Runs 1049 and 1050. Therefore, it appears that strains G+IGF816S9 and G+IGF816S11 fortuitously incorporated 2–3 copies of the αMF prepro-lys-arg-glu-ala-IGF-1 expression cassette into their genomes; whereas strains G+IGF816S1 and G+IGF816S2 apparently contain a single copy of the expression cassette.

Broth from fermentations of protease-deficient strains M+IGF816S1 (pep4), M+IGF816S4 (pep4) and C+IGF816S1 (pep4 prb-1) containing one or more αMF prepro-lys-arg-glu-ala-IGF-1 expression cassettes (see Example 2C) also was analyzed by HPLC. Based on the authentic IGF-1 levels of the broth from low pH fermentations of strains M+IGF816S1 and C+IGF816S1 (Runs 1047 and 1055, 16–20 mg/l) as compared to those of the broth from low pH fermentations of strain M+IGF816S4 (Run 1053, 33 mg/l), it appears that strains M+IGF816S1 and C+IGF816S1 contain one copy of the expression cassette; whereas M+IGF816S4 contains two or more expression cassettes. It is noteworthy that pH 5 fermentations of these strains (Runs 1066 and 1067) yielded at least as much authentic IGF-1 as low pH fermentations of these strains. In contrast, pH 5 fermentations of a PEP4 strain containing multiple copies of the αMF-lys-arg-glu-ala-IGF-1 expression cassette (Run 1069) yielded no authentic IGF-1.

As shown in Table V, high-level production of IGF-1 by *P. pastoris* was readily scaled up to the 10-liter fermentation level. A comparison of low pH 10-liter fermentations of the four-copy strain G+IMB204S14 conducted with varying methanol feed rates (Runs 789, 810, 843, and 906) revealed similar levels of authentic IGF-1 production. A significant level of authentic IGF-1 (54 mg/l) was produced in a pH 5.0 10-liter fermentation of the pep4 Strain M+IMB206S1 (Run 959). This level was increased in 10-liter fermentations of this strain that were initiated at pH 5 and then conducted at pH 2.8 or 3.0 during the entire methanol fed batch phase (Runs 960 and 999, respectively). A similar fermentation of strain G+IMB204S14 (Run 962) yielded IGF-1 levels equivalent to those obtained in a fermentation in which the initial pH of 5 was decreased to 2.8 upon initiation of the glycerol fed batch phase (Runs 789, 810, 843 and 906). Continuous culture of strain G+IMB204S14 (Run 929) produced between 55 and 70 mg/l of authentic IGF-1 at a rate of 230 ml of culture media per hour. Therefore, the productivity of continuous culture fermentations was slightly higher than that of fed-batch fermentations.

EXAMPLE 5

MEASUREMENT OF IGF-1 CONCENTRATIONS IN THE CULTURE MEDIUM

A. RIA Assay.

A 1:5000 final dilution of rabbit anti-human IGF-1 antisera (Incstar anti-somatomedin C antibody, catalog #22275), 10,000–12,000 cpm of $^{125}$I-IGF-1 (Incstar catalog #22303), and various dilutions of recombinant human IGF-1 standard (purchased from Imcera and quantified by amino acid analysis) or the unknown broth solution were incubated overnight at 4° C. in a final volume of 0.5 ml in 12×75 mm polystyrene tubes. At the end of the incubation, 100 µl of Pansorbin (working dilution of 1:40) was added to the tubes and incubated for 15 minutes at room temperature. Two milliliters of RIA buffer (50 mM NaPO$_4$, 0.1% BSA, 0.1% NaN$_3$, and 0.1% Triton X-100, pN 7.4) were added to each tube before centrifugation at 3200 rpm for 68 minutes at 4° C. in a Beckman J6M centrifuge. Following centrifugation, the supernatant was decanted and the radioactivity associated with the pelleted material was determined in a gamma counter.

Alternatively, some of the samples were assayed using a commercial RIA (Nichols Institute Diagnostic; San Juan Capistrano, Calif.). The Nichols assay consistently measured lower levels for IGF-1 than the RIA described above (see data above from Runs 661, 680, 691 and 694). This apparent discrepancy probably arises because the antibody used in the RIA described above detects both monomer and multimer IGF-1, whereas the antibody used in the Nichols assay most likely detects monomer IGF-1 only.

B. Western blot

Immunoblot analysis of *P. pastoris* fermentation broth was used to qualitatively and quantitatively evaluate IGF-1 production in *P. pastoris*.

Several dilutions of recombinant human IGF-1 standard (Imcera) and samples of cell-free broth obtained at the conclusion of selected fermentations of the Mut$^+$ and Mut$^-$ IGF-1-expressing strains of Pichia pastoris were analyzed by quantitative western blots to estimate the amount of immuno-reactive IGF-1 contained in the broth. The proteins were first separated by Tricine SDS-PAGE (Schagger, H. and yon Jagow, G. (1987) *Anal. Biochem.* 117: 304–310) and then transferred to 0.1 µm nitrocellulose by electroblot in a solution of Towbin buffer (25 mM Tris-HCl, pH 8.3, 190 mM glycine, 20% methanol) for at least 90 minutes at 20 V/cm. After the proteins were transferred onto nitrocellulose, the filter was incubated for one hour in blocking buffer (0.25% gelatin, phosphate-buffered saline, 0.05% Tween 20, 0.02% sodium azide). Rabbit anti-IGF-1 antisera 10A was diluted 1:2000 with blocking buffer and incubated with the filter for a minimum of two hours. Antibody 10A was raised against a synthetic peptide corresponding to the last 14 amino acids of the carboxy terminus of human IGF-1, which was conjugated to human α-globulin. The antisera was adsorbed to α-globulin prior to use. The filter was washed with blocking buffer for an hour and incubated with $^{126}$I-Protein A (0.02 µCi/ml) for 45 minutes. After one hour of washing with blocking buffer, the filter was air dried and exposed to X-ray film with an intensifying screen at −75° C. To estimate the IGF-1 content of broth, the intensities of bands corresponding to IGF-1 in lanes containing broth were compared to the intensities of bands corresponding to different known amounts of IGF-1 standard. Autoradiographs were used as templates and the portions of the gels corresponding to bands were excised and the radioactivity in the bands counted in a scintillation counter. A standard curve was prepared by plotting the cpm of bands containing known amounts of IGF-1 versus IGF-1 concentration and the IGF-1 content of the broth was estimated by comparison with the standard curve.

C. Quantitative Reverse-Phase High-Performance Liquid Chromatography (HPLC)

1. HPLC System

A Waters (Bedford, Mass.) 600 solvent delivery system, Waters Model 481 Lambda Max variable wavelength detector, Wisp 710B auto-injector and a Schimadzu Crom-Pac integrator (Cole Scientific, Moorepark, Calif.) constituted the HPLC system. A Vydac C4 column (0.46×5 cm) with a guard column was used to resolve components of the *Pichia pastoris* produced IGF-1 preparations. Broth samples that had been pretreated as described in Example 6.C.2. below were loaded onto the column at a flow rate of 1 ml/minute and were eluted in a trifluoroacetic acid (TFA)/acetonitrile-TFA gradient. The eluant was prepared by using mobile phase A (0.1% TFA) to dilute mobile phase B (95% acetonitrile, 5% water, 0.1% TFA). A 1%/minute gradient of 25% to 42% mobile phase B was passed through the column during a period of 17 minutes at a flow rate of 1 ml/minute to elute the material that had been loaded onto the column. The column was then regenerated with 100% mobile phase B at a flow rate of 2 ml/minute for 4 minutes followed by 25% mobile phase B for 4 minutes at 2 ml/minute. The flow rate was then reduced to 1 ml/minute and the column was equilibrated at the initial starting conditions (25% mobile phase B) for 2 minutes before reinjection with another sample to be analyzed. The detector was set at 0.05 absorbance units full scale (AUFS) and a wavelength of 215 nm was used for maximum sensitivity.

2. Pretreatment of crude fermentation broth.

*P. Pastoris*-produced IGF-1 exists as several forms in the broth of fermentations of IGF-1-expressing *P. pastoris* strains. HPLC analysis of crude cell-free broth from fermentations of IGF-1-expressing *P. pastoris* does not adequately resolve the various IGF-1 species. In order to distinguish these IGF-1 species by HPLC, the authentic *P. pastoris* proteins must be removed from the broth by a small-scale cation exchange chromatography step. Several cation exchange systems were tested for this purpose: sulfylpropyl cation exchange capsules (FMC (Pinebrook, N.J.) and Cuno (Meriden, Conn.)) and the use of a bulk cation exchanger (e.g., S-Sepharose Fast Flow (Pharmacia, Uppsala, Sweden), SP-Spherodex (IBF, Columbia, Md.), or Toyopearl SP650M and SP550C (Toso Haas, Woburn, Mass.)) in a 2-ml disposable polypropylene column (0.8×4 cm, BioRad) with an integrated 10-ml reservoir. Any of these systems yielded satisfactory results. The two systems routinely used to pretreat crude broth for quantitative HPLC analysis of the IGF-1 levels employed the Cuno cation exchange capsule or the SPS-pherodex or SP550C cation exchangers in a column format. The crude broth was cleaned up by cation exchange chromatography and injected directly onto an HPLC column. The resulting chromatogram clearly resolved the different IGF-1 species in broth.

a. Pretreatment using cation exchange capsules.

The Cuno cation exchange capsule is a 25-mm disk. It was first washed with a 4 ml 0.2M acetic acid, then equilibrated with 4 ml 0.02M acetic acid. A volume of crude broth (1–10 ml) was diluted 1:2 with 0.02M acetic acid and loaded onto the disk. After loading, the disk was washed with 1.5 ml 0.02M acetic acid and the IGF-1 was eluted with 4 ml 0.02M sodium acetate, pH 5.5, plus 1M NaCl. The first 1.5 ml of eluate contained 75–80% of the total IGF-1 and was usually the only elution volume collected. The capsule could then be regenerated by washing with 4 ml of 100% methanol.

b. Pre-treatment using bulk cation exchanger in a column format.

To the disposable column, 0.25 ml of prehydrated cation exchanger was added. The absorbent was first washed with 2 ml of 0.2M acetic acid, then equilibrated with 2 ml of 0.02M acetic acid. A volume of broth (1 ml) was loaded onto the column which was then washed with 1 ml of 0.02M acetic acid. All buffers and broth were carefully added to the column in an effort to avoid disruption of the column bed. Although some suspension of the absorbent usually occurred during addition of liquid to the column, it was not detrimental to sample binding or eluting. Broth samples and buffer were allowed to flow through the column by gravity. The IGF-1 was eluted with 2 ml of a 0.05M sodium acetate, pH 5.5, buffer containing 1M NaCl. The first milliliter of eluate contained 80–90% of the total IGF-1, eluted by the 2 ml of elution buffer. Periodically (approximately every 5–10 samples), the column was regenerated after the salt elution with a 50% methanol wash. Less often, the column was also regenerated with 0.5M NaOH. These columns retain their selective binding properties through many successive uses.

3. Measurements of IGP-1 concentrations.

In order to measure the concentrations of Pichia-produced IGF-1 by HPLC, known amounts of standard IGF-1 (Amgen, Thousand Oaks, Calif.) and authentic Pichia-produced IGF-1, which was purified as described in U.S. patent application Ser. No. 07/641,430) and quantified by amino acid composition analysis were injected onto the HPLC column and the area under the corresponding peaks in the chromatogram was measured. A standard curve was generated by plotting area versus micrograms of IGF-1 loaded onto the HPLC column. A conversion factor for use in converting the area under HPLC chromatogram peaks to IGF-1 concentration was calculated from the standard curve. Using this information, it was possible to determine the concentration of authentic IGF-1 in a pretreated broth sample by measuring the area under the corresponding peak on the chromatogram from HPLC analysis of the sample. This conversion factor was also used to estimate the approximate concentration of other IGF-1 species as well. The absolute concentrations of each of these other species, however, may vary depending on differences in their specific conversion factors.

Example 6

CHARACTERIZATION OP THE IGF-1 SECRETED INTO THE CULTURE MEDIUM

Pichia-produced IGF-1 was characterized by immunoblot, SDS-PAGE, HPLC, and protein sequence analyses. These methods and the results of these analyses are described in this example.

a. Immunoblot Analysis

Several characteristics of the IGF-1 produced in fermentations of IGF-1-expressing *P. pastoris* were ascertained from immunoblot analysis of reduced (by adding dithiothreitol (DTT)) and non-reduced (no added DTT) samples of broth (performed as described in Example 5B).

First, if the broth samples were not reduced prior to electrophoresis, the IGF-1 migrated as several forms which appeared to be a monomer, dimer and various multimers of IGF-1. The ratio or profile of monomer to multimer forms of secreted IGF-1 did not seem to be affected by copy number.

Second, the immunoblot of reduced samples revealed the absence of most of the higher molecular weight immunoreactive species that were evident in the nonreduced broth samples, and revealed the presence of a protein that co-migrates with IGF-1 standard (monomer) as well as immunoreactive protein which migrates to a position slightly below that of standard IGF-1. N-terminal protein sequence analysis (Example 6.d.) of this lower molecular weight immunoreactive species demonstrated that it begins with residue 25 of mature human IGF-1 and, thus, is a proteolytic fragment of IGF-1. Since this lower molecular weight species is not seen under non-reducing conditions, the IGF-1 molecule may be nicked only between residues 24 and 25, i.e., not completely fragmented, with the disulfide bonds at Cys-6/Cys-48 and Cys-18/Cys-61 of IGF-1 holding the peptide fragments that contain amino acids 1–24 and 25–70 together. Further, the decreased glycerol fermentation (Run 755) produced wholly intact IGF-1 molecules (no degradation), while the extended glycerol feed fermentation (Run 756) demonstrated a low level of degraded product. The degradation appeared to be slightly higher with the six-copy strain (Run 776) than with the four-copy strain (Run 775).

IGF-1 produced in the fermentation of the six-copy Mut⁻ strain (Run 657) was also analyzed by SDS-PAGE and Western blot. The IGF-1 band patterns of reduced and non-reduced broth from the fermentation of the six-copy Mut⁻ strain are similar to the band patterns of reduced and non-reduced broth from the fermentations of the six-copy and four-copy Mut⁻ strains.

B. Qualitative HPLC Analysis

Crude *P. pastoris* fermentation broth was also analyzed by HPLC (see Example 5.C.1 for a description of the HPLC system used in this analysis). Direct injection of crude broth onto the HPLC column did not result in a chromatogram with distinct peaks. In order to analyze the components of crude broth by HPLC, it was necessary to remove endogenous *P. pastoris* contaminants from the broth using small-scale cation exchange chromatography, as described in Example 5.C.

The eluate obtained after small-scale cation exchange chromatography of cell-free broth from a low pH fermentation of an IGF-1-expressing strain of *P. pastoris* contains all the IGF-1 polymers, including nicked, misfolded, multimeric and authentic IGF-1 which can be resolved by the HPLC protocol described in Example 5C. The different peaks detected in the chromatogram from HPLC analysis of broth that had been subjected to cation exchange chromatography correspond to different forms of IGF-1 produced in recombinant *P. pastoris* fermentations. The identity of the proteins corresponding to these peaks was established in HPLC, SDS-PAGE, immunoblots, gel filtration, cation exchange and hydrophobic interaction chromatography (performed as described in U.S. patent application Ser. No. 641,430).

A chromatogram from HPLC analysis (conducted as described in Example 5C.) of broth from a fermentation of an IGF-1-expressing *P. pastoris* strain contains a peak corresponding to protein that eluted from the HPLC column at approximately 10 minutes, which represents correctly folded, intact IGF-1 monomer. The identity of this protein was confirmed initially on the basis of its elution time by HPLC, which is identical to that of standard recombinant IGF-1 (Amgen, Thousand Oaks, Calif.). Furthermore, the protein with an elution time of approximately 10 minutes was purified (see U.S. patent application Ser. No. 641,430) and subjected to additional analyses. SDS-PAGE analysis of reduced and non-reduced samples of the purified protein yielded identical results, revealing that it was a 7.7-kDa intact protein that co-migrated with IGF-1 standard. Immunoblot analysis of the purified protein demonstrated that it is reactive with an antibody generated against the last 14 amino acids of IGF-1. Gel filtration chromatography of the purified protein revealed that it elutes as expected for an IGF-1 monomer of the correct size. Finally, amino acid analysis confirmed that the amino acid ratios of the purified protein correspond to those of standard IGF-1. Protein sequence analysis showed that the complete amino acid sequence of the purified protein is identical to that of authentic IGF-1.

The protein that elutes from the HPLC column at approximately 8.6 minutes was tentatively identified as misfolded IGF-1. This protein was isolated by HPLC and hydrophobic interaction chromatography and characterized by SDS-PAGE, immunoblot and protein sequence analysis. SDS-PAGE analysis of reduced and non-reduced samples of this protein demonstrated that this form migrated with authentic monomeric IGF-1 and that it was not a nicked form of IGF-1. Immunoblot analysis of this protein using an antibody directed against the C-terminus of IGF-1 showed that it was immunoreactive. Amino-terminal protein sequencing of this protein also confirmed that the molecule was intact since only one amino-terminal sequence could be identified. These results suggest that this form is a misfolded species of IGF-1.

The proteins that elute from an HPLC column at 10.5–11.5 minutes were identified as nicked or degraded forms of IGF-1 (i.e., IGF-1 molecules containing two or more peptide fragments, generated by cleavage of one or more peptide bonds and held together by disulfide bonds). There appears to be at least two peaks by HPLC analysis of cleaned up broth that correspond to the nicked IGF-1. The protein represented by the major peak (eluting at 10.7 minutes) was isolated during the S-Sepharose cation exchange step of the IGF-1 purification process (see U.S. patent application Ser. No. 641,430). SDS-PAGE analysis of non-reduced samples of this isolated species revealed that it co-migrated with IGF-1 standard and appeared as a single band. Gels of reduced samples of this protein, however, exhibited a doublet representing two peptides of approximately 3–4 kDa each (approximately half the size of intact IGF-1). The position of this doublet in the gel corresponded to that of the lower of the two bands detected below the band representing intact IGF-1 in gels of reduced samples of crude broth. These results indicate that this molecule is monomeric IGF-1 cleaved or nicked and held together by disulfide bonds. Amino-terminal protein sequence analysis of the protein confirmed that the molecule is nicked prior to residue 40 of IGF-1. Immunoblot analysis of reduced and non-reduced samples of this isolated nicked IGF-1 molecule revealed that it is less reactive than intact IGF-1 with the antibody directed against the C-terminus of IGF-1.

Two additional nicked species were identified in protein sequence analysis of IGF-1 recovered from the first cation exchange chromatography step of the purification process (see U.S. patent application Ser. No. 641,430). Either or both of these species could correspond to the minor peak in the HPLC chromatogram of cleaned up cell-free broth (protein eluting at 11 minutes). The amino-terminus of the C-terminal fragment of one of these nicked molecules begins at residue 25 of IGF-1. The amino terminus of the C-terminal fragment of the other nicked species detected in the broth begins at residue 14 of IGF-1.

The last set of proteins detected in HPLC analysis of cell-free broth, which elute from the HPLC column after 11.5–16 minutes, appears to be disulfide-bonded multimer forms of IGF-1. The presence of disulfide-bonded IGF-1 multimers in *P. pastoris* broth was indicated in SDS-PAGE gels of broth and immunoblots of the gels. The putative multimers migrated as IGF-1 dimers and trimers on non-reduced SDS-PAGE gels and were reactive with antibody directed against the C-terminus of IGF-1. When these multimers were reduced, they co-migrated with standard monomer IGF-1 in SDS-PAGE gels, which indicates that they contain disulfide-bonded IGF-1 monomers. The amino acid sequence generated in protein sequence analysis of gel-isolated dimer was identical to the N-terminus of authentic IGF-1. Furthermore, multimer IGF-1 (apparent dimer and trimer species) were isolated on a gel filtration column and analyzed by HPLC. The isolated multimer eluted from the column at 12–14 minutes, which corresponds to the elution times of the proteins in broth that were proposed to be multimers of IGF-1.

Example 7

CHARACTERIZATION OF PURIFIED AUTHENTIC PICHIA-PRODUCED IGF-1

Correctly folded, intact, monomeric IGF-1 (authentic IGF-1) was purified from the broth of IGF-1-expressing strains G+IMB204S14 and M+IMB206S1 using a combination of cation exchange chromatography, hydrophobic interaction chromatography and gel filtration chromatography methods. The purification procedure is described in detail in U.S. patent application Ser. No. 07/641,430. The purified material was characterized by HPLC, gel filtration chromatography, SDS-PAGE and immunoblot analysis, and amino acid composition and sequence analysis.

A. HPLC Analysis

Several different dilutions of the purified preparation were subjected to HPLC using the system and procedure described in Example 5C. A single major peak was detected in the resulting chromatogram which represented a protein with an elution time identical to that of IGF-1 standard.

B. Gel Filtration Chromatography

1. Procedure

A Superdex 75 HR 10/30 gel filtration column (pharmacia) with a bed volume of 24 ml (10×300 mm) was used in gel filtration chromatography methods of characterizing IGF-1 on the basis of size. The HPLC system described in Example 5C was modified for use with this column. The detector was set at a wavelength of 280 nm and a sensitivity of 0.02 AUFS. The gel filtration chromatography column buffer contained 0.05M ammonium acetate, pH 6. Buffer was flowed through the column at a flow rate of 0.5 ml/minute.

2. Results

The chromatogram from gel filtration chromatography analysis of 200 µg of purified IGF-1 yielded a single peak representing protein that co-eluted with IGF-1 standard.

C. SDS-PAGE and Immunoblot Analysis.

The purified material was examined by SDS-PAGE and immunoblot methods as described in Example 5B. Only a single band was detected in both silver-stained gels and immunoblots of reduced and non-reduced samples of the material containing i µg of protein or less. This protein co-migrated with IGF-1 standard.

D. Amino Acid Composition

Purified IGF-1 was acid hydrolyzed, and the amino acids were characterized on a Beckman (Palo Alto, Calif.) 6300 Amino Acid Analyzer. To acid hydrolyze the IGF-1 protein, carefully measured volumes of purified IGF-1 solution were added to 6×50 mm glass tubes and dried in a Savant (Farmingdale, N.Y.) Speed Vac. These tubes were placed in a reaction flask containing ~0.5 ml 6N HCl. Oxidation was minimized by applying a vacuum and sealing the flask. The flask was placed overnight in a 110° C. oven, and the protein was hydrolyzed by the HCl vapors.

Following hydrolysis, the reaction flask was cooled to room temperature, and the hydrolyzate was removed. Any HCl that may have condensed in the tubes was removed by drying the tubes in a Speed Vac. The free amino acids were dissolved in a minimum of 100 μl Beckman Amino Acid Sample Dilution Buffer, Na-S, for loading in the 50-μl loop of the analyzer. A Nelson (Cupertino, Calif.) 3000 Series Chromatography Data System was used to measure concentrations by comparing the integrated chromatogram of amino acid standard solutions and of the resuspended, hydrolyzed sample.

Table VI shows the amino acid ratios estimated for the purified IGF-1 and the actual published amino acid ratios for human IGF-1. The estimated and published ratios are in close agreement, and slight deviations in the estimated and published compositions are within the expected limits of this analysis.

TABLE VI

Purified IGF-1
Amino Acid Composition Analysis Data

| Amino Acid | Published Composition[a] | Experimental |
|---|---|---|
| Asp(+Asn) | 5 | 5.8 |
| Thr | 3 | 3.1 |
| Ser | 5 | 4.9 |
| Glu(+Gln) | 6 | 6.9 |
| Pro | 5 | 3.0 |
| Gly | 7 | 7.4 |
| Ala | 6 | 6.8 |
| Cys | 6 | 5.5 |
| Val | 3 | 2.6 |
| Met | 1 | 0.9 |
| Ile | 1 | 0.66 |
| Leu | 6 | 7.1 |
| Tyr | 3 | 2.1 |
| Phe | 4 | 3.6 |
| His | 0 | 0 |
| Lys | 3 | 3.3 |
| Arg | 6 | 6.7 |
| Trp | 0 | |

[a]Derived from nucleotide sequence published by Rotwein et al. (1986) J. Biol. Chem. 261:4828.

E. Amino Acid Sequence

1. Procedure

To determine the N-terminal amino acid sequence of the IGF-1 purified from the broth of strain M+IMB206S1, samples of this material were loaded directly onto an Applied Biosystems (Foster City, Calif.) 470/120 Gas Phase Protein Sequencer. Sequencing was performed according to the methods described by Hunkapiller and Hood (*Science* 215: 650 (1983)).

To determine the entire amino acid sequence of IGF-1 purified from the broth of strain G+IMB204S14, the material was sequenced from the N-terminal amino acid through as much of the remainder of the protein sequence as possible. This analysis generated the sequence of the first 59 residues of the purified protein. Because the amino acid at residue 59 is a methionine residue, and cyanogen bromide cleaves proteins after methionine residues, it was possible to isolate the peptide containing the C-terminal 11 amino acids (residues 60–70) of purified IGF-1 for use in completing the protein sequence analysis of the purified material. The C-terminal 11 amino acids of the purified IGF-1 were obtained as a peptide fragment isolated from cyanogen bromide-treated IGF-1 by HPLC, using the same C4 column as described in Example 5C. This fragment was loaded onto the protein sequencer to generate the sequence of the C-terminal amino acids (amino acids 60–70).

The N-terminal amino acid sequences of authentic IGF-1 from the broth of fermentations of strains G+IGF816S1 and G+IGF816S11 were also determined. The broth was pre-treated as described in Example 5C and subjected to HPLC (also as described in Example 5C). The fraction that eluted from the HPLC column with an elution time identical to that of standard IGF-1 was applied to an SP-Spherodex column to remove the HPLC solvent (acetonitrile and TFA). The eluate fraction containing the IGF-1 was then loaded directly onto the protein sequencer.

2. Results

The first 30 amino acids of the IGF-1 purified from the broth of strain M+IMB206S1 and the entire amino acid sequence of IGF-1 purified from broth of strain G+IMB204S14 were identical to the corresponding amino acids of human IGF-1, Sequence ID No. 1 (i.e., residues 2–31).

Similarly, the first 15 amino acids of the IGF-1 from the broth of strains G+IGF816S1 and G+IGF816S11 were identical to the corresponding amino acids of human IGF-1. These results confirm that mature IGF-1 is correctly processed from the αMF prepro-lys-arg-IGF-1 or αMF prepro-lys-arg-glu-ala-IGF-1 precursor in *P. pastoris*.

Since modifications will be apparent to those of skill in the art, it is intended that this invention be limited only by the scope of the appended claims.

That which is claimed:

1. A DNA construct, comprising one or more copies of an expression cassette that contains:
   (a) a sequence of nucleotides encoding an insulin-like growth factor-1 (IGF-1) peptide;
   (b) a promoter region from a methanol responsive gene of a methylotrophic yeast operably linked to the sequence of nucleotides that encodes IGF-1;
   (c) a sequence of nucleotides encoding the *Saccharomyces cerevisiae* α-mating factor (αMF) pre-pro sequence;
   (d) a transcription terminator functional in a methylotrophic yeast host cell operably linked to the sequence of nucleotides that encodes an IGF-1 peptide, wherein:
   the sequence of nucleotides that encodes the pre-pro sequence is operably linked via a sequence of nucleotides encoding the processing site lys-arg to the sequence of nucleotides that encodes an IGF-1 peptide;
   the promoter region directs methanol-induced transcription in a methylotrophic yeast host of the sequence of nucleotides encoding the pre-pro sequence and the IGF-1 peptide; and
   the methylotrophic yeast is a species that utilizes methanol as a sole carbon source and is a member of the genus Hansenula or Pichia.

2. A DNA construct of claim 1, further comprising at least one selectable marker gene and a bacterial origin of replication.

3. A plasmid, comprising the DNA construct of claim 2.

4. The plasmid of claim 3 that is selected from the group consisting of pIGF201, pIGF202, pIGF204 and pIGF206.

5. The DNA construct of claim 1, wherein the sequence of nucleotides encoding an IGF-1 peptide has the sequence set forth in FIG. 1.

6. A methylotrophic yeast cell, comprising the DNA construct of claim 5, wherein the methylotrophic yeast is a species that utilizes methanol as a sole carbon source and is a member of the genus Hansenula or Pichia.

7. The DNA construct of claim 1, wherein the promoter region directs methanol-induced transcription in *Pichia pastoris* of the sequence of nucleotides encoding the IGF-1 peptide.

8. The DNA construct of claim 7, wherein said methanol-responsive gene of a methylotrophic yeast and the transcription terminator are derived from the *P. pastoris* AOX1 gene.

9. The DNA construct of claim 8, wherein the 3'- and 5'-ends of the construct have sufficient homology with a target gene of a yeast host to effect site directed integration of said construct into said target gene.

10. A DNA construct of claim 9, comprising multiple copies of said expression cassette.

11. A *P. pastoris* cell, comprising the DNA construct of claim 10.

12. The *P. pastoris* cell of claim 11, wherein said cell is selected from strains G+IGF206S2, G+IMB202S2, G+IMB204S14, G+IMB206S1, G–IMB206S2, G+IMB206S3, G-IMB206S1 and M+IMB206S1.

13. A culture of viable *P. pastoris* cells, comprising yeast cells of claim 12.

14. The *P. pastoris* cell of claim 11, wherein said cell is selected from the group consisting of strains G+IGF206S2, G-IMB206S3, G+IMB206S1, G+IMB202S2, and G+IMB204S14.

15. A culture of viable *P. pastoris* cells, comprising yeast cells of claim 11.

16. The *P. pastoris* cell of claim 11, wherein the cell is selected from the group consisting of strains G+IGF202S3, G+IGF202S5, G+IGF204S2, G+IGF204S8, G+IGF206S2, G+IGF206S5, G+IGF206S8, G+IGF206S9, G+IMB202S2, G+IMB204S14, G+IMB206S1 and G+IMB206S3.

17. A *Pichia pastoris* cell, comprising the DNA construct of claim 9.

18. A culture of viable *P. pastoris* cells, comprising yeast cells of claim 17.

19. The *P. pastoris* cell of claim 17 that is selected from the group consisting of strains G+IGF201S1, G+IGF201S2, G+IGF201S6 and G+IGF201S10.

20. A DNA construct of claim 1, wherein the 3'- and 5'-ends of the construct have sufficient homology with a target gene of a yeast host to effect site directed integration of said construct into said target gene.

21. A DNA construct of claim 1, comprising multiple copies of said expression cassette.

22. The DNA construct of claim 21, wherein said multiple copies of said expression cassette are oriented in head-to-tail orientation.

23. A methylotrophic yeast cell, comprising the DNA construct of claim 4, wherein the methylotrophic yeast is a species that utilizes methanol as a sole carbon source and is a member of the genus Hansenula or Pichia.

24. A process for producing insulin-like growth factor-1 (IGF-1) peptides, comprising culturing the cells of claim 23 under conditions whereby said cells express and secrete mature IGF-1 peptide into the culture medium.

25. The process of claim 24, wherein said methylotrophic yeast is a strain of *Pichia pastoris*.

26. The process of claim 24, wherein said cells are grown in a medium containing methanol as a carbon source.

27. The process of claim 24, wherein said cells have the Mut$^+$phenotype.

28. The process of claim 24, wherein said cells have the Mut$^-$ phenotype.

29. The process of claim 27, wherein the initial pH of the culture medium is about 5, which decreases and is maintained between about 2 and about 4 prior to and during induction of the methanol responsive promoter.

30. The process of claim 29, wherein the pH is maintained at less than about 3.

31. The process of claim 24, wherein the cells are protease deficient Pichia cells that are deficient in proteinase B activity or are deficient in proteinase A and carboxypeptidase Y activities; and the initial pH of the culture medium is about 5 and is maintained at a pH of between about 2 and 5 prior to induction of the methanol responsive promoter.

32. A methylotrophic yeast cell, comprising the DNA construct of claim 1, wherein the methylotrophic yeast is a species that utilizes methanol as a sole carbon source and is a member of the genus Hansenula or Pichia.

33. The methylotrophic yeast cell of claim 32, wherein said yeast is a strain of *Pichia pastoris*.

34. The strain of claim 33, wherein said strain is a protease deficient Pichia strain that is deficient in proteinase B activity or are deficient in proteinase A and carboxypeptidase Y activities.

35. The strain of claim 34, wherein said deficiency results in an absence or reduction in the concentration of one or more proteinases selected from the group consisting of proteinase A, carboxypeptidase Y, and proteinase B.

36. The strain of claim 33, that is M+IGF816S1 or M+IGF816S4.

37. The strain of claim 35 that is a PEP4⁻ IGF-1expressing strain.

38. The strain of claim 35 that is a PEP4⁻, PRB-1⁻ IGF-1-expressing strain.

39. The strain of claim 38 that is C+IGF816S1.

40. The strain of claim 34 that is M+IMB206S1.

41. A culture of viable methylotrophic yeast cells, comprising yeast cells of claim 32.

42. A process for producing insulin-like growth factor-1 (IGF-1) peptides, comprising culturing the cells of claim 32, under conditions whereby said cells express and secrete mature IGF-1 peptide into the culture medium.

43. A process of claim 42 wherein said methylotrophic yeast is a strain of *Pichia pastoris*.

44. The process of claim 42, wherein said cells are cultured in a medium containing methanol as a carbon source.

45. The process of claim 42, wherein said cells have the Mut⁺ phenotype.

46. The process of claim 42, wherein said cells have the Mut⁻ phenotype.

47. The process of claim 42, wherein the initial pH of the culture medium is about 5, which decreases, and is maintained between 2 and about 4 prior to induction of the methanol responsive promoter.

48. The process of claim 47, wherein the pH is maintained at less than about 3.

49. The process of claim 42, wherein said cells are protease deficient Pichia cells and the initial pH of the culture medium is about 5 and is maintained between about 2 and 5 prior to induction of the methanol responsive promoter.

50. A DNA construct, comprising one or more copies of an expression cassette that contains:

(a) a sequence of nucleotides encoding an insulin-like growth factor-1 (IGF-1) peptide;

(b) a promoter region from a methanol responsive gene of a methylotrophic yeast operably linked to the sequence of nucleotides that encodes IGF-1;

(c) a sequence of nucleotides encoding the *Saccharomyces cerevisiae* α-mating factor (αMF) pre-pro sequence;

(d) a transcription terminator functional in a methylotrophic yeast host cell operably linked to the sequence of nucleotides that encodes an IGF-1 peptide, wherein:

the sequence of nucleotides that encodes the pre-pro sequence is operably linked via a sequence of nucleotides encoding one or more processing sites selected from the group consisting of lys-arg and lys-arg-(glu-ala)$_x$ to the sequence of nucleotides that encodes an IGF-1 peptide;

x is 1, 2 or 3;

the promoter region directs methanol-induced transcription in a methylotrophic yeast host of the sequence of nucleotides encoding the signal sequence and the IGF-1 peptide; and the methylotrophic yeast is a species that utilizes methanol as a sole carbon source and is a member of the genus Hansenula or Pichia.

51. The plasmid of claim 50 that is pIGF816.

52. The DNA construct of claim 50, wherein:

the processing site is lys-arg-(glu-ala)$_x$; and x is 3.

53. The DNA construct of claim 50, wherein:

the processing site is lys-arg-(glu-ala)$_x$; and x is 1.

54. The DNA construct of claim 50, wherein: the processing site is lys-arg-(glu-ala)$_x$; and x is 2.

55. A *P. pastoris* cell selected from the group consisting of strains G+IGF816S1, G+IGF816S2, G+IGF816S9 and G+IGF816S11.

56. A culture of viable *P. pastoris* cells, comprising yeast cells of claim 55.

* * * * *

UNITED STATES PATENT AND TRADEMARK OFFICE
CERTIFICATE OF CORRECTION

PATENT NO. : 5,612,198
DATED : March 18, 1997
INVENTOR(S) : Brierley, et. al.

It is certified that error appears in the above-identified patent and that said Letters Patent is hereby corrected as shown below:

ON THE TITLE PAGE:

On the title page of the patent, section [73], entitled "Assignee" should read —SIBIA Neurosciences, La Jolla. California—.

In column 1, line 17, insert —U.S.— before "application";
In column 14, line 61, "BHI" should read —HI—;
In column 14, line 61, insert —which— before "may be"; and
In column 18, line 65, insert —Twenty µg of pYSV201— before "plasmid".

In claim 23, column 58, line 35, "4" should read —21—;
In claim 29, column 58, line 50, "27" should read —24—;
In claim 36, column 59, line 9, "33" should read —35—; and
In claim 50, column 60, line 25, "signal" should read —pre-pro—.

Signed and Sealed this

Ninth Day of June, 1998

Attest:

BRUCE LEHMAN

Attesting Officer

Commissioner of Patents and Trademarks